(12) United States Patent
Phiasivongsa et al.

(10) Patent No.: US 10,456,415 B2
(45) Date of Patent: Oct. 29, 2019

(54) OLIGONUCLEOTIDE ANALOGUES INCORPORATING 5-AZA-CYTOSINE THEREIN

(71) Applicant: Astex Pharmaceuticals, Inc., Pleasanton, CA (US)

(72) Inventors: Pasit Phiasivongsa, Brentwood, CA (US); Sanjeev Redkar, Hayward, CA (US)

(73) Assignee: ASTEX PHARMACEUTICALS, INC., Pleasanton, CA (US)

( * ) Notice: Subject to any disclaimer, the term of this patent is extended or adjusted under 35 U.S.C. 154(b) by 290 days.

(21) Appl. No.: 15/278,550

(22) Filed: Sep. 28, 2016

(65) Prior Publication Data

US 2017/0035794 A1 Feb. 9, 2017

Related U.S. Application Data

(60) Division of application No. 14/979,148, filed on Dec. 22, 2015, now Pat. No. 9,480,698, which is a continuation of application No. 13/894,288, filed on May 14, 2013, now Pat. No. 9,358,248, which is a continuation of application No. 12/703,096, filed on Feb. 9, 2010, now Pat. No. 8,461,123, which is a continuation of application No. 11/241,799, filed on Sep. 29, 2005, now Pat. No. 7,700,567.

(51) Int. Cl.
| | |
|---|---|
| *A61K 31/70* | (2006.01) |
| *C12N 15/11* | (2006.01) |
| *A61K 31/7084* | (2006.01) |
| *C07H 21/00* | (2006.01) |
| *A61K 31/282* | (2006.01) |
| *A61K 31/337* | (2006.01) |
| *A61K 31/4406* | (2006.01) |
| *A61K 33/24* | (2019.01) |
| *A61K 45/06* | (2006.01) |
| *A61K 9/00* | (2006.01) |
| *C07H 19/20* | (2006.01) |

(52) U.S. Cl.
CPC ........ *A61K 31/7084* (2013.01); *A61K 9/0019* (2013.01); *A61K 9/0053* (2013.01); *A61K 31/282* (2013.01); *A61K 31/337* (2013.01); *A61K 31/4406* (2013.01); *A61K 33/24* (2013.01); *A61K 45/06* (2013.01); *C07H 19/20* (2013.01); *C07H 21/00* (2013.01); *C12N 15/111* (2013.01); *C12N 2310/11* (2013.01); *C12N 2310/317* (2013.01); *C12N 2310/334* (2013.01); *C12N 2310/336* (2013.01); *C12N 2320/30* (2013.01); *C12N 2330/30* (2013.01)

(58) Field of Classification Search
CPC ... A61K 31/7084; C12N 15/111; C07H 21/00
USPC ...................... 524/44 R; 536/23.1
See application file for complete search history.

(56) References Cited

U.S. PATENT DOCUMENTS

| | | |
|---|---|---|
| 4,690,918 A | 9/1987 | Beppu et al. |
| 4,855,304 A | 8/1989 | Devash |
| 5,157,120 A | 10/1992 | Ogilvie |
| 5,607,691 A | 3/1997 | Hale et al. |
| 5,736,531 A | 4/1998 | Von Borstel et al. |
| 5,856,090 A | 1/1999 | Epstein |
| 5,968,914 A | 10/1999 | Von Borstel et al. |
| 6,136,791 A | 10/2000 | Nyce |
| 6,153,383 A | 11/2000 | Verdine et al. |
| 6,432,924 B1 | 8/2002 | Nyce |
| 6,472,521 B1 | 10/2002 | Uhlmann et al. |
| 6,905,669 B2 | 6/2005 | Dimartino |
| 6,982,253 B2 | 1/2006 | Joshi-Hangal et al. |
| 6,998,391 B2 | 2/2006 | Lyons et al. |
| 7,135,464 B2 | 11/2006 | Joshi-Hangal et al. |
| 7,144,873 B2 | 12/2006 | Joshi-Hangal et al. |
| 7,250,416 B2 | 7/2007 | Phiasivongsa et al. |

(Continued)

FOREIGN PATENT DOCUMENTS

| | | |
|---|---|---|
| CN | 101282986 A | 10/2008 |
| CN | 101361718 A | 2/2009 |

(Continued)

OTHER PUBLICATIONS

Chuang, et al. S110, a 5-Aza-2'-deoxycytidine-containing dinucleotide, is an effective DNA methylation inhibitor in vivo and can reduce tumor growth. Molecular cancer therapeutics 9.5 (2010): 1443-1450.

(Continued)

*Primary Examiner* — Jezia Riley

(74) *Attorney, Agent, or Firm* — Wilson Sonsini Goodrich & Rosati

(57) ABSTRACT

Oligonucleotide analogues are provided that incorporate 5-aza-cytosine in the oligonucleotide sequence, e.g., in the form of 5-aza-2'-deoxycytidine (decitabine) or 5-aza-cytidine. In particular, oligonucleotide analogues rich in decitabine-deoxyguanosine islets (DpG and GpD) are provided to target the CpG islets in the human genome, especially in the promoter regions of genes susceptible to aberrant hypermethylation. Such analogues can be used for modulation of DNA methylation, such as effective inhibition of methylation of cytosine at the C-5 position. Methods for synthesizing these oligonucleotide analogues and for modulating nucleic acid methylation are provided. Also provided are phosphoramidite building blocks for synthesizing the oligonucleotide analogues, methods for synthesizing, formulating and administering these compounds or compositions to treat conditions, such as cancer and hematological disorders.

46 Claims, 42 Drawing Sheets

Specification includes a Sequence Listing.

(56) References Cited

U.S. PATENT DOCUMENTS

| | | |
|---|---|---|
| 7,276,228 B2 | 10/2007 | Dimartino |
| 7,700,567 B2 | 4/2010 | Phiasivongsa et al. |
| 8,461,123 B2 | 6/2013 | Phiasivongsa et al. |
| 9,358,248 B2 | 6/2016 | Phiasivongsa et al. |
| 9,381,207 B2 | 7/2016 | Joshi-Hangal et al. |
| 9,480,698 B2 | 11/2016 | Phiasivongsa et al. |
| 9,913,856 B2 | 3/2018 | Joshi-Hangal et al. |
| 2001/0012835 A1 | 8/2001 | Fine et al. |
| 2002/0114809 A1 | 8/2002 | Rubinfeld et al. |
| 2003/0039689 A1 | 2/2003 | Chen et al. |
| 2003/0045497 A1 | 3/2003 | Widegren et al. |
| 2003/0108588 A1 | 6/2003 | Chen et al. |
| 2003/0147813 A1 | 8/2003 | Lyons |
| 2003/0158598 A1 | 8/2003 | Ashton et al. |
| 2003/0229047 A1 | 12/2003 | Joshi-Hangal et al. |
| 2004/0019036 A1 | 1/2004 | Robin et al. |
| 2004/0052864 A1 | 3/2004 | Rubinfeld et al. |
| 2004/0109846 A1 | 6/2004 | Rubinfeld et al. |
| 2004/0162263 A1 | 8/2004 | Sands et al. |
| 2004/0224919 A1 | 11/2004 | Rubinfeld et al. |
| 2005/0037992 A1 | 2/2005 | Lyons et al. |
| 2005/0059682 A1 | 3/2005 | Rubinfeld |
| 2005/0159375 A1 | 7/2005 | Srivastava et al. |
| 2005/0209186 A1 | 9/2005 | Lyons |
| 2005/0266012 A1 | 12/2005 | Andrieu et al. |
| 2006/0014949 A1 | 1/2006 | Redkar et al. |
| 2006/0063735 A1 | 3/2006 | Redkar et al. |
| 2006/0069060 A1 | 3/2006 | Redkar et al. |
| 2006/0074046 A1 | 4/2006 | Redkar et al. |
| 2006/0128653 A1 | 6/2006 | Tang et al. |
| 2006/0128654 A1 | 6/2006 | Tang et al. |
| 2006/0140947 A1 | 6/2006 | Lyons et al. |
| 2006/0205687 A1 | 9/2006 | Phiasivongsa et al. |
| 2007/0072796 A1 | 3/2007 | Phiasivongsa et al. |
| 2007/0105792 A1 | 5/2007 | Dimartino |
| 2007/0117776 A1 | 5/2007 | Lyons |
| 2007/0254835 A1 | 11/2007 | Lyons et al. |
| 2008/0108559 A1 | 5/2008 | Dimartino |
| 2010/0062992 A1 | 3/2010 | Redkar et al. |
| 2010/0215729 A1 | 8/2010 | Phiasivongsa et al. |
| 2013/0236536 A1 | 9/2013 | Phiasivongsa et al. |
| 2014/0303107 A1 | 10/2014 | Joshi-Hangal et al. |
| 2016/0015805 A1 | 1/2016 | Azab et al. |
| 2016/0130296 A1 | 5/2016 | Phiasivongsa et al. |
| 2016/0346310 A1 | 12/2016 | Joshi-Hangal et al. |
| 2017/0000738 A1 | 1/2017 | Joshi-Hangal et al. |

FOREIGN PATENT DOCUMENTS

| | | | |
|---|---|---|---|
| CS | 269077 B1 | 4/1990 | |
| DE | 1922702 A1 | 11/1969 | |
| DE | 2105468 A1 | 11/1971 | |
| EP | 0251464 A2 | 1/1988 | |
| EP | 0286958 A2 | 10/1988 | |
| EP | 0334368 A2 | 9/1989 | |
| EP | 0393575 B1 | 3/1994 | |
| EP | 0515156 B1 | 2/1996 | |
| JP | H05219974 A | 8/1993 | |
| JP | 2002223753 A | 8/2002 | |
| JP | 2002370939 A | 12/2002 | |
| JP | 2003310293 A | 11/2003 | |
| JP | 5030958 B2 | 9/2012 | |
| WO | WO-8909779 A1 | 10/1989 | |
| WO | WO-9301202 A1 | 1/1993 | |
| WO | WO-9307295 A1 | 4/1993 | |
| WO | WO-9426761 A1 | 11/1994 | |
| WO | WO-9427632 A1 | 12/1994 | |
| WO | WO-9515373 A2 | 6/1995 | |
| WO | WO-9611280 A1 | 4/1996 | |
| WO | WO-9636693 A1 | 11/1996 | |
| WO | WO-9639035 A1 | 12/1996 | |
| WO | WO-9640165 A1 | 12/1996 | |
| WO | WO-9723230 A1 | 7/1997 | |
| WO | WO-9816186 A2 | 4/1998 | |
| WO | WO-9940188 A2 | 8/1999 | |
| WO | WO-0023112 A1 | 4/2000 | |
| WO | WO-0037504 A2 | 6/2000 | |
| WO | WO-0040269 A2 | 7/2000 | |
| WO | WO-0062075 A1 | 10/2000 | |
| WO | WO-0074634 A2 | 12/2000 | |
| WO | WO-0114424 A2 | 3/2001 | |
| WO | WO-0129235 A2 | 4/2001 | |
| WO | WO-0169262 A1 | 9/2001 | |
| WO | WO-0221140 A1 | 3/2002 | |
| WO | WO-02053138 A2 | 7/2002 | |
| WO | WO-02057425 A2 | 7/2002 | |
| WO | WO-02069903 A2 | 9/2002 | |
| WO | WO-02076486 A2 | 10/2002 | |
| WO | WO-02083705 A1 | 10/2002 | |
| WO | WO-02085400 A1 | 10/2002 | |
| WO | WO-02087586 A1 | 11/2002 | |
| WO | WO-02094859 A2 | 11/2002 | |
| WO | WO-02101353 A2 | 12/2002 | |
| WO | WO-03012085 A1 | 2/2003 | |
| WO | WO-03012112 A1 | 2/2003 | |
| WO | WO-03020252 A2 | 3/2003 | |
| WO | WO-03026574 A2 | 4/2003 | |
| WO | WO-03031932 A2 | 4/2003 | |
| WO | WO-03040363 A1 | 5/2003 | |
| WO | WO-03043631 A2 | 5/2003 | |
| WO | WO-03045427 A2 | 6/2003 | |
| WO | WO-03046190 A1 | 6/2003 | |
| WO | WO-03062826 A2 | 7/2003 | |
| WO | WO-03065995 A2 | 8/2003 | |
| WO | WO-03076660 A1 | 9/2003 | |
| WO | WO-03092623 A2 | 11/2003 | |
| WO | WO-03103687 A1 | 12/2003 | |
| WO | WO-03104427 A2 | 12/2003 | |
| WO | WO-2005032475 A2 | 4/2005 | |
| WO | WO-2006048749 A1 | 5/2006 | |
| WO | WO-2006063111 A2 | 6/2006 | |
| WO | WO-2006071491 A1 | 7/2006 | |
| WO | WO-2006071983 A2 | 7/2006 | |
| WO | WO-2006099132 A1 | 9/2006 | |
| WO | WO-2006116713 A1 | 11/2006 | |
| WO | WO-2006121168 A1 | 11/2006 | |
| WO | WO-2007005874 A2 | 1/2007 | |
| WO | WO-2007041071 A2 | 4/2007 | |
| WO | WO-2011128642 A1 | 10/2011 | |
| WO | WO-2012033953 A1 | 3/2012 | |
| WO | WO-2012140627 A1 | 10/2012 | |
| WO | WO-2013033176 A1 | 3/2013 | |
| WO | WO-2013117969 A1 | 8/2013 | |
| WO | WO-2014134355 A1 | 9/2014 | |
| WO | WO-2017004538 | 1/2017 | |

OTHER PUBLICATIONS

Office action dated May 26, 2017 for U.S. Appl. No. 15/174,386.

European Serial No. 18177788.9 Extended Search Report dated Jan. 4, 2019.

Gupta, V. Das. Effect of Ethanol, Glycerol, and Propylene Glycol on the Stability of Phenobarbital Sodium. Journal of Pharmaceutical Sciences. Nov. 1984. vol. 73, No. 11; 1661-1662.

International search report and written opinion dated Jan. 29, 2019 for PCT Application No. PCT/IB2018/000992.

Strickley, Robert G. Solubilizing Excipients in Oral and Injectable Formulations. Pharmaceutical Research. Feb. 2004; vol. 21, No. 2; 201-230.

U.S. Appl. No. 14/771,011 Final Office Action dated Jan. 18, 2019.

U.S. Appl. No. 15/200,086 Final Office Action dated Jan. 10, 2019.

U.S. Appl. No. 15/879,802 Non-Final Office Action dated Feb. 21, 2019.

Das Gupta, V. Effect of ethanol, glycerol, and propylene glycol on the stability of phenobarbital sodium. J Pharm Sci. Nov. 1984;73(11):1661-2.

Dear, Anthony E. Epigenetic Modulators and the New Immunotherapies. N Engl J Med. Feb. 18, 2016;374(7):684-6.

Maio et al. Molecular Pathways: At the Crossroads of Cancer Epigenetics and Immunotherapy. Clin Cancer Res. Sep. 15, 2015;21(18):4040-7.

(56) References Cited

OTHER PUBLICATIONS

Sigalotti et al. Epigenetic drugs as immunomodulators for combination therapies in solid tumors. Pharmacol Ther. Jun. 2014;142(3):339-50.
Strickley, Robert G. Solubilizing excipients in oral and injectable formulations. Pharm Res. 21(2):201-230 (2004).
U.S. Appl. No. 14/771,011 Office Action dated Jun. 13, 2018.
U.S. Appl. No. 15/200,086 Office Action dated Jun. 15, 2018.
Wrangle et al. Alterations of immune response of Non-Small Cell Lung Cancer with Azacytidine. Oncotarget. Nov. 2013;4(11):2067-79.
Yang et al. Expression of PD-L1, PD-L2, PD-1 and CTLA4 in myelodysplastic syndromes is enhanced by treatment with hypomethylating agents. Leukemia. Jun. 2014;28(6):1280-8.
Avino, A. et al. Preparation and Properties of Oligodeoxynucleotides Containing 4-O-Butylthymine, 2-Fluorohypoxanthine and 5-Azacytosine. Bioorganic & Medicinal Chemistry Letters. 1995; 5(20): 2331-2336.
Barnette, W. E. N-Fluoro-N-alkylsulfonamides: Useful Reagents for the Fluorination of Carbanions. J. Am. Chem. Soc. 1984; 106:452-454.
Baylin, et al. Alterations in DNA Methylation: A Fundamental Aspect of Neoplasia. Cancer Res. 1998; 72:141-196.
Bigey, P. et al. Modified Ologonucleotides as Bona Fide Antagonists of Proteins Interacting with DNA. The Journal of Biological Chemistry. 1999; 274(8): 4594-4606.
Bouchard, et al. Incorporation of 5-Aza-2'-deoxycytidine-5'-triphosphate into DNA. Interactions with mammalian DNA polymerase alpha and DNA methylase. Mol. Pharmacol. 1983; 24: 109-14.
Brank, A. S. et al. Inhibition of HhaI DNA (Cytosine-C5) Methyltransferase by Oligodeoxyribonucleotides Containg 5-Aza-2'-deoxycytidine: Examination of the Intertwined Roles of Cofactor, Target, Transition State Structure and Enzyme Conformation. J. Mol. Biol. 2002; 323: 53-67.
Brown, R. et al. Demethylation of DNA by decitabine in cancer chemotherapy. Expert Rev Anticancer Ther. 2004; 4(4): 501-510.
Chabot, et al. Kinetics of deamination of 5-aza-2'-deoxycytidine and cytosine arabinoside by human liver cytidine deaminase and its inhibition by 3-deazauridine, thymidine or uracil arabinoside. Biochemical Pharmacology. 1983; 32:1327-1328.
Commercon, et al. Substitution of vinylic iodides by various copper(I) and copper (II) derivatives. J. Organometallic Chem. 1975; 93:415-421.
Co-pending U.S. Appl. No. 15/174,386, filed Jun. 6, 2016.
Daskalakis, et al. Expression of a Hypermethylated and Silenced P15/INK4B Gene in a Subgroup of MDS Patients is Restored by Treatment With the Methylation Inhibitor 5-Aza-2'-Deoxycytidine. Abstracts Leukemia Research. 2001; Suppl. No. 1:S16-S17.
Dax, et al. Synthesis of deoxyfluoro sugars from carbohydrate precursors. Carbohydr Res. 2000; 327:47-86.
Desimone, et al. Maintenance of elevated fetal hemoglobin levels by decitabine during dose interval treatment of sickle cell anemia. Blood. 2002; 99(11):3905-8.
Eritja, et al. Synthesis and properties of oligonucleotides containing 5-Aza-2'-deoxycytidine. Nucleosides and Nucleotides. 1997; 16(7-9):1111-114.
Esteller, M. A Gene Hypermethylation Profile of Human Cancer. Cancer Research. 2001; 61:3225-3229.
Esteller, M. CpG Island Hypermethylation and Tumor Suppressor Genes: a Booming Present, a Brighter Future. Oncogene. 2002; 21:5427-5440.
Esteller, M. Epigenetic Lesions Causing Genetic Lesions in Human Cancer: Promoter Hypermethylation of DNA Repair Genes. European Journal of Cancer. 2000; 36:2294-2300.
European search report and opinion dated Jul. 15, 2013 for EP Application No. 06804123.5.
European search report and search opinion dated Sep. 18, 2015 for EP Application No. EP15161013-6.
Fernández, et al. Synthesis of 2-Deoxy-3,5-di-O-benzoyl-2,2-difluoro-D-ribose from D-Glucose and D-Mannose. A Formal Synthesis of Gemcitabine. Tetrahedron. 1998; 54:3523-3532.
Francis, et al. Reaction of tetrahydrofolic acid with cyanate from urea solutions: formation of an inactive folate derivative. Am. J. Clin. Nutr. 1977; 30:2028-2032.
Gagnon, et al. Interaction of 5-aza-2'-deoxycytidine and Depsipeptide on Antineoplastic Activity and Activation of 14-3-3σ, E-Cadherin and Tissue Inhibitor of Metalloproteinase 3 Expression in Human Breast Carcinoma Cells. Anti-Cancer Drugs. 2003; 14(3):193-202.
Garcia, R. G. et al. Synthesis of Oligonucleotide Inhibitors of DNA (Cytosine-C5) Methyltransferase Containing 5-Azacytosine Residues at Specific Sites. Antisense & Nucleic Acid Drg Development. 2001; 11: 369-378.
Gilbert, J. et al. The Clinical Application of Targeting Cancer through Histone Acetylation and Hypomethylation. Clinical Cancer Research. 2004; 10: 4589-4596.
Hanna, Naeem B. et. al. Synthesis of some 6-substituted 5-azacytidines. Collect. Czech. Chem. Commun. 1998; 63:222-230.
Heikkila, et al. Synthesis of adenylyl-(3'—5')-guanosine and some analogues as probes to explore the molecular mechanism of stimulation of influenza virus RNA polymerase. Acta Chem Scand B. 1985;39(8):657-69.
Herman, J. G. et al. Gene Silencing in Cancer in Association with Promoter Hypermethylation. The New England Journal of Medicine. 2003; 349(21): 2042-2054.
Honda, et al. RNA polymerase of influenza virus. Dinucleotide-primed initiation of transcription at specific positions on viral RNA. J Biol Chem. May 5, 1986;261(13):5987-91.
International search report and written opinion dated Jul. 27, 2007 for PCT/US2006/037313.
International search report and written opinion dated Nov. 7, 2012 for PCT/US2012/052816.
Issa, et al. Phase 1 study of low-dose prolonged exposure schedules of the hypomethylating agent 5-aza-2'-deoxycytidine (decitabine) in hematopoietic malignancies. Blood. 2004; 103(5): 1635-40.
Issa, J.P. Decitabine. Current Opinion in Oncology. 2003; 15(6): 446-451.
IUPAC Compendium of Chemical Terminology—glycosyl. IUPAC Pure and Applied Chemistry. 1995; 67:1338.
Jones, et al. The Fundamental Role of Epigenetic Events in Cancer. Nature Reviews/Genetics. 2002; 3:415-428.
Jones, et al. The Role of DNA Methylation in Cancer. Adv. Cancer Res. 1990; 54:1-23.
Jones, P. A. DNA methylation and cancer. Oncogene. 2002; 21:5358-5360.
Juttermann, et al. Toxicity of 5-aza-2'-deoxycytidine to mammalian cells is mediated primarily by covalent trapping of DNA methyltransferase rather than DNA demethylation. Proc Natl Acad Sci U S A. 1994; 91:11797-11801.
Karpf, et al. Reactivating the Expression of Methylation Silenced Genes in Human Cancer. Oncogene. 2002; 21:5496-5503.
Kissinger, et al. Determination of the antileukemia agents cytarabine and azacitidine and their respective degradation products by high-performance liquid chromatography. J. Chromat. 1986; 353:309-318.
La Rosee, et al. In Vitro Efficacy of Combined Treatment Depends on the Underlying Mechanism of Resistance in Imatinib-Resistant Bcr-Abl positive Cell Lines. Blood First Edition Paper. prepublished online 2003; DOI 10.1182/blood-2003-04-1074, pp. 1-39.
Lee, et al. Stereospecific synthesis of alkenyl fluorides (with retention) via organometallic intermediates. J. Am. Chem. Soc. 1986; 108:2445-2447.
Leone, G. et al. DNA methylation and demethylating drugs in myelodysplastic syndromes and secondary leukemias. Haematologica. 2002; 87(12): 1324-1341.
Leone, G. et al. Inhibitors of DNA methylation in the treatment of hematological malignancies and MDS. Clin Immunol. 2003; 109(1): 89-102.
Lin, K.S. et al. High-Performance Liquid Chromatographic Analysis of Chemical Stability of 5-Aza-2'-deoxycytidine. Journal of Pharmaceutical Sciences. 1981; 70(11): 1228-1232.

(56) References Cited

OTHER PUBLICATIONS

McIntosh, et al. Synthesis and characterization of poly[d(G-aza5C)] B-Z transition and inhibition of DNA methylase. Biochemistry. 1985; 24(18):4806-4814.
Mojaverian, et al. Development of an intravenous formulation for the unstable investigational cytotoxic nucleosides 5-azacytosine arabinoside (NSC 281272) and 5-azacytidine (NSC 102816). J. Pharm. Pharmacol. 1984; 36:728-733.
Momparler, et al. Molecular, cellular and animal pharmacology of 5-aza-2'-deoxycytidine. Pharmacol Ther. 1985; 30:287-99.
Nephew, et al. Epigenetic gene silencing in cancer initiation and progression. Cancer Letters. 2003; 190:125-133.
Notice of allowance dated Feb. 12, 2016 for U.S. Appl. No. 13/894,288.
Notice of allowance dated Feb. 15, 2013 for U.S. Appl. No. 12/703,096.
Notice of allowance dated Mar. 2, 2016 for U.S. Appl. No. 13/894,288.
Notice of allowance dated Mar. 7, 2016 for U.S. Appl. No. 14/241,635.
Notice of allowance dated Jul. 1, 2016 for U.S. Appl. No. 14/979,148.
Notice of allowance dated Sep. 25, 2015 for U.S. Appl. No. 13/894,288.
Notice of allowance dated Nov. 23, 2015 for U.S. Appl. No. 14/241,635.
Notice of allowance dated Dec. 4, 2009 for U.S. Appl. No. 11/241,799.
Office action dated Jan. 9, 2008 for U.S. Appl. No. 11/241,799.
Office action dated Feb. 23, 2016 for U.S. Appl. No. 14/979,148.
Office action dated Mar. 16, 2016 for U.S. Appl. No. 90/013,682.
Office action dated Mar. 30, 2009 for U.S. Appl. No. 11/241,799.
Office action dated May 30, 2007 for U.S. Appl. No. 11/241,799.
Office action dated Jun. 16, 2015 for U.S. Appl. No. 13/894,288.
Office action dated Jul. 30, 2015 for U.S. Appl. No. 14/241,635.
Office action dated Aug. 19, 2008 for U.S. Appl. No. 11/241,799.
Office action dated Nov. 1, 2012 for U.S. Appl. No. 12/703,096.
Palmisano, et al. In-cell indirect electrochemical halogenation of pyrimidine bases and their nucleosides to 5-haloderivatives. Tetrahedron Lett. 1992; 33(50): 7779-7782.
Pankiewiz, K. W. Fluorinated nucleosides. Carbohydr. Res. 2000; 327:87-105.
Paz, et al. A Systematic Profile of DNA Methylation in Human Cancer Cell Lines. Cancer Research. 2003; 63:1114-1121.
Piskala, et al. Direct synthesis of 5 azapyrimidine 2'-deoxyribonucleosides. Hydrolysis of 5-aza-2'-deoxycytidine. Nucleic Acids Res. 1978; 4:s109-s113.
Pliml, et al. Synthesis of a 2-deoxy-D-ribofuranosyl-5-azacytosine. Collect. Czech. Chem. Commun. 1964; 29:2576-2577.
Pompon, et al. Reversed-phase high-performance liquid chromatography of nucleoside analogues. Simultaneous analysis of anomeric D-xylo- and D-lyxofuranonucleosides and some other D-pentofuranonucleosides. J. Chromat. 1987; 388: 113-22.
Primeau, et al. Synergistic Antineoplastic Action of DNA Methylation Inhibitor 5-Aza-2'-Deoxycytidine and Histone Deacetylase Inhibitor Depsipeptide on Human Breast Carcinoma Cells. Int. J. Cancer. 2003; 103:177-184.
Santini, et al. Changes in DNA Methylation in Neoplasia: Pathophysiology and Therapeutic Implications. Annals of Internal Medicine. 2001; 134:573-586.
Schrump, et al. Phase 1 Study of Sequential Deoxyazacytidine/ Depsipeptide Infusion in Patients With Malignancies Involving Lungs or Pleura. Clinical Lung Cancer. 2002; 186-192.
Schwartz, et al. Six new saddle-shaped hosts based on fused dibenzofuran units. J. Am. Chem. Soc. 1992; 114:10775-10784.
Search report dated Feb. 4, 2015 for SG Application No. 2014013395.
Shaker, et al. Preclinical evaluation of antineoplastic activity of inhibitors of DNA methylation (50aza02'-deoxycytidine) and histone deacetylation (trichostatin A, depsipeptide) in combination against myeloid leukemic cells. Leukemia Research. 2003; 27:437-444.
Sheikhnejad, et al. Mechanism of inhibition of DNA (cytosine C5)-methyltransferases by oligodeoxyribonucleotides containing 5,6-dihydro-5-azacytosine. J Mol Biol. Feb. 5, 1999;285(5):2021-34.

Smiraglia, et al. The Study of Aberrant Methylation in Cancer via Restriction Landmark Genomic Scanning. Oncogene. 2002; 21:5414-5426.
Tsang, et al. Hydrophobic Cluster Formation Is Necessary for Dibenzofuran-Based Amino Acids to Function as β-Sheet Nucleators. J. Am. Chem. Soc. 1994; 116:3988-4005.
Von Hoff, et al. 5-Azacytidine. A New Anticancer Drug With Effectiveness in Acute Myelogenous Leukemia. Annals of Internal Medicine. 1976; 85(2): 237-45.
Wajed, et al. DNA Methylation: An Alternative Pathway to Cancer. Annals of Surgery 2001; 234(1):10-20.
Weiser, et al. Sequential 5-aza-2'-deoxycytidine-depsipeptide FR901228 treatment induces apoptosis preferentially in cancer cells and facilities their recognition by cytolytic T lymphocytes specific for NY-ESO-1. Journal of Immunotherapy. 2001; 24(2):151-161.
Written opinion dated Jul. 16, 2015 for SG Application No. 2014013395.
Xiong, et al. A. COBRA: a sensitive and quantitative DNA methylation assay. Nucleic Acids Res. 1997; 25:2532-2534.
Zhenodarova, et al. Nucleoside antimetabolites in the synthesis of the internucleotide bond catalyzed by ribonucleases. Nukleazy: Biol. Rol Prakt. Ispol'z. ( 1985 ), 25-8. Editor(s): Berdyshev, G. D.; Khursin, N. E. Publisher: Naukova Dumka, Kiev, USSR. Coden: 54IIAL, 1985 (in Russian with English).
Zhong, et al. Dinucleotide analogues as novel inhibitors of RNA-dependent RNA polymerase of hepatitis C Virus. Antimicrob Agents Chemother. Aug. 2003;47(8):2674-81.
Ansel, Howard C, et al. Pharmaceutical Dosage Forms and Drug Delivery Systems. Philadelphia, PA: Lippincott-Williams & Wilkins, 1999. Print.
Carducci M., et al. Phenylbutyrate (PB) for refractory solid tumors: Phase I clinical and pharmacologic evaluation of intravenous and oral PB. Anticancer Res., 17: 3972-3973, 1997.
Co-pending U.S. Appl. No. 12/498,223, filed Jul. 6, 2009.
Co-pending U.S. Appl. No. 15/200,086, filed Jul. 1, 2016.
Co-pending U.S. Appl. No. 90/013,682, filed Jan. 19, 2016.
Coral, et al., "Immunomodul a tory activity of SGI-118, a 5-aza-2'-deoxycytidine-containing demethylating dinucleotide", Cancer Immunology, Immunotherapy, Nov. 9, 2012, 1(62): 605-614.
Darkin-Rattray, et al. Apicidin: A novel antiprotozoal agent that inhibits parasite histone deacetylase. PNAS, 1996, 93: (23) 13143-13147.
Digiacomo, et al., Ipilimumab experience in heavily pretreated patients with melanoma in an expanded access program at the University Hospital of Siena (Italy), Cancer immunol immunotherapy, Apr. 2011, 60:467-77.
Topalian, et al.,Safety, Activity, and Immune Correlates of Anti-PD-1 Antibody in Cancer, N Engl J Med. Jun. 28, 2012, 366, 2443-2454.
Tsuji, et al. A new antifungal antibiotic, trichostatin. J Antibiot (Tokyo) Jan. 1976; 29(1): 1-6.
Glick et al. Hybrid Polar Histone Deacetylase Inhibitor Induces Apoptosis and CD95/CD95 Ligand Expression in Human Neuroblastoma.
Hodi, et al., Improved Survival with Ipilimumab in Patients with Metastatic Melanoma, N Engl J Med, Aug. 19, 2010, 363:711-23.
International search report and written opinion dated Sep. 16, 2016 for PCT Application No. PCT/US2016/040730.
International Search Report dated Aug. 7, 2014 for PCT US2014019137.
Iwai, et al., Involvement of PD-L1 on tumor cells in the escape from host immune system and tumor immunotherapy by PD-L1 blockade, Proc Natl Acad Sci USA, Sep. 17, 2002, 99: 12293-12297.
Kijima, et al. Trapoxin, an antitumor cyclic tetrapeptide, is an irreversible inhibitor of mammalian histone deacetylase. J Biol Chem. Oct. 25, 1993;268(30):22429-35.
Steinhagen, et al., TLR-based immune adjuvants, Vaccine, Elsevier Ltd, GB, Aug. 14, 2010, 29(17): 3341-3355.
Koblish, et al., Hydroxyamidine Inhibitors of Indoleamine-2, 3-dioxygenase Potently Suppress Systemic Tryptophan Catabolism and the Growth of IDO-Expressing Tumors, Molecular Cancer Therapeutics, Feb. 2, 2010, 9(2): 489-498.
Kwon, et al. Depudecin induces morphological reversion of transformed fibroblasts via the inhibition of histone deacetylase. Proc Natl Acad Sci U S A. Mar. 31, 1998;95(7):3356-61.

(56) References Cited

OTHER PUBLICATIONS

Leach, et al., Enhancement of Antitumor Immunity by CTLA-4 Blockade, Science 1996, 271:1734-1736.

Lieberman, et al. Pharmaceutical Dosage Forms, Tablets. New York: M. Dekker, 1980. Print.

Newmark, et al. Butyrate as a differentiating agent: pharmacokinetics, analogues and current status. Cancer Lett. Apr. 1, 1994;78(1-3):1-5.

"O'Day, et al. Targeting Cytotoxic T-Lymphocyte Antigen (CTLA-4), A Novel Strategy for the Treatment of Melanoma and Other Malignancies. Cancer, vol. 110 No. 12 pp. 2614-2627".

Sucher, et al., IDO-Mediated Tryptophan Degradation in the pathogenesis of Malignant Tumor Disease, International Journal of Tryptophan Research, 2010: 3, 113-120.

Yoshida, et al. Potent and specific inhibition of mammalian histone deacetylase both in vivo and in vitro by trichostatin A. J Biol Chem. Oct. 5, 1990;265(28):17174-9.

Remington, et al. Remington's Pharmaceutical Sciences. Easton, PA: Mack Pub., 1990. Print.

Remington, et al. Remington: The Science and Practice of Pharmacy. Easton, PA: Mack Pub., 1995. Print.

Saito, et al. A synthetic inhibitor of histone deacetylase, MS-27-275, with marked in vivo antitumor activity against human tumors. Proc Natl Acad Sci U S A. Apr. 13, 1999;96(8):4592-7.

Weber, et al., Immune Checkpoint Proteins: A New Therapeutic Paradigm for Cancer-Preclinical Background: CTLA-4 and PD-1 Blockade, Oct. 2010, 37:430-439.

Co-pending U.S. Appl. No. 15/879,802, filed Jan. 25, 2018.

Notice of allowance dated Dec. 14, 2017 for U.S. Appl. No. 15/174,386.

Office action dated Oct. 19, 2017 for U.S. Appl. No. 14/771,011.

Robert, et al. Ipilimumab plus dacarbazine for previously untreated metastatic melanoma. N Engl J Med. Jun. 30, 2011;364(26):2517-26.

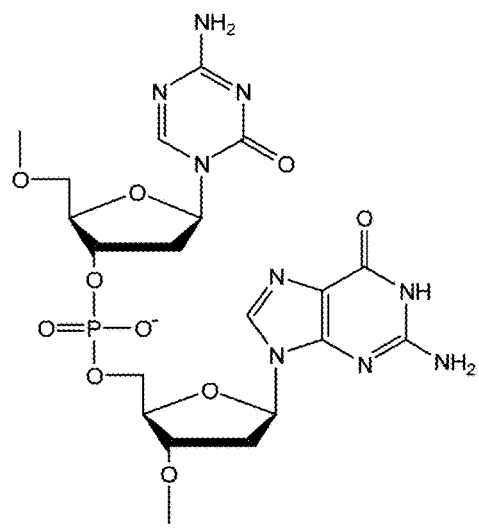
-DpG- Islet
with Natural PhosphodiesterBackbone
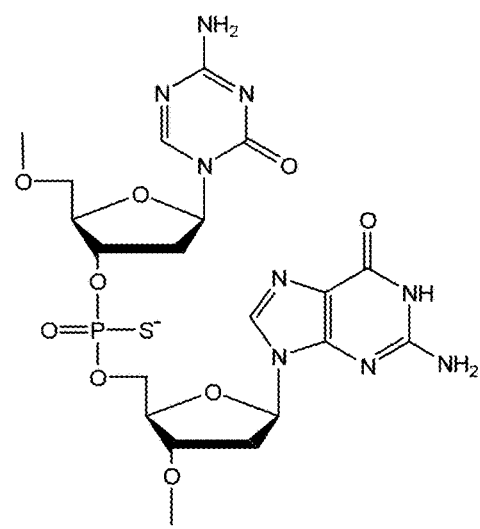
-DpG- Islet
with Phosphorothioate Backbone
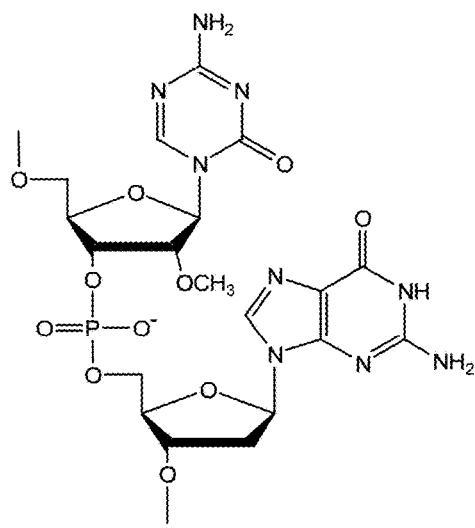
-DpG- Islet with 2'-Methoxy Ribose
PhosphodiesterBackbone
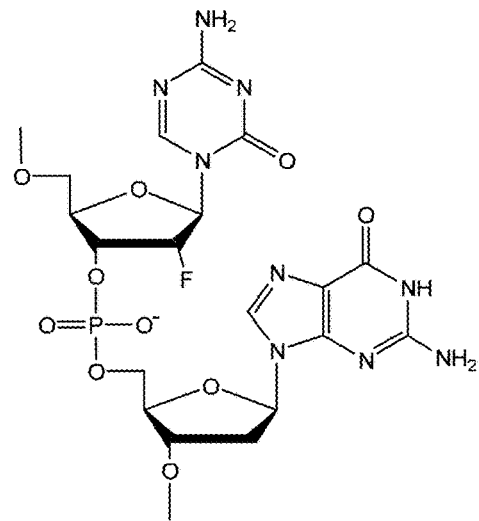
-DpG- Islet with 2'-Fluoro Ribose
PhosphodiesterBackbone
FIGURE 24A -DpnaG- Islet with Peptide Backbone SEQ ID NO:1      TpTpDpxGpDpxGpApA SEQ ID NO:2      TpGpxCpCpTpDpxGpT SEQ ID NO:3      ApGpGpxDpApCpApGpxDpA SEQ ID NO:4      GpTpGpxDpApGpxDpA SEQ ID NO:5      ApApDpxGpGpGpxDpGpGpxDpGpG SEQ ID NO:6      CpApDpxGpGpxDpGpxDpGpG

FIGURE 26

P15 PROMOTER REGION SEQUENCE (SEQ ID NO:7)

ttttcattcagtcaacttgcttcgcgaagctcacacatctgcctcgtgcaagattctcagtcattttac
ttagtcattggttctttccctatcaccattctttatgtcccctcaaagaaaaacattatcttccatttccttatcaact
ccaaacagcttcatttttctgacatatttactacctaagaaaatggctcaagaattgggtagactatcttgtcctaact
tttctgataagtttcagagaaactcaaggtcaaaacaagagcataagagtaaaggtagagaaattaagaaactgaagac
taggaaatgggggttgggatgggaaagaaaaagaaattgttataatgctacccggttcccttccctgtccaggtggattt
cagctctgttgaggctctgtcagtagatattcagccctaaccagcacttccatggtggtggcacttccactgcctttaa
aagaaagagcttttttaattctacagggatttggggatgaggagtcagagctaaggtatcctaaaaaaacatgtgaa
gactctcattttgcaatacacaagcaattgccctcctgttaagactttgtcttcctcagcactccgaaccaaaatgattc
tgtaaacaaaaattgttcacttttaggagaggtccacttatgcagttcctcaccaaagttttaggcaacaaatccataa
cttgcggttctcttcctatccaatgtagcatccgctgaaatgttttaaatattttaagtaataaatgttgattcaaactc
acctaggaagattaggaaggggaaaaaaagcacttggcatttaaatcttcagaagagaatttaatgacaggttcagcctg
tttaatgacaagcccagcaccacaccctctcttatgatgtttcattattactgcataaatttcctttattactcatgat
aaataaaaataagatacctgacaaagtgggtttaaataggtaagagtgcaaacaaagatttactgtacaaatatgatgaa
actgggatctcagattcttaaagtataatttttttttgtcttatgtgtgccaggttgccactctcaatctcgaactagttt
ttttctcttttaagggttgtatccataatgcaaaaatggaaagaattaaaaagcacacgcaaaacatgattctcggatt
tttctctatttttatggttgactaattcaaacagaaagacacatccaagagaaaattgctaagtttgatacaagttatga
aacttgtgaagcccaagtactgcctggggatgaatttaacttgtatgacaggtgcagagctgtcgctttcagacatctta
agaaagacggagttattttgaatgacttctctcggtcacaagggagccaccaacgtctccacagtgaaaccaactggct
ggctgaaggaacagaaatcctctgctccgcctactgggattaggagctgagggcagtggtgaacattcccaaaatatta
gccttggctttactggacatccagcgagcagtgcagccagcattcctggcggctccctggcccagtctctgcgcatgcg
tcctagcatctttgggcaggcttccccgccctcgtgacgcgtcggcccgggcctggcctccgcgatcacagcggacag
ggggcggagcctaagggggtggggagacgccggccccttggcccagctgaaaacggaattctttgccggctggctcccca
ctctgccagagcgaggcggggcagtgaggactccgcgacgcgtccgcaccctgcggccagagcggctttgagctcggctg
cgtccgcgctaggcgcttttcccagaagcaatccaggcgcgcccgctggttcttgagcgccaggaaaagcccggagcta
acgaccggccgctcggccactgcacgggcccaagccgcagaaggacgacgggagggtaatgaagctgagcccaggtct
cctaggaaggagagagtgcgccggagcagcgtggaaagaagggaagagtgtcgttaagtttacgccaacggtggatta
tccggccgctgcgcgtctgggggctgcggaatgcgcgaggagaacaagggcatgcccagtggggcggcagcg

```
SEQ ID NO:8      TTCGCGAA
SEQ ID NO:9      TGCCTCGT
SEQ ID NO:10     TGCCGGCT
SEQ ID NO:11     CGGCCCGG
SEQ ID NO:12     GCTCGGCT
```

FIGURE 27

P16 PROMOTER REGION SEQUENCE (SEQ ID NO:13)

cggagaggggagaacagacaacgggcggcggggagcagcatggagccggcggcggggagcagcatggag
ccttcggctgactggctggccacggccgcggcccggggtcgggtagaggaggtgcgggcgctgctggaggcgggggcgct
gcccaacgcaccgaatagttacggtcggaggccgatccaggtcatgatgatgggcagcgcccgagtggcggagctgctgc
tgctccacggcgcggagcccaactgcgccgacccgccactctcaccgacccgtgcacgacgctgcccgggagggcttc
ctggacacgctggtggtgctgcaccgggccggggcgcggctggacgtgcgcgatgcctgggccgtctgcccgtggacct
ggctgaggagctgggccatcgcgatgtcgcacggtacctgcgcgcggctgcgggggggcaccagaggcagtaaccatgccc
gcatagatgccgcggaaggtccctcagacatcccgattgaaagaaccagagaggctctgagaaacctcgggaaacttag
atcatcagtcaccgaaggtcctacagggccacaactgccccgccacaacccacccgctttcgtagttttcatttagaa
aatagagcttttaaaaatgtcctgccttttaacgtagatataagccttcccccactaccgtaaatgtccatttatatcat
tttttatatattcttataaaaatgtaaaaaagaaaaacaccgcttctgccttttcactgtgttggagttt
tctggagtgagcactcacgccctaagcgcacattcatgtgggcatttcttgcgagcctcgcagcctccggaagctgtcga
cttcatgacaagcattttgtgaactagggaagctcagggggttactggcttctcttgagtcacactgctagcaaatggc
agaaccaaagctcaaataaaataaaataattttcattcattcactc SEQ ID NO:14    AACGGGCGGCGG
SEQ ID NO:15    CACGGCGCGG
SEQ ID NO:16    CGGGCGGC
SEQ ID NO:17    AGCAGCAT
SEQ ID NO:18    GCGCCGAC

FIGURE 28

BRCA1 PROMOTER REGION SEQUENCE (SEQ ID NO:19)

ccacctaattgtactgaattgcaaattgatagttgttctagcagtgaagagataaagaaaaaaagtaca
accaaatgccagtcaggcacagcagaaacctacaactcatggaaggtaaagaacctgcaactggagccaagaagagtaac
aagccaaatgaacagacaagtaaaagacatgacagcgatactttcccagagctgaagttaacaaatgcacctggttctttt
tactaagtgttcaaataccagtgaacttaaagaatttgtcaatcctagcctccaagagaagaaaaagaagagaaactag
aaacagttagtgtctaataatgctgaagaccccaaagatctcatgttaagtggagaaagggttttgcaaactgaaagatc
tgtagagagtagcagtatttcattggtacctggtactgattatggcactcaggaaagtatctcgttactggaagttagca
ctctagggaaggcaaaaacagaaccaaataaatgtgtgagtcagtgtgcagcatttgaaaaccccaagggactaattcat
ggttgttccaaagataatagaaatgacacagaaggctttaagtatccattgggacatgaagttaaccacagtcgggaaac
aagcatagaaatggaagaa

```
SEQ ID NO:20    AGGCACAGCA
SEQ ID NO:21    GTGCAGCA
SEQ ID NO:22    CAGCGATA
SEQ ID NO:23    TAGCAGTG
SEQ ID NO:24    AGGCTTTA
```

FIGURE 29

OLIGONUCLEOTIDE ANALOGUES INCORPORATING 5-AZA-CYTOSINE THEREIN

PRIORITY

This application is a divisional of U.S. application Ser. No. 14/979,148, filed Dec. 22, 2015, which is a continuation of U.S. application Ser. No. 13/894,288, filed May 14, 2013, now U.S Pat. No. 9,358,248, which is a continuation of U.S. application Ser. No. 12/703,096, filed Feb. 9, 2010, now U.S. Pat. No. 8,461,123, which is a continuation of U.S. application Ser. No. 11/241,799, filed Sep. 29, 2005, now U.S. Pat. No. 7,700,567, each of which is incorporated herein by reference in its entirety.

SEQUENCE LISTING

The instant application contains a Sequence Listing which has been submitted via EFS-Web and is hereby incorporated by reference in its entirety. Said ASCII copy, created on Sep. 26, 2016 named 12636350401.txt and is 12,531 bytes in size.

BACKGROUND OF THE INVENTION

Field of the Invention

The present invention relates to design, synthesis and application of oligonucleotide analogues which are useful as therapeutics, diagnostics as well as research reagents. Oligonucleotide analogues are provided that incorporate an analogue of cytosine, 5-aza-cytosine, in the oligonucleotide sequence, e.g., in the form of 5-aza-2'-deoxycytidine or 5-aza-cytidine. Such analogues can be used for modulation of DNA methylation, especially for effective inhibition of methylation of cytosine at the C-5 position by more specifically targeting the CpG islets of the human genome. Methods for synthesizing these oligonucleotide analogues and for modulating C-5 cytosine methylation are provided. In particular, phosphoramidite building blocks and oligonucleotides containing decitabine (5-aza-2'-deoxycytidine; D), DpG-rich (Decitabine-phosphodiester linkage-Guanosine) islets and derivatives, are provided. Also provided are methods for preparing, formulating and administering these compounds or compositions as therapeutics to a host in need thereof.

Description of Related Art

Decitabine is currently being developed as a new pharmaceutical for the treatment of chronic myelogenous leukemia (CML), myelodysplastic syndrome (MDS), non-small cell lung (NSCL) cancer, sickle-cell anemia, and acute myelogenous leukemia (AML). Two isomeric forms of decitabine can be distinguished. The 3-anomer is the active form, which is shown in FIG. 1. Decitabine possesses multiple pharmacological characteristics. At the molecular level, it is incorporated into DNA during the S phase of cell cycle. At the cellular level, decitabine can induce cell differentiation and exert hematological toxicity. Despite having a short half-life in vivo, decitabine has an excellent tissue distribution.

One of the functions of decitabine is its ability to specifically and potently inhibit DNA methylation. DNA methylation is an epigenetic effect common to many systems. This modification involves the covalent modification of cytosine at the C-5 position (1a"). Methylation patterns are stably maintained at CpG dinucleotides by a family of DNA methyltransferases that recognize hemimethylated DNA after DNA replication. Inside the cell, decitabine is first converted into its active form, the phosphorylated 5-aza-deoxycytidine, by deoxycytidine kinase, which is primarily synthesized during the S phase of the cell cycle. The affinity of decitabine for the catalytical site of deoxycytidine kinase is similar to the natural substrate, deoxycytidine (Momparler et al. 1985 Mol. Pharmacol. 30:287-299). After conversion to its triphosphate form by deoxycytidine kinase, decitabine is incorporated into replicating DNA at a rate similar to that of the natural substrate, dCTP (Bouchard and Momparler 1983 Mol. Pharmacol. 24:109-114).

CpG-rich sequences of housekeeping genes are generally protected from methylation in normal cells. In cancerous cells, aberrant hypermethylation in promoter region CpG-islands of tumor suppressor genes is one of the most common events associated with progression of the tumorigenic phenotype. Each class of differentiated cells has its own distinct methylation pattern. Incorporation of decitabine into the DNA strand has a hypomethylation effect. After chromosomal duplication, in order to conserve this pattern of methylation, the 5-methylcytosine on the parental strand serves to direct methylation on the complementary daughter DNA strand. Substituting the carbon at the C-5 position of the cytosine for nitrogen interferes with this normal process of DNA methylation. The replacement of cytosine with decitabine at a specific site of methylation produces an irreversible inactivation of DNA methyltransferases. Decitabine behaves faithfully as a cytosine residue until DNA methyltransferase enzymes attempt to transfer a methyl group to the hemimethylated DNA strands of the daughter cells. At this step the DNA methyltransferase enzyme is covalently trapped by decitabine in the DNA and cannot further silence (methylate) additional cytosine residues (Juttermann et al. 1994 Proc. Natl. Acad. Sci. USA 91:11797-11801). This unique mechanism of action of decitabine allows genes silenced (that were once methylated) from previous rounds of cell division to be re-expressed. The active trap is present in the hemimethylated DNA up to 48 hours after decitabine treatment. After further DNA synthesis and cell cycle division, progeny strands from the hemimethylated DNA result in DNA strands that are completely unmethylated at these sites (Jones P. 2001 Nature 409: 141, 143-4). By specifically inhibiting DNA methyltransferases, the enzyme required for methylation, aberrant methylation of the tumor suppressor genes could be reversed.

Despite its proven antileukemic effects in CML, MDS, and AML, the potential application of decitabine has been hampered by delayed and prolonged myelosuppression. Lower doses of decitabine, given over a longer period of time, have minimized myelosuppression to manageable levels without compromising its ability to suppress cancer via its hypomethylation effect. At higher doses, the associated toxicity was prohibitive. However, treatment of hematologic and solid tumors at maximally tolerated doses of decitabine has been ineffective. The cause of myelosuppression is not clear. It is plausible that since decitabine is randomly and extensively incorporated into the DNA of S phase cells, including bone marrow cells that are involved in normal hematopoiesis, the severe DNA damage due to the instability of decitabine leads to necrosis. Since incorporation of decitabine is not restricted to only the CpG-rich sequences, the DNA can break, due to the instability of decitabine, and require repair at numerous sites outside of the CpG islands. Decitabine and azacitidine are unstable in aqueous media and undergo hydrolytic degradation. In acidic medium, decitabine is hydrolyzed at room temperature to 5-azacytosine and 2-deoxyribose. In neutral medium at room temperature, the opening of the triazine ring takes place at the 6-position to form the transient intermediate formyl derivative, which further degrades to the amidino-urea derivative and formic acid (Piskala, A.; Synackova, M.; Tomankova, H.; Fiedler, P.; Zizkowsky, V. *Nucleic Acids Res.* 1978, 4, s109-s-113.). This hydrolysis at the 6-position occurs in acidic and basic aqueous media at even faster rates.

In view of the chemical instability and toxicities associated with decitabine, there exists a need to develop not only more stable derivatives of decitabine but superior hypomethylating agents, where incorporation is localized to the CpG islands as much as possible or hypomethylation is achieved without significantly affecting the integrity of the DNA.

SUMMARY OF THE INVENTION

The present invention provides oligonucleotide analogues that incorporate 5-aza-cytosine in the oligonucleotide sequence, e.g., in the form of 5-aza-2'-deoxycytidine (decitabine) or 5-aza-cytidine.

In one aspect of the invention, an isolated or synthetic oligonucleotide analogue having 12 or less bases in length is provided, which comprises one or more 5-aza-cytosine residues in the sequence of the oligonucleotide analogue.

In an embodiment, the oligonucleotide analogue has a general formula:

-Z-L-G-, or -G-L-Z-, wherein Z is 5-aza-cytosine; G is guanine; and L is a chemical linker covalently linking Z and G. The oligonucleotide analogue optionally has more than 30%, 35%, or 40% guanine residues in the sequence of the oligonucleotide analogue.

In particular embodiments, the oligonucleotide analogue is selected from the group consisting of 5'-DpG-3', 5'-GpD-3', 5'-DpGpD-3', 5'-GpGpD-3', 5'-GpDpG-3', 5'-GpDpD-3', 5'-DpDpG-3', 5'-DpGpG-3', 5'-GpDpD-3', 5'-DpGpA-3', 5'-DpGpDpG-3', 5'-DpGpGpD-3', 5'-GpDpGpD-3', 5'-GpDpGpD-3', 5'-GpDpDpG-3', 5'-DpGpDpGpA-3', wherein D is decitabine; p is a phospholinker; A is 2'-deoxyadenosine, and G is 2'-deoxyguanosine.

In another aspect of the invention, an isolated or synthetic oligonucleotide analogue is provided which comprises, 2 or more copies of a dinucleotide analogue having the general formula:

-Z-L-G-, or -G-L-Z-, wherein Z is 5-aza-cytosine; G is guanine; and L is a chemical linker covalently linking Z and G.

Optionally, the oligonucleotide analogue comprises less than 10, 8, 6, or 4 copies of the dinucleotide analogue -Z-L-G-, or -G-L-Z-.

In particular embodiments, the oligonucleotide analogue comprises a segment selected from the group consisting of 5'-DpG-3', 5'-GpD-3', 5'-DpGpD-3', 5'-GpGpD-3', 5'-GpDpG-3', 5'-GpDpD-3', 5'-DpDpG-3', 5'-DpGpG-3', 5'-GpDpD-3', 5'-DpGpA-3', 5'-DpGpDpG-3', 5'-DpGpGpD-3', 5'-GpDpGpD-3', 5'-GpDpDpG-3', 5'-DpGpDpGpA-3', wherein D is decitabine; p is a phospholinker; A is 2'-deoxyadenosine, and G is 2'-deoxyguanosine.

In yet another aspect of the invention, an isolated or synthetic oligonucleotide analogue having at least 6 bases in length is provided, which comprises one or more 5-aza-cytosine residues in the sequence of the oligonucleotide analogue and has at least 75% sequence homology with a segment of a gene, preferably the 5'-untranslated region of a gene, such as the promoter of the gene.

In an embodiment, the oligonucleotide analogue has a general formula:

-Z-L-G-, or -G-L-Z-, wherein Z is 5-aza-cytosine; G is guanine; and L is a chemical linker covalently linking Z and G. The oligonucleotide analogue optionally has more than 30%, 35%, or 40% guanine residues in the sequence of the oligonucleotide analogue.

In particular embodiments, the oligonucleotide analogue comprises a segment selected from the group consisting of 5'-DpG-3', 5'-GpD-3', 5'-DpGpD-3', 5'-GpGpD-3', 5'-GpDpG-3', 5'-GpDpD-3', 5'-DpDpG-3', 5'-DpGpG-3', 5'-GpDpD-3', 5'-DpGpA-3', 5'-DpGpDpG-3', 5'-DpGpGpD-3', 5'-GpDpGpD-3', 5'-GpDpDpG-3', 5'-DpGpDpGpA-3', wherein D is decitabine; p is a phospholinker; A is 2'-deoxyadenosine, and G is 2'-deoxyguanosine.

In yet another aspect of the invention, an oligonucleotide analogue is provided that binds an allosteric site on DNA methyltransferases thereby inhibiting DNA methyltransferases.

In one embodiment, the oligonucleotide analogue has a sequence of
5'-CTGGATCCTTGCCCCGCCCCTTGAATTCCC-3' (SEQ ID NO:25);
5'-GGGAATTCAAATGACGTCAAAAGGATCCAG-3' (SEQ ID NO:26);
5'-CCTACCCACCCTGGATCCTTGCCCCGCCCCTT-GAATTCCCAACCCTCCAC-3' (SEQ ID NO:27);
5'-ATCCTTGCCCCGCCCCTTGAAT-3' (SEQ ID NO:28); or
5'-TTGCCCCGCCCCTT (SEQ ID NO:29), wherein at least one of the cytosine residues in SEQ ID NOs: 25-29 is substituted with 5-aza-cytosine.

For example, the oligonucleotide analogue may be
5'-CTGGATCCTTGCCCDGCCCCTTGAATTCCC-3' (SEQ ID NO:30), wherein one of the 14 cytosine residues in SEQ ID NO:25 at nucleotide position 15 is substituted with 5-aza-cytosine.

In yet another aspect of the invention, an oligonucleotide analogue is provided that is at least 6 nucleotide long, has at least one 5-aza-cytosine as a base residue and adopts a hairpin conformation at ambient temperature, such as 20-25° C., in aqueous solution, such as water, saline, or a buffer comprising 20 mM HEPES (pH 7), 12% glycero, 1 mM EDTA, 4 mM dithothreitol, 0.1% Nonidet P-40, and 3 mM $MgCl_2$.

In one embodiment, the oligonucleotide analogue has the following general secondary structure:

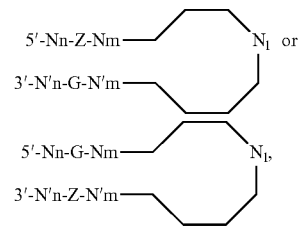

wherein N is any nucleotide; N' is a nucleotide complementary to N; Z is 5-aza-cytosine as a base residue; G is guanine as a base residue; 1, n, or m is an integer; nucleotide Nn, Nm, N'n, and N'm are positioned in the stem region of the hairpin; and $N_l$ is positioned in the loop region of the hairpin. Preferably, 1, n, or m is an integer greater than 2, 3, 4, or 5.

Optionally, 1 is 2, 3, 4, 5, or 6. Also optionally, if Nn, Nm, or N₁ has one or more cytosine residues, the cytosine residue is substituted with 5-aza-cytosine.

In a particular embodiment, the oligonucleotide analogue (SEQ ID NO:31) has the following hairpin conformation:

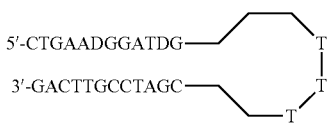

wherein D is decitabine, A is adenosine or 2'-deoxyadenosine, T is thymidine or 2'-deoxythymidine, and C at nucleotide position 21 is optionally substituted with 5-methyl-2'-deoxycytidine.

In any of above embodiments, the oligonucleotide analogue can be single-stranded or double-stranded. When the oligonucleotide analogue is double-stranded, the first strand is the oligonucleotide analogue, and the second strand may be an oligonucleotide with sequence complementary to that of the first strand without the cytosine residue being replaced with 5-aza-cytosine. For example, the first strand may be 5'-TTDGDGAA-3' (SEQ ID NO: 32) wherein D is decitabine; whereas the second strand may be 5'-TTCGCGAA-3' (SEQ ID NO: 33).

Optionally, when the second strand of oligonucleotide comprises one or more cytosine residues, and at least one of the cytosine residues is substituted with 5-methyl-cytosine.

Also optionally, when the first strand has a segment of 5'-Z-L-G-3', and the second strand comprises a segment of 3'-G-L-C'-5' that matches with the segment of 5'-Z-L-G-3' in the first strand, wherein Z is 5-aza-cytosine; G is guanine; L is a chemical linker covalently linking Z and G, or G and C'; and C' is 5-methyl-cytosine.

Also optionally, when the first strand has a segment of 5'-G-L-Z-3', and the second strand comprises a segment of 3'-C'-L-G-5' that matches with the segment of 5'-G-L-Z-3' in the first strand, wherein Z is 5-aza-cytosine; G is guanine; L is a chemical linker covalently linking Z and G, or G and C'; and C' is 5-methyl-cytosine.

The present invention also provides methods for synthesizing the oligonucleotide analogues and for modulating nucleic acid methylation. Also provided are phosphoramidite building blocks for synthesizing the oligonucleotide analogues, formulating and administering these compounds or compositions to treat conditions, such as cancer and hematological disorders.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 24A depicts -DpG- islets with natural phosphodiester backbone or modified backbones.

FIG. 26 lists examples of inventive oligonucleotide analogues specifically targeting the promoter region of P15, BRAC1 or P16, where D can be decitabine or decitabine analogues and px=p for natural phosphate linkage, px=ps for phosphorothioate linkage, px=bp for boranophospate, px=mp for methylphosphonate linkage.

FIG. 27 lists the sequence of P15 promoter region and examples of segments thereof, based on which DpG and GpD rich oligonucleotide analogues can be made.

FIG. 28 lists the sequence of P16 promoter region and examples of segments thereof, based on which DpG and GpD rich oligonucleotide analogues can be made.

FIG. 29 lists the sequence of BRCA1 promoter region and examples of segments thereof, based on which DpG and GpD rich oligonucleotide analogues can be made.

DETAILED DESCRIPTION OF THE INVENTION

Figure 1:
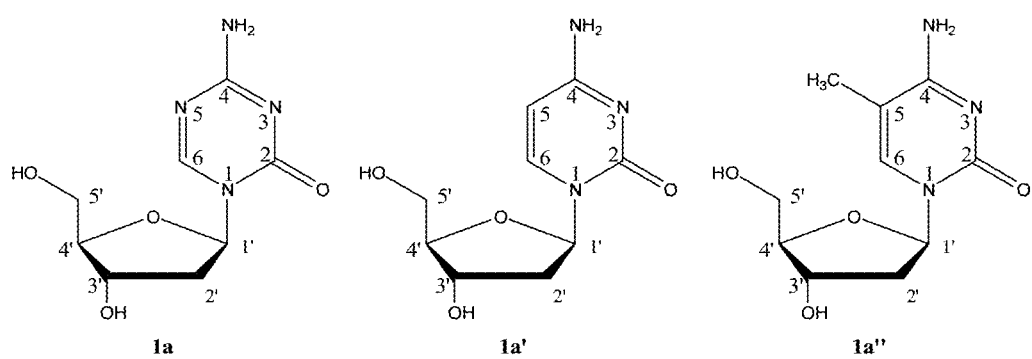
FIG. 1 shows structure of decitabine, D (1a), cytosine, C (1a'), and 5-methyl cytosine, mC (1a").

The present invention provides oligonucleotide analogues which incorporate an analogue of cytosine, 5-aza-cytosine, in the oligonucleotide sequence, e.g., in the form of 5-aza-2'-deoxycytidine (also known as decitabine) or 5-aza-cytidine (5-azaC). It is believed that incorporation of one or more residues of 5-aza-cytosine into an oligonucleotide would have a DNA hypomethylation effect as replacement of cytosine with decitabine at a specific site of methylation produces an irreversible inactivation of DNA methyltransferase. Preferably decitabine is incorporated into the oligonucleotide 5'-adjacent to a guanine residue to form a DpG islet in order to more specifically target the CpG islets of the human genome.

The invention is aimed to overcome potential toxicities associated with conventional hypomethylating agents such as decitabine and 5-aza-cytidine. Compared to the free nucleoside forms, which are randomly and extensively incorporated into the whole genome, the inventive compounds could act as primers and are incorporated mainly into the CpG-rich islands of the DNA during replication. Preferably, the inventive compounds act as primers and are incorporated specifically into the CpG-rich islands of the promoters of therapeutically or diagnostically important genes, such as the tumor suppressor genes. The inventive compounds could form temporarily hemimethylated stands with the parental strand and function as the active trap of DNA methyltransferases without being incorporated. The inventive compounds may also directly occupy and trap DNA methyltransferases without being incorporated into the genome. Since DNA modification is localized to the CpG-rich islands in the promoter regions of tumor suppressor genes, when the inventive compounds are incorporated, the active trap is optimally placed and overall stability of the greater genome remains uncompromised.

By modulating DNA methylation, the inventive compounds can be used as therapeutics, diagnostics as well as research reagents, especially in the areas of cancer and hematological disorders. Aberrant transcriptional silencing of a number of genes, such as tumor suppressor genes, is directly related to pathogenesis of cancer and other diseases. Due to methylation of cancer-related genes, expression of these genes is suppressed or completely silenced. Meanwhile, expression of these genes is required for induction of growth arrest, differentiation, and/or apoptotic cell death of transformed cells. Inaction of these genes in the transformed cells leads to uncontrolled proliferation of these cells, which eventually results in cancer. Thus, by using the inventive compounds to actively trap DNA methyltransferases directly and without being incorporated into the genome or incorporated into the CpG-rich islands of these genes, transcription of the genes can be reactivated through inhibition of methylation of the promoters, thereby resulting suppression of cancer cell proliferation.

The compounds of the present invention can also be useful for research and diagnostics, because some embodiments of the inventive compounds can hybridize to a 5'-untranslated region or promoter sequence of a gene, enabling sandwich and other assays to easily be constructed to exploit this fact. Hybridization of the oligonucleotide analogues of the invention with the promoter sequence can be detected by means known in the art. Such means may include conjugation or non-covalently binding of an enzyme to the oligonucleotide analogue, radiolabelling of the oligonucleotide analogue or any other suitable detection means. Kits using such detection means for modulating activity of the promoter of the gene in a sample may also be prepared.

The present invention also provides methods for synthesizing these oligonucleotide analogues and for modulating C-5 cytosine methylation. In particular, phosphoramidite building blocks and oligonucleotides containing decitabine (5-aza-2'-deoxycytidine; D), DpG-rich (Decitabine-phosphodiester linkage-Guanosine) islets and derivative, are provided. Also provided are methods for preparing, formulating and administering these compounds or compositions as therapeutics to a host in need thereof. The inventive compounds, methods of synthesis, formulation of pharmaceutical compositions, preparation of vessels and kits, and use of the compounds or compositions for treating diseases or conditions are described in detail below.

1. Oligonucleotide Analogues of the Present Invention

In general the oligonucleotide analogue of the present invention has one or more residues of 5-aza-cytosine (hereinafter abbreviated as "Z") incorporated into an oligonucleotide sequence.

In one aspect of the invention, an isolated or synthetic oligonucleotide analogue having 12 or less bases in length is provided, which comprises one or more 5-aza-cytosine residues in the sequence of the oligonucleotide analogue.

In an embodiment, the oligonucleotide analogue has a general formula:

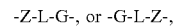

-Z-L-G-, or -G-L-Z-, wherein Z is 5-aza-cytosine; G is guanine; and L is a chemical linker covalently linking Z and G. The oligonucleotide analogue optionally has more than 30%, 35%, or 40% guanine residues in the sequence of the oligonucleotide analogue.

In particular embodiments, the oligonucleotide analogue is selected from the group consisting of 5'-DpG-3', 5'-GpD-3', 5'-DpGpD-3', 5'-GpDpD-3', 5'-GpDpG-3', 5'-GpDpD-3', 5'-DpDpG-3', 5'-DpGpG-3', 5'-GpDpD-3', 5'-DpGpA-3', 5'-DpGpDpG-3', 5'-DpGpGpD-3', 5'-GpDpGpD-3', 5'-GpDpDpG-3', 5'-DpGpDpGpA-3', wherein D is decitabine; p is a phospholinker; A is 2'-deoxyadenosine, and G is 2'-deoxyguanosine.

In another aspect of the invention, an isolated or synthetic oligonucleotide analogue is provided which comprises, 2 or more copies of a dinucleotide analogue having the general formula:

-Z-L-G-, or -G-L-Z-, wherein Z is 5-aza-cytosine; G is guanine; and L is a chemical linker covalently linking Z and G.

Optionally, the oligonucleotide analogue comprises less than 10, 8, 6, or 4 copies of the dinucleotide analogue -Z-L-G-, or -G-L-Z-.

In particular embodiments, the oligonucleotide analogue comprises a segment selected from the group consisting of 5'-DpG-3', 5'-GpD-3', 5'-DpGpD-3', 5'-GpGpD-3', 5'-GpDpG-3', 5'-GpDpD-3', 5'-DpDpG-3', 5'-DpGpG-3', 5'-GpDpD-3', 5'-DpGpA-3', 5'-DpGpDpG-3', 5'-DpGpGpD-3', 5'-GpDpGpD-3', 5'-GpDpDpG-3', 5'-DpGpDpGpA-3', wherein D is decitabine; p is a phospholinker; A is 2'-deoxyadenosine, and G is 2'-deoxyguanosine.

In yet another aspect of the invention, an isolated or synthetic oligonucleotide analogue having at least 6 bases in length is provided, which comprises one or more 5-aza-cytosine residues in the sequence of the oligonucleotide analogue and has at least 75% sequence homology with a segment of a gene, preferably the 5'-untranslated region of a gene, such as the promoter of the gene.

In an embodiment, the oligonucleotide analogue has a general formula:

-Z-L-G-, or -G-L-Z-, wherein Z is 5-aza-cytosine; G is guanine; and L is a chemical linker covalently linking Z and G. The oligonucleotide analogue optionally has more than 30%, 35%, or 40% guanine residues in the sequence of the oligonucleotide analogue.

In particular embodiments, the oligonucleotide analogue comprises a segment selected from the group consisting of 5'-DpG-3', 5'-GpD-3', 5'-DpGpD-3', 5'-GpGpD-3', 5'-GpDpG-3', 5'-GpDpD-3', 5'-DpDpG-3', 5'-DpGpG-3', 5'-GpDpD-3', 5'-DpGpA-3', 5'-DpGpDpG-3', 5'-DpGpGpD-3', 5'-GpDpGpD-3', 5'-GpDpDpG-3', 5'-DpGpDpGpA-3', wherein D is decitabine; p is a phospholinker; A is 2'-deoxyadenosine, and G is 2'-deoxyguanosine.

The gene is preferably a mammalian gene, and more preferably a human gene, and most preferably a human tumor suppressor gene. Examples of the human gene include, but are not limited to, VHL (the Von Hippon Landau gene involved in Renal Cell Carcinoma); P16/INK4A (involved in lymphoma); E-cadherin (involved in metastasis of breast, thyroid, gastric cancer); hMLH1 (involved in DNA repair in colon, gastric, and endometrial cancer); BRCA1 (involved in DNA repair in breast and ovarian cancer); LKB1 (involved in colon and breast cancer); P15/INK4B (involved in leukemia such as AML and ALL); ER (estrogen receptor, involved in breast, colon cancer and leukemia); O6-MGMT (involved in DNA repair in brain, colon, lung cancer and lymphoma); GST-pi (involved in breast, prostate, and renal cancer); TIMP-3 (tissue metalloprotease, involved in colon, renal, and brain cancer metastasis); DAPK1 (DAP kinase, involved in apoptosis of B-cell lymphoma cells); P73 (involved in apoptosis of lymphomas cells); AR (androgen receptor, involved in prostate cancer); RAR-beta (retinoic acid receptor-beta, involved in prostate cancer); Endothelin-B receptor (involved in prostate cancer); Rb (involved in cell cycle regulation of retinoblastoma); P14ARF (involved in cell cycle regulation); RASSF1 (involved in signal transduction); APC (involved in signal transduction); Caspase-8 (involved in apoptosis); TERT (involved in senescence); TERC (involved in senescence); TMS-1 (involved in apoptosis); SOCS-1 (involved in growth factor response of hepatocarcinoma); PITX2 (hepatocarcinoma breast cancer); MINT1; MINT2; GPR37; SDC4; MYOD1; MDR1; THBS1; PTC1; and pMDR1, as described in Santini et al. (2001) Ann. of Intern. Med. 134:573-586, which is herein incorporated by reference in its entirety. Nucleotide sequences of these genes can be retrieved from the website of the National Center for Biotechnology Information (NCBI).

As examples, the promoter sequences of the tumor suppressor genes, p15, p16, and BRCA1, are shown in FIGS. 27, 28, and 29, respectively. Examples of oligonucleotide analogues with at least 75% sequence homology with a segment of p15, p16, and BRCA1 are shown in FIGS. 27, 28, and 29, respectively.

It is appreciated by skilled artisans in the field of nucleic acids that the higher degree of sequence homology of a tester polynucleotide with its target polynucleotide, the higher stringency of the condition which the tester polynucleotide can remain hybridized to the target polynucleotide. Thus, the oligonucleotide analogues of the present invention that are designed to target a specific gene are those oligonucleotide analogues that hybridize to the target gene under very low to very high stringency conditions.

For oligonucleotide analogues of at least about 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures. The carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For shorter oligonucleotide analogues which are about 50 nucleotides to about 100 nucleotides in length, stringency conditions are defined as prehybridization, hybridization, and washing post-hybridization at 5° C. to 10° C. below the calculated $T_m$, using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures. The carrier material is washed once in 6×SCC plus 0.1% SDS for 15 minutes and twice each for 15 minutes using 6×SSC at 5° C. to 10° C. below the calculated T.

Another non-limiting examples of high stringency conditions include a hybridization solution containing, e.g., about 5×SSC, 0.5% SDS, 100 µg/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Yet another non-limiting example of high stringency conditions includes a final wash at 65° C. in aqueous buffer containing 30 mM NaCl and 0.5% SDS. Another example of high stringent conditions is hybridization in 7% SDS, 0.5 M NaPO$_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

In a preferred embodiment, the oligonucleotide analogue is capable of hybridizing with the target gene under low stringency conditions. In a more preferred embodiment, the oligonucleotide analogue is capable of hybridizing with the target gene under medium stringency conditions. In a most preferred embodiment, the oligonucleotide analogue is capable of hybridizing with the target gene under high stringency conditions.

In yet another aspect of the invention, an oligonucleotide analogue is provided that binds an allosteric site on DNA methyltransferase thereby inhibiting DNA methyltransferase. The inhibition of DNA methyltransferase prevents the methylation of DNA thereby treating the disorder associated with aberrant DNA methylation, such as cancer and hematological disorders.

In one embodiment, the oligonucleotide analogue has a sequence of

5'-CTGGATCCTTGCCCCGCCCCTTGAATTCCC-3' (SEQ ID NO:25);

5'-GGGAATTCAAATGACGTCAAAAGGATCCAG-3' (SEQ ID NO:26);

5'-CCTACCCACCCTGGATCCTTGCCCCGCCCTT-GAATTCCCAACCCTCCAC-3' (SEQ ID NO:27);

5'-ATCCTTGCCCCGCCCCTTGAAT-3' (SEQ ID NO:28); or

5'-TTGCCCCGCCCCTT (SEQ ID NO:29), wherein at least one of the cytosine residues in SEQ ID NOs: 25-28 is substituted with 5-aza-cytosine. For example, the oligonucleotide analogue may be 5'-CTGGATCCTTGCCCDGCCCCTTGAATTCCC-3' (SEQ ID NO:30) wherein one of the 14 cytosine residues in SEQ ID NO:25 at nucleotide position 15 is substituted with 5-aza-cytosine. Other examples of oligonucleotides that bind to DNA methyltransferase can be modified according to the present invention by substituting at least one of the cytosine residues can be found in WO 99/12027, which is herein incorporated by reference in its entirety. The assays for testing the activity of the oligonucleotide analogues of the present invention in binding and inhibiting activity of DNA methyltransferase can also be found in WO 99/12027.

In yet another aspect of the invention, an oligonucleotide analogue is provided that is at least 6 nucleotide long, has at least one 5-aza-cytosine as a base residue and adopts a hairpin conformation at ambient temperature, such as 20-25° C., in aqueous solution, such as water, saline, or a buffer comprising 20 mM HEPES (pH 7), 12% glycero, 1 mM EDTA, 4 mM dithothreitol, 0.1% Nonidet P-40, and 3 mM MgCl$_2$. It is believed that by adopting a hairpin conformation, the oligonucleotide analogue better mimics the double-stranded DNA substrate for DNA methyltransferase than a single-stranded oligonucleotide, thus inhibiting the activity of DNA methyltransferase more effectively.

In one embodiment, the oligonucleotide analogue has the following general secondary structure:

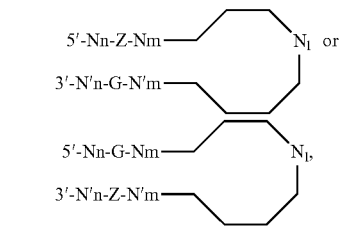

wherein N is any nucleotide; N' is a nucleotide complementary to N; Z is 5-aza-cytosine as a base residue; G is guanine as a base residue; 1, n, or m is an integer; nucleotide Nn, Nm, N'n, and N'm are positioned in the stem region of the hairpin; and $N_1$ is positioned in the loop region of the hairpin. Preferably, 1, n, or m is an integer greater than 2, 3, 4, or 5. Optionally, 1 is 2, 3, 4, 5, or 6. Also optionally, if Nn, Nm, or $N_1$ has one or more cytosine residues, the cytosine residue is substituted with 5-aza-cytosine.

In a particular embodiment, the oligonucleotide analogue has the following general secondary structure:

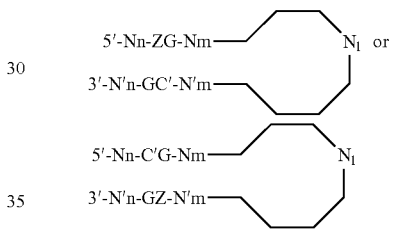

wherein C' is 5-methyl-cytidine.

In another particular embodiment, the oligonucleotide analogue (SEQ ID NO:31) has the following hairpin conformation:

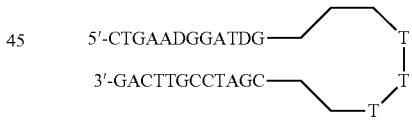

wherein D is decitabine A is adenosine or 2'-deoxyadenosine, T is thymidine or 2'-deoxythymidine, and C at nucleotide position 21 is optionally substituted with 5-methyl-2'-deoxycytidine.

In any of above embodiments, the oligonucleotide analogue can be single-stranded or double-stranded. When the oligonucleotide analogue is double-stranded, the first strand is the oligonucleotide analogue, and the second strand may be an oligonucleotide with sequence complementary to that of the first strand without the cytosine residue being replaced with 5-aza-cytosine. For example, the first strand may be 5'-TTDGDGAA-3' (SEQ ID NO: 32) wherein D is decitabine; whereas the second strand may be 5'-TTCGCGAA-3' (SEQ ID NO: 33). Optionally, at least one of the cytosine residues in either the first or second strand may be substituted with 5-methyl-cytosine.

Figure 24B:
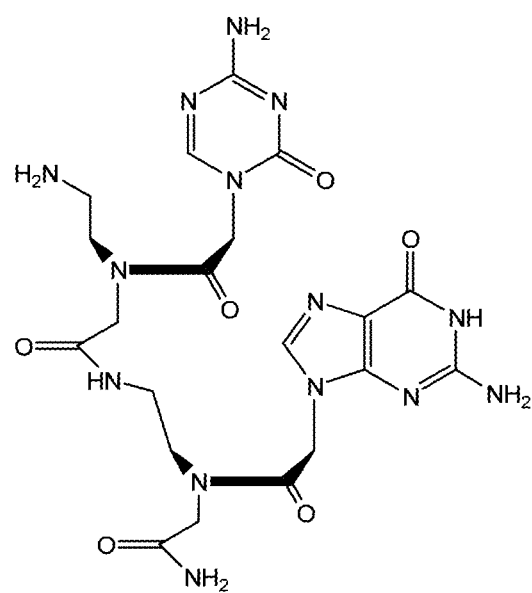
FIG. 24B depicts a -DpG- islet peptide backbone.

In any of above embodiments, the linker between Z and G residues or between any two of the base residues in the oligonucleotide analogue is preferably a sugar phosphorodiester linkage. Preferably the linker is a phosphorodiester linkage via 2'-deoxyribose or ribose, as in the natural sugar phosphorodiester backbone in DNA and RNA, respectively. Optionally, to enhance the resistance to nuclease degradation in vivo, the natural phosphorodiester linker —O—P(=O)(O$^-$)—O—CH$_2$— can be modified to be a phosphorothioate linker —O—P(=O)(S$^-$)—O—CH$_2$—, bornophosphate or methylphosphonate linker; the 2'-hydroxyl group of ribose can be modified to be a 2'-methoxy group, 2'-methoxyethyl group, or 2'-fluoro group. Examples of such oligonucleotide analogues with unnatural backbones are shown FIG. 24A where decitabine is linked to guanosine through ribose phosphate backbone. Also optionally, the natural sugar phosphorodiester backbone can be replaced with a protein nucleotide (PNA) backbone where the backbone is made from repeating N-(2-aminoethyl)-glycine units linked by peptide bonds. An example of such an oligonucleotide analogue with PNA backbone is shown in FIG. 24B where 5-aza-cytosine is linked to guanine via a PNA backbone. Other types of linkers for oligonucleotides designed to be more resistant to nuclease degradation than the natural are described U.S. Pat. Nos. 6,900,540 and 6,900,301, which are herein incorporated by reference.

The oligonucleotide analogues of the present invention may be ones isolated from biological sources, such as tissues, cells and body fluid, and preferably purified to a substantial degree of purity, more preferably of at least 80% purity, and most preferably of at least 95% of purity. The oligonucleotide analogues may also be synthetic ones that are non-naturally occurring oligonucleotide comprising a 5-aza-cytidine, e.g., chemically or enzymatically synthesized in vitro.

The oligonucleotide analogues of the present invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotide analogues of the invention may be prepared by forming one or more ester bond with any of the hydroxyl groups in the sugar ring using an organic compound containing a carboxyl group, or as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," J. of Pharma Sci., 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotide analogues of the present invention, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The invention also embraces isolated compounds. An isolated compound refers to a compound which represents at least 10%, preferably 20%, more preferably 50% and most preferably 80% of the compound present in the mixture, and exhibits a detectable (i.e. statistically significant) inhibitory activity of DNA methylation when tested in biological assays such as the combined bisulfite restriction analysis or COBRA (Xiong, Z.; Laird, P. W. Nucleic Acids Res. 1997, 25, 2532-2534) and radiolabeled methyl incorporation assay (Francis, K. T.; Thompson, R. W.; Krumdieck, C. L. Am. J. Clin. Nutr. 1977, 30, 2028-2032).

2. Pharmaceutical Formulations of the Present Invention

According to the present invention, the oligonucleotide analogues or compounds of the present invention can be formulated into pharmaceutically acceptable compositions for treating various diseases and conditions.

The pharmaceutically-acceptable compositions of the present invention comprise one or more compounds of the invention in association with one or more nontoxic, pharmaceutically-acceptable carriers and/or diluents and/or adjuvants and/or excipients, collectively referred to herein as "carrier" materials, and if desired other active ingredients.

The compounds of the present invention are administered by any route, preferably in the form of a pharmaceutical composition adapted to such a route, as illustrated below and are dependent on the condition being treated. The compounds and compositions can be, for example, administered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by a catheter or stent), subcutaneously, intraadiposally, intraarticularly, or intrathecally.

The pharmaceutical formulation may optionally further include an excipient added in an amount sufficient to enhance the stability of the composition, maintain the product in solution, or prevent side effects (e.g., potential ulceration, vascular irritation or extravasation) associated with the administration of the inventive formulation. Examples of excipients include, but are not limited to, mannitol, sorbitol, lactose, dextrox, cyclodextrin such as, α-, β-, and γ-cyclodextrin, and modified, amorphous cyclodextrin such as hydroxypropyl-, hydroxyethyl-, glucosyl-, maltosyl-, maltotriosyl-, carboxyamidomethyl-, carboxymethyl-, sulfobutylether-, and diethylamino-substituted α, β-, and γ-cyclodextrin. Cyclodextrins such as Encapsin® from Janssen Pharmaceuticals or equivalent may be used for this purpose.

For oral administration, the pharmaceutical compositions can be in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For topical use the compounds of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compounds of the present invention can be in powder form for reconstitution in the appropriate pharmaceutically acceptable carrier at the time of delivery.

The pharmaceutical compositions can be administered via injection. Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

The oligonucleotide analogues of the present invention may be prepared and formulated as emulsions. Emulsions are typically heterogenous systems of one liquid dispersed in another in the form of droplets usually exceeding 0.1 μm in diameter. (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the oligonucleotide analogues are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Besides microemulsions there are many organized surfactant structures that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Thou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoyl-phosphatidylcholine are disclosed in WO 97/13499 (Lim et al.).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{12}15G$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

In a particular embodiment, the compounds of the present invention can be formulated into a pharmaceutically acceptable composition comprising the compound solvated in non-aqueous solvent that includes glycerin, propylene glycol, polyethylene glycol, or combinations thereof. It is believed that the compounds will be stable in such pharmaceutical formulations so that the pharmaceutical formulations may be stored for a prolonged period of time prior to use.

In current clinical treatment with decitabine, to minimize drug decomposition decitabine is supplied as lyophilized powder and reconstituted in a cold aqueous solution containing water in at least 40% vol of the solvent, such as WFI, and diluted in cold infusion fluids prior to administration. Such a formulation and treatment regimen suffers from a few drawbacks. First, refrigeration of decitabine in cold solution becomes essential, which is burdensome in handling and economically less desirable than a formulation that can sustain storage at higher temperatures. Second, due to rapid decomposition of decitabine in aqueous solution, the reconstituted decitabine solution may only be infused to a patient for a maximum of 3 hr if the solution has been stored in the refrigerator for less than 7 hr. In addition, infusion of cold fluid can cause great discomfort and pain to the patient, which induces the patient's resistance to such a regimen.

By modifying the triazine ring and/or the ribose ring of decitabine and by formulating the compound with non-aqueous solvent, the pharmaceutical formulations can circumvent the above-listed problems associated with the current clinical treatment with decitabine. These formulations of the inventive compounds are believed to be more chemically stable than decitabine formulated in aqueous solutions containing water in at least 40% vol. of the solvent.

In a preferred embodiment, the inventive formulation contains less than 40% water in the solvent, optionally less than 20% water in the solvent, optionally less than 10% water in the solvent, or optionally less than 1% water in the solvent. In one variation, the pharmaceutical formulation is stored in a substantially anhydrous form. Optionally, a drying agent may be added to the pharmaceutical formulation to absorb water.

Owing to the enhanced stability, the inventive formulation may be stored and transported at ambient temperature, thereby significantly reducing the cost of handling the drug. Further, the inventive formulation may be conveniently stored for a long time before being administered to the patient. In addition, the inventive formulation may be diluted with regular infusion fluid (without chilling) and administered to a patient at room temperature, thereby avoiding causing patients' discomfort associated with infusion of cold fluid.

In another embodiment, the inventive compound is dissolved in glycerin at different concentrations. For example, the formulation may optionally comprise between 0.1 and 200; between 1 and 100; between 1 and 50; between 2 and 50; between 2 and 100; between 5 and 100; between 10 and 100 or between 20 and 100 mg inventive compound per ml of glycerin. Specific examples of the inventive compound per glycerin concentrations include but are not limited to 2, 5, 10, 20, 22, 25, 30, 40 and 50 mg/ml.

Different grades of glycerin (synonyms: 1,2,3-propanetriol; glycerol; glycol alcohol; glycerol anhydrous) may be used to prepare the formulations. Preferably, glycerin with chemical purity higher than 90% is used to prepare the formulations.

In another embodiment, the inventive compound is dissolved in propylene glycol at different concentrations. For example, the formulation may optionally comprise between 0.1 and 200; between 0.1 and 100; between 0.1 and 50; between 2 and 50; between 2 and 100; between 5 and 100; between 10 and 100 or between 20 and 100 mg inventive compound per ml of propylene glycol. Specific examples of decitabine per propylene glycol concentrations include but are not limited to 2, 5, 10, 20, 22, 25, 30, 40 and 50 mg/ml.

In yet another embodiment, the inventive compound is dissolved in a solvent combining glycerin and propylene glycol at different concentrations. The concentration of propylene glycol in the solvent is between 0.1-99.9%, optionally between 1-90%, between 10-80%, or between 50-70%.

In yet another embodiment, the inventive compound is dissolved at different concentrations in a solvent combining glycerin and polyethylene glycol (PEG) such as PEG300, PEG400 and PEG1000. The concentration of polyethylene glycol in the solvent is between 0.1-99.9%, optionally between 1-90%, between 10-80%, or between 50-70%.

In yet another embodiment, the inventive compound is dissolved at different concentrations in a solvent combining propylene glycol, polyethylene glycol and glycerin. The concentration of propylene glycol in the solvent is between 0.1-99.9%, optionally between 1-90%, between 10-60%, or between 20-40%; and the concentration of polyethylene glycol in the solvent is between 0.1-99.9%, optionally between 1-90%, between 10-80%, between 50-70%.

It is believed and experimentally proven that addition of propylene glycol can further improve chemical stability, reduce viscosity of the formulations and facilitate dissolution of the inventive compound in the solvent.

The pharmaceutical formulation may further comprise an acidifying agent added to the formulation in a proportion such that the formulation has a resulting pH between about 4 and 8. The acidifying agent may be an organic acid. Examples of organic acid include, but are not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

It is believed that adding an acidifying agent to the formulation to maintain a relatively neutral pH (e.g., within pH 4-8) facilitates ready dissolution of the inventive compound in the solvent and enhances long-term stability of the formulation. In alkaline solution, there is a rapid reversible decomposition of decitabine to N-(formylamidino)-N'-β-D-2-deoxyribofuranosylurea, which decomposes irreversibly to form 1-β-D-2'-deoxyribofuranosyl-3-guanylurea. The first stage of the hydrolytic degradation involves the formation of N-amidinium-N'-(2-deoxy-β-D-erythropentofuranosyeurea formate (AUF). The second phase of the degradation at an elevated temperature involves formation of guanidine. In acidic solution, N-(formylamidino)-N'-β-D-2-deoxyribofuranosylurea and some unidentified compounds are formed. In strongly acidic solution (at pH<2.2) 5-azacytosine is produced. Thus, maintaining a relative neutral pH may be advantageous for the formulation comprising the analogs and derivatives of decitabine.

In a variation, the acidifying agent is ascorbic acid at a concentration of 0.01-0.2 mg/ml of the solvent, optionally 0.04-0.1 mg/ml or 0.03-0.07 mg/ml of the solvent.

The pH of the pharmaceutical formulation may be adjusted to be between pH 4 and pH 8, preferably between pH 5 and pH 7, and more preferably between pH 5.5 and pH 6.8.

The pharmaceutical formulation is preferably at least 80%, 90%, 95% or more stable upon storage at 25° C. for 7, 14, 21, 28 or more days. The pharmaceutical formulation is also preferably at least 80%, 90%, 95% or more stable upon storage at 40° C. for 7, 14, 21, 28 or more days.

In one embodiment, the pharmaceutical formulation of the present invention is prepared by taking glycerin and dissolving the inventive compound in the glycerin. This may be done, for example, by adding the inventive compound to the glycerin or by adding the glycerin to decitabine. By their admixture, the pharmaceutical formulation is formed.

Optionally, the method further comprises additional steps to increase the rate at which the inventive compound is solvated by the glycerin. Examples of additional steps that may be performed include, but are nor limited to, agitation, heating, extension of solvation period, and application of micronized inventive compound and the combinations thereof.

In one variation, agitation is applied. Examples of agitation include but are nor limited to, mechanical agitation, sonication, conventional mixing, conventional stirring and the combinations thereof. For example, mechanical agitation of the formulations may be performed according to manufacturer's protocols by Silverson homogenizer manufactured by Silverson Machines Inc., (East Longmeadow, Mass.).

In another variation, heat may be applied. Optionally, the formulations may be heated in a water bath. Preferably, the temperature of the heated formulations may be less than 70° C., more preferably, between 25° C. and 40° C. As an example, the formulation may be heated to 37° C.

In yet another variation, the inventive compound is solvated in glycerin over an extended period of time.

In yet another variation, a micronized form of the inventive compound may also be employed to enhance solvation kinetics. Optionally, micronization may be performed by a milling process. As an example, micronization may be performed by milling process performed Mastersizerusing an Air Jet Mill, manufactured by IncFluid Energy Aljet Inc. (Boise, IDTelford, Pa.).

Optionally, the method further comprises adjusting the pH of the pharmaceutical formulations by commonly used methods. In one variation, pH is adjusted by addition of acid, such as ascorbic acid, or base, such as sodium hydroxide. In another variation, pH is adjusted and stabilized by addition of buffered solutions, such as solution of (Ethylenedinitrilo) tetraacetic acid disodium salt (EDTA). As decitabine is known to be pH-sensitive, adjusting the pH of the pharmaceutical formulations to approximately pH 7 may increase the stability of therapeutic component.

Optionally, the method further comprises separation of non-dissolved inventive compound from the pharmaceutical formulations. Separation may be performed by any suitable technique. For example, a suitable separation method may include one or more of filtration, sedimentation, and centrifugation of the pharmaceutical formulations. Clogging that may be caused by non-dissolved particles of the inventive compound, may become an obstacle for administration of the pharmaceutical formulations and a potential hazard for the patient. The separation of non-dissolved inventive compound from the pharmaceutical formulations may facilitate administration and enhance safety of the therapeutic product.

Optionally, the method further comprises sterilization of the pharmaceutical formulations. Sterilization may be performed by any suitable technique. For example, a suitable sterilization method may include one or more of sterile filtration, chemical, irradiation, heat, and addition of a chemical disinfectant to the pharmaceutical formulation.

As noted, decitabine is unstable in water and hence it may be desirable to reduce the water content of the glycerin used for formulating the inventive compound. Accordingly, prior to the dissolution and/or sterilization step, the glycerin may be dried. Such drying of glycerin or the solution of the inventive compound in glycerin may be achieved by the addition of a pharmaceutically acceptable drying agent to the glycerin. The glycerin or the inventive formulations may be dried, for example by filtering it through a layer comprising a drying agent.

Optionally, the method may further comprise adding one or more members of the group selected from drying agents, buffering agents, antioxidants, stabilizers, antimicrobials, and pharmaceutically inactive agents. In one variation, antioxidants such as ascorbic acid, ascorbate salts and mixtures thereof may be added. In another variation stabilizers like glycols may be added.

3. Vessels or Kits Containing Inventive Compounds or Formulations

The pharmaceutical formulations, described in this invention, may be contained in a sterilized vessel such as syringes, vials or ampoules of various sizes and capacities. The sterilized vessel may optionally contain between 1-50 ml, 1-25 ml or 1-20 ml or 1-10 ml of the formulations. Sterilized vessels maintain sterility of the pharmaceutical formulations, facilitate transportation and storage, and allow administration of the pharmaceutical formulations without prior sterilization step.

The present invention also provides a kit for administering the inventive compound to a host in need thereof. In one embodiment, the kit comprises the inventive compound in a solid, preferably powder form, and a non-aqueous diluent that comprises glyercin, propylene glycol, polyethylene glycol, or combinations thereof. Mixing of the solid decitabine and the diluent preferably results in the formation of a pharmaceutical formulation according to the present invention. For example, the kit may comprise a first vessel comprising the inventive compound in a solid form; and a vessel container comprising a diluent that comprises glyercin; wherein adding the diluent to the solid inventive compound results in the formation of a pharmaceutical formulation for administering the inventive compound. Mixing the solid the inventive compound and diluent may optionally form a pharmaceutical formulation that comprises between 0.1 and 200 mg of the inventive compound per ml of the diluent, optionally between 0.1 and 100, between 2 mg and 50 mg, 5 mg and 30 mg, between 10 mg and 25 mg per ml of the solvent.

According to the embodiment, the diluent is a combination of propylene glycol and glycerin, wherein the concentration of propylene glycol in the solvent is between 0.1-99.9%, optionally between 1-90%, between 10-60%, or between 20-40%.

Also according to the embodiment, the diluent is a combination of polyethylene glycol and glycerin, wherein the concentration of polyethylene glycol in the solvent is between 0.1-99.9%, optionally between 1-90%, between 10-60%, or between 20-40%.

Also according to the embodiment, the diluent is a combination of propylene glycol, polyethylene glycol and glycerin, wherein the concentration of propylene glycol in the solvent is between 0.1-99.9%, optionally between 1-90%, between 10-60%, or between 20-40%; and the concentration of polyethylene glycol in the solvent is between 0.1-99.9%, optionally between 1-90%, between 10-60%, or between 20-40%.

The diluent also optionally comprises 40%, 20%, 10%, 5%, 2% or less water. In one variation, the diluent is anhydrous and may optionally further comprise a drying agent. The diluent may also optionally comprise one or more drying agents, glycols, antioxidants and/or antimicrobials.

The kit may optionally further include instructions. The instructions may describe how the solid the inventive compound and the diluent should be mixed to form a pharmaceutical formulation. The instructions may also describe how to administer the resulting pharmaceutical formulation to a patient. It is noted that the instructions may optionally describe the administration methods according to the present invention.

The diluent and the inventive compound may be contained in separate vessels. The vessels may come in different sizes. For example, the vessel may comprise between 1 and 50, 1 and 25, 1 and 20, or 1 and 10 ml of the diluent.

The pharmaceutical formulations provided in vessels or kits may be in a form that is suitable for direct administration or may be in a concentrated form that requires dilution relative to what is administered to the patient. For example, pharmaceutical formulations, described in this invention, may be in a form that is suitable for direct administration via infusion.

The methods and kits described herein provide flexibility wherein stability and therapeutic effect of the pharmaceutical formulations comprising the inventive compound may be further enhanced or complemented.

4. Methods for Administrating Inventive Compounds/Compositions

The compounds/formulations of the present invention can be administered by any route, preferably in the form of a pharmaceutical composition adapted to such a route, as illustrated below and are dependent on the condition being treated. The compounds or formulations can be, for example, administered orally, parenterally, topically, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or co-administered in slow release dosage forms.

The compounds and/or compositions of this invention may be administered or co-administered in any conventional dosage form. Co-administration in the context of this invention is defined to mean the administration of more than one therapeutic agent in the course of a coordinated treatment to achieve an improved clinical outcome. Such co-administration may also be coextensive, that is, occurring during overlapping periods of time.

The inventive compound or the composition containing the inventive compound may be administered into a host such as a patient at a dose of 0.1-1000 mg/m$^2$, optionally 1-200 mg/m$^2$, optionally 1-50 mg/m$^2$, optionally 1-40 mg/m$^2$, optionally 1-30 mg/m$^2$, optionally 1-20 mg/m$^2$, or optionally 5-30 mg/m$^2$.

For example, the compound/composition of the present invention may be supplied as sterile powder for injection, together with buffering salt such as potassium dihydrogen and pH modifier such as sodium hydroxide. This formulation is preferably stored at 2 8° C., which should keep the drug stable for at least 2 years. This powder formulation may be reconstituted with 10 ml of sterile water for injection. This solution may be further diluted with infusion fluid known in the art, such as 0.9% sodium chloride injection, 5% dextrose injection and lactated ringer's injection. It is preferred that the reconstituted and diluted solutions be used within 4-6 hours for delivery of maximum potency.

In a preferred embodiment, the inventive compound/composition is administered to a patient by injection, such as subcutaneous injection, bolus i.v. injection, continuous i.v. infusion and i.v. infusion over 1 hour. Optionally the inventive compound/composition is administered to a patient via an 1-24 hour i.v. infusion per day for 3-5 days per treatment cycle at a dose of 0.1-1000 mg/m$^2$ per day, optionally at a dose of 1-100 mg/m$^2$ per day, optionally at a dose of 2-50 mg/m$^2$ per day, optionally at a dose of 10-30 mg/m$^2$ per day, or optionally at a dose of 5-20 mg/m$^2$ per day, For decitabine or azacitidine, the dosage below 50 mg/m$^2$ is considered to be much lower than that used in conventional chemotherapy for cancer. By using such a low dose of the analog/derivative of decitabine or azacitidine, transcriptional activity of genes silenced in the cancer cells by aberrant methylation can be activated to trigger downstream signal transduction, leading to cell growth arrest, differentiation and apoptosis, which eventually results in death of these cancer cells. This low dosage, however, should have less systemic cytotoxic effect on normal cells, and thus have fewer side effects on the patient being treated.

The pharmaceutical formulations may be co-administered in any conventional form with one or more member selected from the group comprising infusion fluids, therapeutic compounds, nutritious fluids, anti-microbial fluids, buffering and stabilizing agents.

As described above, the inventive compounds can be formulated in a liquid form by solvating the inventive compound in a non-aqueous solvent such as glycerin. The pharmaceutical liquid formulations provide the further advantage of being directly administrable, (e.g., without further dilution) and thus can be stored in a stable form until administration. Further, because glycerin can be readily mixed with water, the formulations can be easily and readily further diluted just prior to administration. For example, the pharmaceutical formulations can be diluted with water 180, 60, 40, 30, 20, 10, 5, 2, 1 minute or less before administration to a patient.

Patients may receive the pharmaceutical formulations intravenously. The preferred route of administration is by intravenous infusion. Optionally, the pharmaceutical formulations of the current invention may be infused directly, without prior reconstitution.

In one embodiment, the pharmaceutical formulation is infused through a connector, such as a Y site connector, that has three arms, each connected to a tube. As an example, Baxter® Y-connectors of various sizes can be used. A vessel containing the pharmaceutical formulation is attached to a tube further attached to one arm of the connector. Infusion fluids, such as 0.9% sodium chloride, or 5% dextrose, or 5% glucose, or Lactated Ringer's, are infused through a tube attached to the other arm of the Y-site connector. The infusion fluids and the pharmaceutical formulations are mixed inside the Y site connector. The resulting mixture is infused into the patient through a tube connected to the third arm of the Y site connector. The advantage of this administration approach over the prior art is that the inventive compound is mixed with infusion fluids before it enters the patient's body, thus reducing the time when decomposition of the inventive compound may occur due to contact with water. For example, the inventive compound is mixed less than 10, 5, 2 or 1 minutes before entering the patient's body.

Patients may be infused with the pharmaceutical formulations for 1, 2, 3, 4, 5 or more hours, as a result of the enhanced stability of the formulations. Prolonged periods of infusion enable flexible schedules of administration of therapeutic formulations.

Alternatively or in addition, speed and volume of the infusion can be regulated according to the patient's needs. The regulation of the infusion of the pharmaceutical formulations can be performed according to existing protocols.

The pharmaceutical formulations may be co-infused in any conventional form with one or more member selected from the group comprising infusion fluids, therapeutic compounds, nutritious fluids, anti-microbial fluids, buffering and stabilizing agents. Optionally, therapeutic components including, but are not limited to, anti-neoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies, may be co-infused with the inventive formulations.

Co-infusion in the context of this invention is defined to mean the infusion of more than one therapeutic agents in a course of coordinated treatment to achieve an improved clinical outcome. Such co-infusion may be simultaneous, overlapping, or sequential. In one particular example, co-infusion of the pharmaceutical formulations and infusion fluids may be performed through Y-type connector.

The pharmacokinetics and metabolism of intravenously administered the pharmaceutical formulations resemble the pharmacokinetics and metabolism of intravenously administered the inventive compound.

In humans, decitabine displayed a distribution phase with a half-life of 7 minutes and a terminal half-life on the order of 10-35 minutes as measured by bioassay. The volume of distribution is about 4.6 L/kg. The short plasma half-life is due to rapid inactivation of decitabine by deamination by liver cytidine deaminase. Clearance in humans is high, on the order of 126 mL/min/kg. The mean area under the plasma curve in a total of 5 patients was 408 µg/h/L with a peak plasma concentration of 2.01 µM. In patients decitabine concentrations were about 0.4 µg/ml (2 µM) when administered at 100 mg/m$^2$ as a 3-hour infusion. During a longer infusion time (up to 40 hours) plasma concentration was about 0.1 to 0.4 µg/mL. With infusion times of 40-60 hours, at an infusion rate of 1 mg/kg/h, plasma concentrations of 0.43-0.76 µg/mL were achieved. The steady-state plasma concentration at an infusion rate of 1 mg/kg/h is estimated to be 0.2-0.5 µg/mL. The half-life after discontinuing the infusion is 12-20 min. The steady-state plasma concentration of decitabine was estimated to be 0.31-0.39 µg/mL during a 6-hour infusion of 100 mg/m$^2$. The range of concentrations during a 600 mg/m$^2$ infusion was 0.41-16 µg/mL. Penetration of decitabine into the cerebrospinal fluid in man reaches 14-21% of the plasma concentration at the end of a 36-hour intravenous infusion. Urinary excretion of unchanged decitabine is low, ranging from less than 0.01% to 0.9% of the total dose, and there is no relationship between excretion and dose or plasma drug levels. High clearance values and a total urinary excretion of less than 1% of the administered dose suggest that decitabine is eliminated rapidly and largely by metabolic processes.

Owing to their enhanced stability in comparison with decitabine, the inventive compounds/compositions can enjoy longer shelf life when stored and circumvent problems associated with clinical use of decitabine. For example, the inventive compounds may be supplied as lyophilized powder, optionally with an excipient (e.g., cyclodextrin), acid (e.g., ascorbic acid), alkaline (sodium hydroxide), or buffer salt (monobasic potassium dihydrogen phosphate). The lyophilized powder can be reconstituted with sterile water for injection, e.g., i.v., i.p., i.m., or subcutaneously. Optionally, the powder can be reconstituted with aqueous or non-aqueous solvent comprising a water miscible solvent such as glycerin, propylene glycol, ethanol and PEG. The resulting solution may be administered directly to the patient, or diluted further with infusion fluid, such as 0.9% Sodium Chloride; 5% Dextrose; 5% Glucose; and Lactated Ringer's infusion fluid.

The inventive compounds/compositions may be stored under ambient conditions or in a controlled environment, such as under refrigeration (2-8° C.; 36-46° F.). Due to their superior stability in comparison with decitabine, the inventive compounds/compositions can be stored at room temperature, reconstituted with injection fluid, and administered to the patient without prior cooling of the drug solution.

In addition, due to their enhanced chemical stability, the inventive compound/composition should have a longer plasma half-life compared to that of decitabine. Thus, the inventive compound/composition may be administered to the patient at a lower dose and/or less frequently than that for decitabine.

5. Combination Therapy with Inventive Pharmaceutical Compositions

The compounds or pharmaceutical formulations of the present invention may be used in conjunction with inhibitors of histone deacetylase (HDAC) to further modulate transcription of genes, e.g., to reestablish transcription of genes silenced by hypermethylation and acetylation of histones, in a synergistic manner.

HDAC plays important roles in transcription silencing of genes. The amount of acetylation on the histones is controlled by the opposing activities of two types of enzymes, histone acetyl transferase (HATs) and histone deacetylases (HDACs). Substrates for these enzymes include e-amino groups of lysine residues located in the amino-terminal tails of the histones H3, H4, H2A, and H2B. These amino acid residues are acetylated by HATs and deacetylated by HDACs. With the removal of the acetyl groups from the histone lysine by HDACs, a positive charge is restored to the lysine residue, thereby condensing the structure of nucleosome and silencing the genes contained within. Thus, to activate these genes silenced by deacetylase of histones, the activity of HADCs should be inhibited. With the inhibition of HDAC, histones are acetylated and the DNA that is tightly wrapped around a deacetylated histone core relaxes. The opening of DNA conformation leads to expression of specific genes.

In addition to deacelation of histones, HDACs may also regulated gene expression by deacetylating transcription factors, such as p53 (a tumor suppressor gene), GATA-1, TFIIE, and TFIIF. Gu and Roeder (1997) Cell 90:595-606 (p53); and Boyes et al. (1998) Nature 396:594-598 (GATA-1). HDACs also participate in cell cycle regulation, for example, by transcription repression which is mediated by RB tumor suppressor proteins recruiting HDACs. Brehm et al. (1998) Nature 391:597-601. Thus, inhibition of HDACs should activate expression of tumor suppressor genes such as p53 and RB and as a result promote cell growth arrest, differentiation and apoptosis induced by these genes.

As described above, aberrant transcriptional silencing of a number of genes, such as tumor suppressor genes, is directly related to pathogenesis of cancer and other diseases. Methylation of cytosine residues in DNA and removal of acetyl groups from histones are the two primary mechanisms for gene silencing. Due to methylation and/or histone deacetylase of cancer-related genes, expression of these genes is suppressed or completely silenced. Meanwhile, expression of these genes is required for induction of growth arrest, differentiation, and/or apoptotic cell death of transformed cells. Inaction of these genes in the transformed cells leads to uncontrolled proliferation of these cells, which eventually results in cancer.

By combining the inventive compounds/compositions with HDAC inhibitors, genes required for induction of growth arrest, differentiation and cell death of transformed cells can be reactivated effectively. The inventive compounds/compositions inhibit methylation of DNA for the genes, especially in the regulatory region, thus resulting in activation of transcription of the gene. Meanwhile, HDAC inhibitors inhibit deacetylase of the histones in the nucleosomal core of the gene, thus resulting in net increase of the acetylation of histones, which, in turn, activates transcription of the gene. By exploiting these two complementary mechanisms, the combination therapy may reestablish gene transcription more effectively and, ideally, in a synergistic manner. A combination therapy having synergistic effects should require a less amount of each inhibitor than it being used alone, thus reducing potential side effects associated systemic administration of high dosages of the inhibitors and improving therapeutic index.

Many anticancer agents exert their anti-cancer effects by triggering signal transduction cascades involving proteins encoded by these tumor suppressor genes. With insufficient expression of these genes in cancer cells, the anti-cancer effects of these anti-neoplastic agents may be severely reduced or completely eradicated. Through reactivation or re-expression of these genes that are epigenetically silenced by DNA methylation and histone deacetylase, the intrinsic defense mechanisms of the body are mobilized to combat the disease by restoration of the tumor-suppressing functions to cancer cells in response to signals sent by the anti-cancer agent administered. Such stimulation of the intrinsic tumor suppressing functions of the body should lead to the requirement of lower dosage of the anticancer agent, thus resulting in a higher therapeutic index (i.e., greater efficacy and lower toxicity) of the agent.

Inhibitors of HDACs include, but are not limited to, the following structural classes: 1) hydroxamic acids, 2) cyclic peptides, 3) benzamides, and 4) short-chain fatty acids.

Examples of hydroxamic acids and hydroxamic acid derivatives, but are not limited to, trichostatin A (TSA), suberoylanilide hydroxamic acid (SAHA), oxamflatin, suberic bishydroxamic acid (SBHA), m-carboxy-cinnamic acid bishydroxamic acid (CBHA), and pyroxamide. TSA was isolated as an antifungi antibiotic (Tsuji et al (1976) J. Antibiot (Tokyo) 29:1-6) and found to be a potent inhibitor of mammalian HDAC (Yoshida et al. (1990) J. Biol. Chem. 265:17174-17179). The finding that TSA-resistant cell lines have an altered HDAC evidences that this enzyme is an important target for TSA. Other hydroxamic acid-based HDAC inhibitors, SAHA, SBHA, and CBHA are synthetic compounds that are able to inhibit HDAC at micromolar concentration or lower in vitro or in vivo. Glick et al. (1999) Cancer Res. 59:4392-4399. These hydroxamic acid-based HDAC inhibitors all possess an essential structural feature: a polar hydroxamic terminal linked through a hydrophobic methylene spacer (e.g. 6 carbon at length) to another polar site which is attached to a terminal hydrophobic moiety (e.g., benzene ring). Compounds developed having such essential features also fall within the scope of the hydroxamic acids that may be used as HDAC inhibitors.

Cyclic peptides used as HDAC inhibitors are mainly cyclic tetrapeptides. Examples of cyclic peptides include, but are not limited to, trapoxin A, apicidin and FR901228. Trapoxin A is a cyclic tetrapeptide that contains a 2-amino-8-oxo-9,10-epoxy-decanoyl (AOE) moiety. Kijima et al. (1993) J. Biol. Chem. 268:22429-22435. Apicidin is a fungal metabolite that exhibits potent, broad-spectrum antiprotozoal activitity and inhibits HDAC activity at nanomolar concentrations. Darkin-Rattray et al. (1996) Proc. Natl. Acad. Sci. USA. 93;13143-13147. FR901228 is a depsipeptide that is isolated from *Chromobacterium violaceum*, and has been shown to inhibit HDAC activity at micromolar concentrations.

Examples of benzamides include but are not limited to MS-27-275. Saito et al. (1990) Proc. Natl. Acad. Sci. USA. 96:4592-4597. Examples of short-chain fatty acids include but are not limited to butyrates (e.g., butyric acid, arginine butyrate and phenylbutyrate (PB)). Newmark et al. (1994) Cancer Lett. 78:1-5; and Carducci et al. (1997) Anticancer Res. 17:3972-3973. In addition, depudecin which has been shown to inhibit HDAC at micromolar concentrations (Kwon et al. (1998) Proc. Natl. Acad. Sci. USA. 95:3356-3361) also falls within the scope of histone deacetylase inhibitor of the present invention.

The compounds or pharmaceutical formulations of the present invention may also be used in conjunction with other therapeutic components including but not limiting to antineoplastic agents, alkylating agents, agents that are members of the retinoids superfamily, antibiotic agents, hormonal agents, plant-derived agents, biologic agents, interleukins, interferons, cytokines, immuno-modulating agents, and monoclonal antibodies.

In one embodiment, an alkylating agent is used in combination with and/or added to the inventive compound/formulation. Examples of alkylating agents include, but are not limited to bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin).

In another embodiment, cisplatin, carboplatin or cyclophosphamide is used in combination with and/or added to the inventive compound/formulation.

In another embodiment, a member of the retinoids superfamily is used in combination with and/or added to the inventive compound/formulation. Retinoids are a family of structurally and functionally related molecules that are derived or related to vitamin A (all-trans-retinol). Examples of retinoid include, but are not limited to, all-trans-retinol, all-trans-retinoic acid (tretinoin), 13-cis retinoic acid (isotretinoin) and 9-cis-retinoic acid.

In yet another embodiment, a hormonal agent is used in combination with and/or added to the inventive compound/formulation. Examples of such a hormonal agent are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

In yet another embodiment, a plant-derived agent is used in combination with and/or added to the inventive compound/formulation. Examples of plant-derived agents include, but are not limited to, *vinca* alkaloids (e.g., vincristine, vinblastine, vindesine, vinzolidine and vinorelbine), camptothecin (20(S)-camptothecin, 9-nitro-20(S)-camptothecin, and 9-amino-20(S)-camptothecin), podophyllotoxins (e.g., etoposide (VP-16) and teniposide (VM-26)), and taxanes (e.g., paclitaxel and docetaxel).

In yet another embodiment, a biologic agent is used in combination with and/or added to the inventive compound/formulation, such as immuno-modulating proteins such as cytokines, monoclonal antibodies against tumor antigens, tumor suppressor genes, and cancer vaccines.

Examples of interleukins that may be used in combination with and/or added to the inventive compound/formulation include, but are not limited to, interleukin 2 (IL-2), and interleukin 4 (IL-4), interleukin 12 (IL-12). Examples of interferons that may be used in conjunction with decitabine glycerin formulations include, but are not limited to, interferon α, interferon β (fibroblast interferon) and interferon γ (fibroblast interferon). Examples of such cytokines include, but are not limited to erythropoietin (epoietin □), granulocyte-CSF (filgrastim), and granulocyte, macrophage-CSF (sargramostim) Immuno-modulating agents other than cytokines include, but are not limited to *bacillus* Calmette-Guerin, levamisole, and octreotide.

Example of monoclonal antibodies against tumor antigens that can be used in conjunction with the inventive formulations include, but are not limited to, HERCEPTIN® (Trastruzumab), RITUXAN® (Rituximab), MYLOTARG® (anti-CD33), and CAMPATH® (anti-CD52).

6. Indications for Compounds or Pharmaceutical Compositions of the Present Invention The pharmaceutical formulations according to the present invention may be used to treat a wide variety of diseases that are sensitive to the treatment with decitabine.

Preferable indications that may be treated using the pharmaceutical formulations of the present invention include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present invention include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Specific types of cancers or malignant tumors, either primary or secondary, that can be treated using this invention include breast cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal gangloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

Hematologic disorders include abnormal growth of blood cells which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Acute myeloid leukemia (AML) is the most common type of acute leukemia that occurs in adults. Several inherited genetic disorders and immunodeficiency states are associated with an increased risk of AML. These include disorders with defects in DNA stability, leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15;17 chromosomal translocation. This translocation leads to the generation of the fusion transcript comprised of the retinoic acid receptor and a sequence PML.

Acute lymphoblastic leukemia (ALL) is a heterogenerous disease with distinct clinical features displayed by various subtypes. Reoccurring cytogenetic abnormalities have been demonstrated in ALL. The most common cytogenetic abnormality is the 9:22 translocation. The resultant Philadelphia chromosome represents poor prognosis of the patient.

Chronic myelogenous leukemia (CML) is a clonal myeloproliferative disorder of a pluripotent stem cell. CML is characterized by a specific chromosomal abnormality involving the translocation of chromosomes 9 and 22, creating the Philadelphia chromosome. Ionizing radiation is associated with the development of CML.

The myelodysplastic syndromes (MDS) are heterogeneous clonal hematopoietic stem cell disorders grouped together because of the presence of dysplastic changes in one or more of the hematopoietic lineages including dysplastic changes in the myeloid, erythroid, and megakaryocytic series. These changes result in cytopenias in one or more of the three lineages. Patients afflicted with MDS typically develop complications related to anemia, neutropenia (infections), or thrombocytopenia (bleeding). Generally, from about 10% to about 70% of patients with MDS develop acute leukemia.

Treatment of abnormal cell proliferation due to insults to body tissue during surgery may be possible for a variety of surgical procedures, including joint surgery, bowel surgery, and cheloid scarring. Diseases that produce fibrotic tissue include emphysema. Repetitive motion disorders that may be treated using the present invention include carpal tunnel syndrome. An example of cell proliferative disorders that may be treated using the invention is a bone tumor.

The proliferative responses associated with organ transplantation that may be treated using this invention include those proliferative responses contributing to potential organ rejections or associated complications. Specifically, these proliferative responses may occur during transplantation of the heart, lung, liver, kidney, and other body organs or organ systems.

Abnormal angiogenesis that may be may be treated using this invention include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), muscular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In another embodiment, the pharmaceutical formulations of the present invention may be used for treating diseases associated with undesired or abnormal angiogenesis. The method comprises administering to a patient suffering from undesired or abnormal angiogenesis the pharmaceutical formulations of the present invention alone, or in combination with anti-neoplastic agent whose activity as an anti-neoplastic agent in vivo is adversely affected by high levels of DNA methylation. The particular dosage of these agents required to inhibit angiogenesis and/or angiogenic diseases may depend on the severity of the condition, the route of administration, and related factors that can be decided by the attending physician. Generally, accepted and effective daily doses are the amount sufficient to effectively inhibit angiogenesis and/or angiogenic diseases.

According to this embodiment, the pharmaceutical formulations of the present invention may be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In yet another embodiment, the pharmaceutical formulations of the present invention may be used for treating chronic inflammatory diseases associated with abnormal angiogenesis. The method comprises administering to a patient suffering from a chronic inflammatory disease associated with abnormal angiogenesis the pharmaceutical formulations of the present invention alone, or in combination with an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the pharmaceutical formulations of the present invention may prevent the formation of the granulosmas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present invention should inhibit the formation of the sprouts and prevent the formation of granulomas. The inflammatory bowel diseases also exhibit extra intestinal manifectations, such as skin lesions. Such lesions are characterized by inflammation and angiogenesis and can occur at many sites other the gastrointestinal tract. Inhibition of angiogenesis by the pharmaceutical formulations of the present invention should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the pharmaceutical formulations of the present invention to inhibit angionesis, such granulomas formation can be inhibited. Psoriasis, also a chronic and recurrent inflammatory disease, is characterized by papules and plaques of various sizes. Treatment using the pharmaceutical formulations of the present invention should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using the pharmaceutical formulations of the present invention alone or in conjunction with other anti-RA agents may prevent the formation of new blood vessels necessary to maintain the chronic inflammation and provide the RA patient relief from the symptoms.

In yet another embodiment, the pharmaceutical formulations of the present invention may be used for treating diseases associated with abnormal hemoglobin synthesis. The method comprises administering the pharmaceutical formulations of the present invention to a patient suffering from disease associated with abnormal hemoglobin synthesis. Decitabine containing formulations stimulate fetal hemoglobin synthesis because the mechanism of incorporation into DNA is associated with DNA hypomethylation. Examples of diseases associated with abnormal hemoglobin synthesis include, but are not limited to, sickle cell anemia and β-thalassemia.

In yet another embodiment, the pharmaceutical formulations of the present invention may be used to control intracellular gene expression. The method comprises administering the pharmaceutical formulations of the present invention to a patient suffering from disease associated with abnormal levels of gene expression. DNA methylation is associated with the control of gene expression. Specifically, methylation in or near promoters inhibit transcription while demethylation restores expression. Examples of the possible applications of the described mechanisms include, but are not limited to, therapeutically modulated growth inhibition, induction of apoptosis, and cell differentiation.

Gene activation facilitated by the pharmaceutical formulations of the present invention may induce differentiation of cells for therapeutic purposes. Cellular differentiation is induced through the mechanism of hypomethylation. Examples of morphological and functional differentiation include, but are not limited to differentiation towards formation of muscle cells, myotubes, cells of erythroid and lymphoid lineages.

Although exemplary embodiments of the present invention have been described and depicted, it will be apparent to the artisan of ordinary skill that a number of changes, modifications, or alterations to the invention as described herein may be made, none of which depart from the spirit of the present invention. All such changes, modifications, and alterations should therefore be seen as within the scope of the present invention.

EXAMPLES

1. Synthesis of Phosphoramidite Building Blocks and 3'-O-Capped Derivatives

Figure 2A:
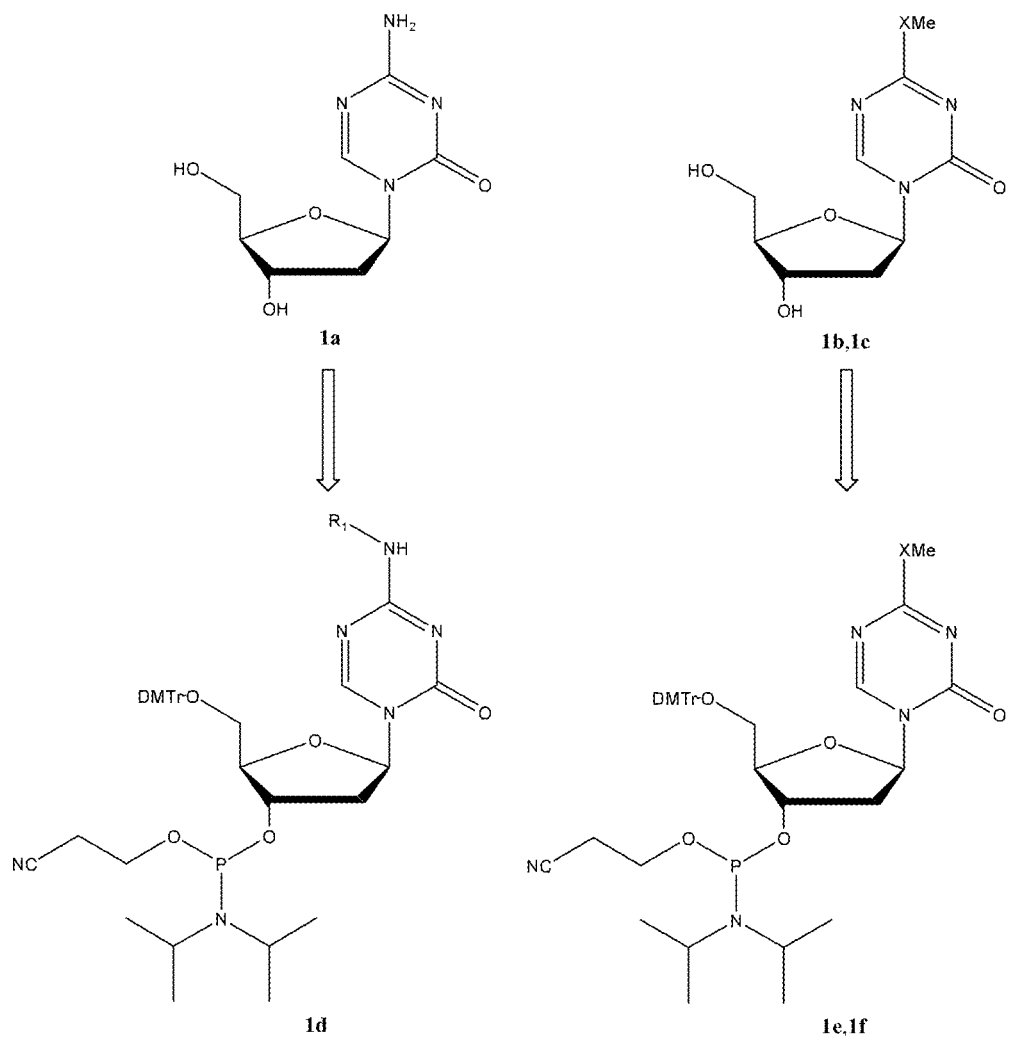
FIG. 2A depicts examples of decitabine phosphoramidite building blocks.
Figure 2B:
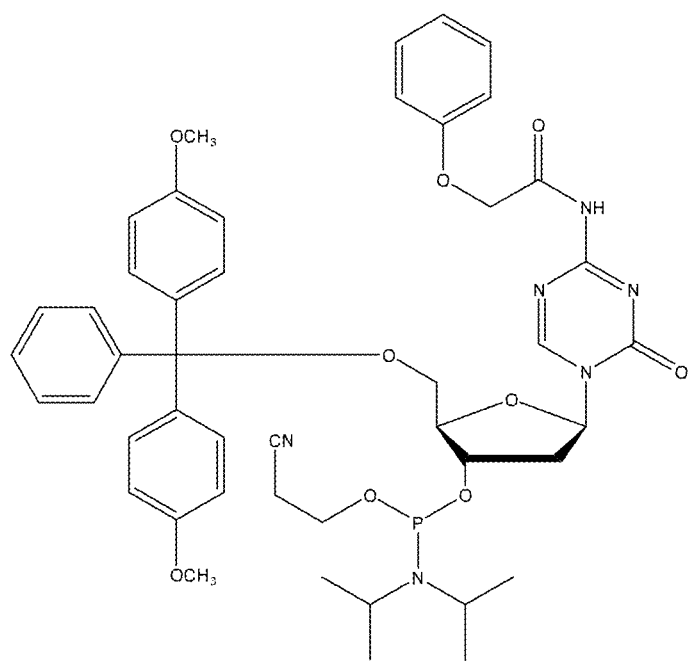
FIG. 2B depicts decitabine phosphoramidite building block 1d, where R₁=phenoxyacetyl.
Figure 3A:
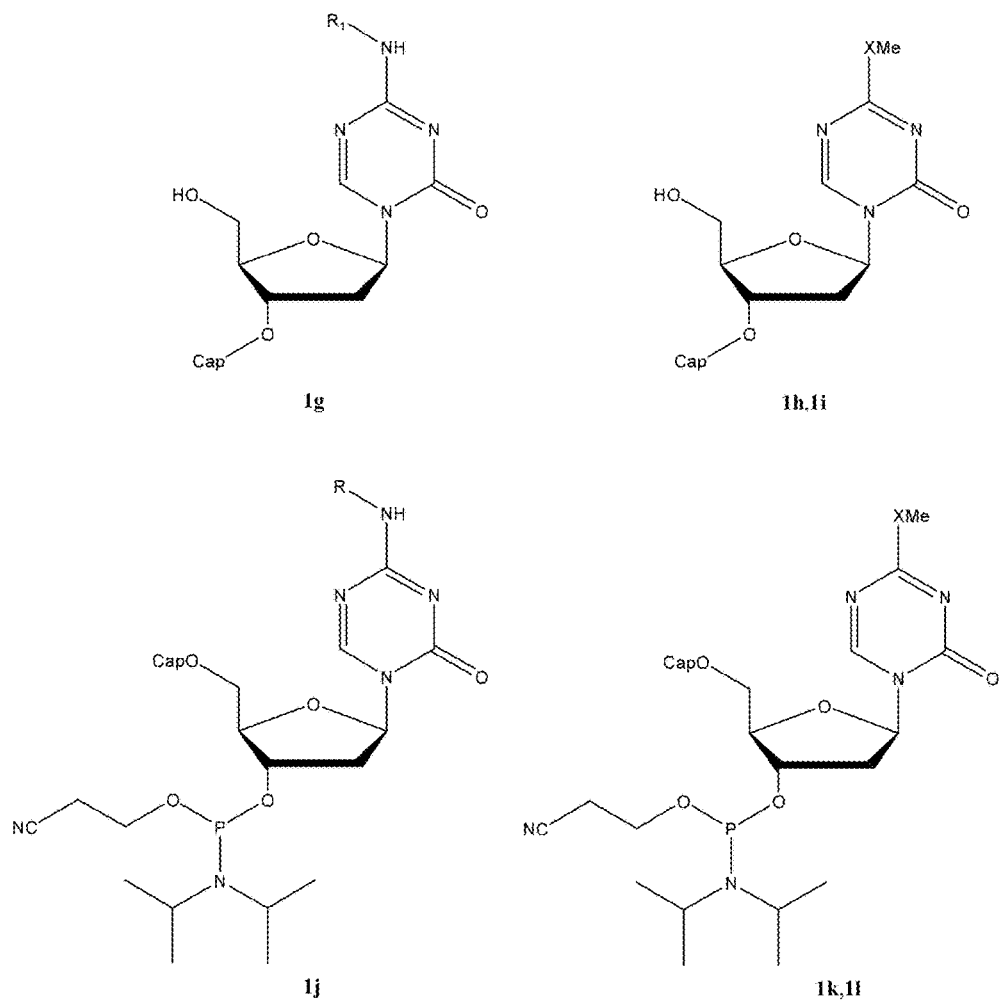
FIG. 3A depicts 3'- and 5'-O-capped and controlled-pore glass 3'-linked decitabine derivatives.
Figure 3B:
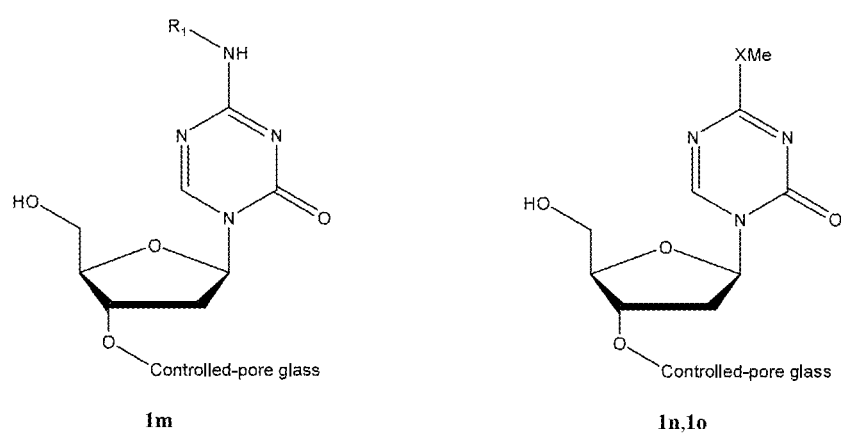
FIG. 3B depicts protected decitabine 3'-linked onto controlled-pore glass support

The present invention also provides effective chemical methods for synthesis of the following novel phosphoramidite building blocks (FIG. 2A).

The 4-amine functional group of 1a can be protected via transformation into various protective groups ($R_1$), such as carbamates with methyl, ethyl, 9-fluorenylmethyl, 9-(2-sulfo)fluorenylmethyl, 9-(2,7-dibromo)fluorenylmethyl, 17-tetrabenzo[a,e,g,i]fluorenylmethyl, 2-chloro-3-indenylmethyl, benz[f]inden-3-ylmethyl, 2,7-di-tert-[9-(10,10-dioxo-10,10,10,10-tetrahydrothioxanthyl)methyl, 1,1-dioxobenzo[b]thiophene-2-ylmethyl, 2,2,2-trichloroethyl, 2-trimethylsilylethyl, 2-phenylethyl, 1-(1-adamantyl)-1-methylethyl, 2-chloroethyl, 1,1,-dimethyl-2-haloethyl, 1,1-dimethyl-2,2-dibromethyl, 1,1-dimethyl-2,2,2-trichlroethyl, 1-methyl-1-(4-biphenylyl)ethyl, 1-(3,5-di-tert-butylphenyl)-1-methylethyl, 2-(2'- and 4'-pyridyl)ethyl, 2,2-bis(4'-nitrophenyl)ethyl, N-(2-pivaloylamino)-1,1-dimethylethyl, 2-[(2- nitrophenyl)dithio]-1-phenylethyl, 2-(N,N-dicyclohexylcarboxamido)ethyl, t-butyl, 1-adamantyl, 2-adamantyl, vinyl, allyl, 1-isopropylallyl, cinnayl, 4-nitrocinnamyl, 3-(3'-pyridyl)prop-2-enyl, 8-quinolyl, N-hydroxypiperidinyl, benzyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl, 2-methylthioethyl, 2-methylsulfonylethyl, 2-(p-toluenesulfonyeethyl, [2-(1,3-dithianye]methyl, 4-methylthiphenyl, 2,4-dimethylthiphenyl, 2-phosphonioethyl, 1-methyl-1-(triphenylphosphonio)ethyl, 1,1-dimethyl-2-cyanoethyl, 2-dansylethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoroethyl)-6-chromonylmethyl, m-nitrophenyl, 3,5-dimethoxybenzyl, 1,-methyl-1-(3,5-dimethoxyphenyl)ethyl, α-methylnitropiperonyl, o-nitrophenyl, 3,4-dimethoxy-6-nitrobenzyl, phenyl(o-nitrophenyl)ethyl, 2-(2-nitrophenyl)ethyl, 6-nitroveratryl, 4-methoxyphenacyl, 3',5'-dimethoxybenzoin, t-amyl, S-benzylthio, butynyl, p-cyanobenzyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethycarboxamido)propyl, 1,1-dimethylpropynyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyeethyl, 1-methyl-1-phenylethyl, 1-methyl-1-(4'-pyridyeethyl, phenyl, p-(phenylazo)benzyl, 2,4,6-tri-t-butylphenyl, 4-(trimethylammonium)benzyl, 2,4,6-trimethylbenzyl; ureas with phenothiazinyl-(10)-carbonyl, N'-p-toluenesulfonylaminocarbonyl, N'-phenylaminothiocarbonyl; amides such as formamide, acetamide, phenoxyacetamide, trichloroacetamide, trifluoroacetamide, phenyacetamide, 3-phenylpropamide, pent-4-enamide, o-nitrophenylacetamide, o-nitrophenoxyacetamide, 3-(o-nitrophenyl)propanamide, 2-methyl-2-(o-nitrophenoxy)propanamide, 3-methyl-3-nitrobutanamide, o-nitrocinnamide, 3-(4-t-butyl-2,6-dinitrophenyl)-2,2-dimethylpropanamide, o-(benzoyloxymethyObenzamide, 2-[(t-butyldiphenylsiloxy)methyl)methyl]benzamide, 3-(3',6'-dioxo-2',4',5'-trmethylcyclohexa-1',4'-diene)-3,3-dimethylpropionamide, o-hydroxy-trans-cinnamide, acetoacetamide, p-toluenesulfonamide, and benzesulfonamide. The 4-O-methoxy (1b) and 4-S-methylthio (1c) analogs of decitabine can be obtained by modifying the published procedure for decitabine synthesis by separating the α and β anomers of 1-(2-deoxy-3,5-di-O-p-chlorobenzoyl or benzoyl-D-ribofuranosyl)-4-methoxy or methylthio-1,3,5-triazin-2(H)-one and removing the 3,5-protective groups without treatment with methanolic ammonia. Pliml and Sorm (1964) Collect. Czech. Chem. Commun. 29: 2576-2577; Piskala and Sorm (1978) Nucleic Acid Chemistry (by Towsend and Tipson, Wiley, 1978), pp. 443-449.

Protection of the 5'-OH is achieved by dissolving the 4-amino protected decitabine and 4-methoxy and 4-methylthio analogs (1b, 1c) in anhydrous pyridine (5 mL/mmol) before adding dimethoxytrityl chloride (1.1 equivalents).

For example, decitabine (1.2 g) was twice co-distilled with anhydrous pyridine and dissolved in 20 ml dry DMF. Hexamethyldisilazane (2.8 mL) was added. The solution was stirred and left overnight. The solvent was evaporated in vacuo, and the remaining residue was dissolved in toluene and evaporated twice. The 3',5'-di trimethylsilyl 5-aza-2'-deoxycytidine ($R_f$=0.67, 4:1 dichloromethane/methanol) was co-distilled twice with dry pyridine (~10 mL) and dissolved in dry pyridine (20 mL). Phenoxyacetic anhydride (1.5 g) was added, and the resulting solution was stirred for 1 hour. A further 0.18 g phenoxyacetic anhydride (0.18 g) was added and stirred for another hour. The reaction mixture was evaporated in vacuo to dryness and co-distilled (3x) with toluene. The residue was dissolved in dichloromethane (~50 mL) and extracted with 1M aqueous NaHCO$_3$ solution (~50 mL), which was re-extracted with dichloromethane (~20 mL). The combined organic phases were dried over sodium sulfate and reduced in vacuo to yield crude 3',5'-di trimethylsilyl-N-phenoxyacetyl 5-aza-2'-deoxycytidine (3 g; $R_f$=0.82, 9:1 dichloromethane/methanol). The crude material was dissolved in anhydrous DMF (20 mL) and transferred to a 50 mL plastic falcon tube, and TAS-F (2.4 g) was added (gas evolved). The reaction proceeded for 4 hours at 22° C. (the vial was not fully closed to reduce pressure built up). The DMF was evaporated in vacuo and the remaining residue was subjected to column chromatography (30 g silica gel, 2.5 cm column, 99:1 to 9:1 dichloromethane/methanol). A white solid N-phenoxyacetyl 5-aza-2'-deoxycytidine (0.81 g; $R_f$=0.26, 9:1 dichloromethane/methanol) was obtained. This compound (0.6 g) was twice co-distilled with anhydrous pyridine and dissolved in anhydrous pyridine (20 mL) before dimethoxytrityl chloride (0.9 g) was added and stirred for 2 hours at 22° C. Solvents were removed in vacuo and co-distilled (3x) with toluene. The residue was dissolved in dichloromethane (50 mL) and extracted with 1M aqueous NaHCO$_3$ solution (~50 mL), which was re-extracted with dichloromethane (~20 mL). The combined organic phases were dried over sodium sulfate and reduced in vacuo. The residue was subjected to silica gel chromatography (dichloromethane-100% to 95:5 dichloromethane/methanol), which yielded 5'-dimethoxytrityl-N-phenoxyacetyl 5-aza-2'-deoxycytidine (0.35 g, 0.53 mmole, 32%; $R_f$=0.49, 9:1 dichloromethane/methanol). This intermediate (0.3 g) was dissolved in dry acetonitrile (2 mL) before 0.3 M benzylthiotetrazole (0.9 mL) solution in dry acetonitrile and cyanoethyltetraisopropyl phosphorodiamidite (0.17 mL) were added. The mixture was stirred at 22 t for 1.5 hours. TLC (2:1 ethyl acetate/hexanes+2% TEA) showed a diastereoisomeric mixture with $R_f$=0.27 and 0.36. Solvent was removed in vacuo and the remaining residue subjected to column chromatography (20 g silica gel, 2.5 cm column, 9:1 hexanes/ethyl acetate+2% TEA (300 mL), 1:1 hexanes/ethyl acetate+1% TEA (200 mL), 1:2 hexanes/ethyl acetate+0% TEA (250 mL). The decitabine phosphoramidite building 1d, where $R_1$=phenoxyacetyl (0.297 g, 0.34 mmol, 76%) eluted with the 1:2 hexanes/ethyl acetate. ESI-MS of 1d (calculated exact mass for $C_{46}H_{53}N_6O_9P$ is 864.36) exhibited m/z 864.1 and 966.4 [M+NEt$_3$+H]; $^{31}$P NMR (CDCl$_3$, 500 MHz) exhibited 149.17 and 149.0 ppm; $^1$H NMR (CDCl$_3$, 500 MHz) exhibited chemical shifts (ppm) 8.63 & 8.59 (1H, doublet, H-6), 7.4-6.6 (18H, multiplet, aromatic DMTr/Pac), 6.05 (1H, triplet, H-1'), 4.79 (2H, singlet, CH$_2$ of Pac), 4.59 (1H, singlet, H-4'), 4.25 to 4.20 (1H, doublet, H-3'), 3.8-3.7 (1H, multiplet, P—O—CH$_2$), 3.70 (3H, singlet, CH$_3$O of DMTr), 3.68 (3H, singlet, CH$_3$O of DMTr), 3.6-3.48 (3H, multiplet, two CH's of isopropyl and one P—O—CH$_2$), 3.36-3.27 (2H, multiplet, H-5'), 2.80 (1H, singlet, H-2'), 2.53 (1H, singlet, H-2'), 2.40 (2H, multiplet, CH$_2$CN), 1.1 (12H, CH$_3$ of isopropyl).

In addition, minor modification of published procedures allow access to 3'- and 5'-O-capped derivatives (FIG. 3A, 1g, 1h, 1i, 1j, 1k, 1l) (Bagnall, Bell and Pearson (1978) J. of Fluorine Chem, 11: 93-107), where the cap can be alkyl groups, esters and fatty acid esters, glycol derivatives such as ethylene and propylene glycols; and protected decitabine 3'-linked onto controlled-pore glass support (FIG. 3B, 1m, 1n, 1o). Alul, Singman, Than and Letsinger (1991) 19: 1527-1532.

Figure 4:
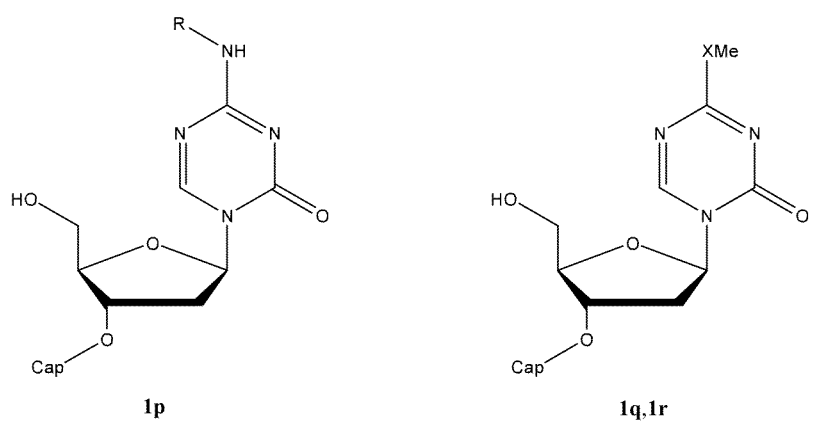
FIG. 4 depicts examples of 3'-O-capped decitabine derivatives.

Other decitabine derivatives have the 3'-OH protected with esters (which include but are not limited to acetyl, benzoyl, and halobenzoyl; and fatty acids) and ethers (which include but are not limited to p-nitrophenylethyl, methoxymethyl, methylthiomethyl, (phenyldimethylsilyemethoxymethyl, benzyloxymethyl, p-methoxybenzyloxymethyl, p-nitrobenzyloxymethyl, o-nitrobenzyloxymethyl, (4-methoxyphenoxy)methyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyeethoxymethyl, menthoxymethyl, tetrahydropyranyl, tetrahydrofuranyl, and 1-(2-fluorophenyl)-4-methoxypiperidin-4-yl), glycol derivatives such as ethylene and propylene glycos, as shown in FIG. 4.

2. Synthesis of DpG and GpD Dinucleotides and Tetranucleotides on Solid Support

Figure 5:
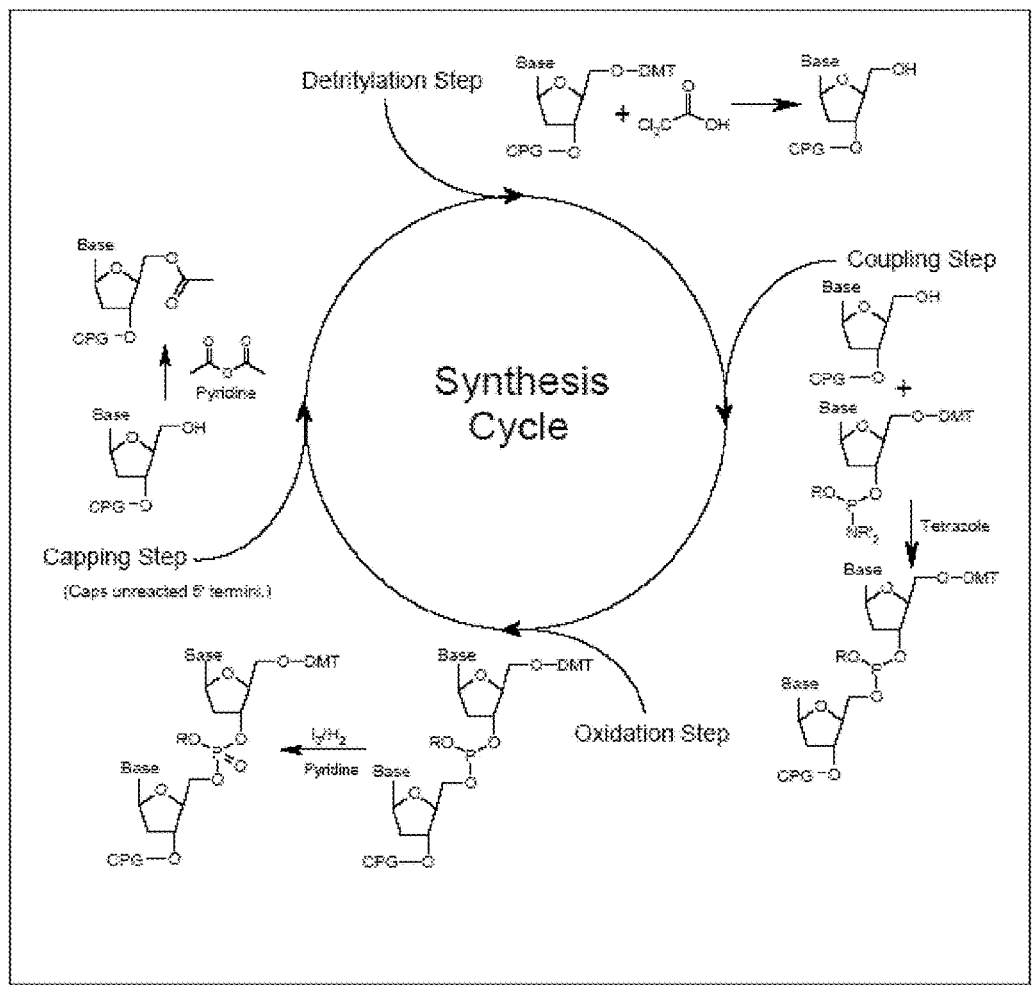
FIG. 5 illustrates a standard cycle for oligonucleotide synthesis.
Figure 6A:
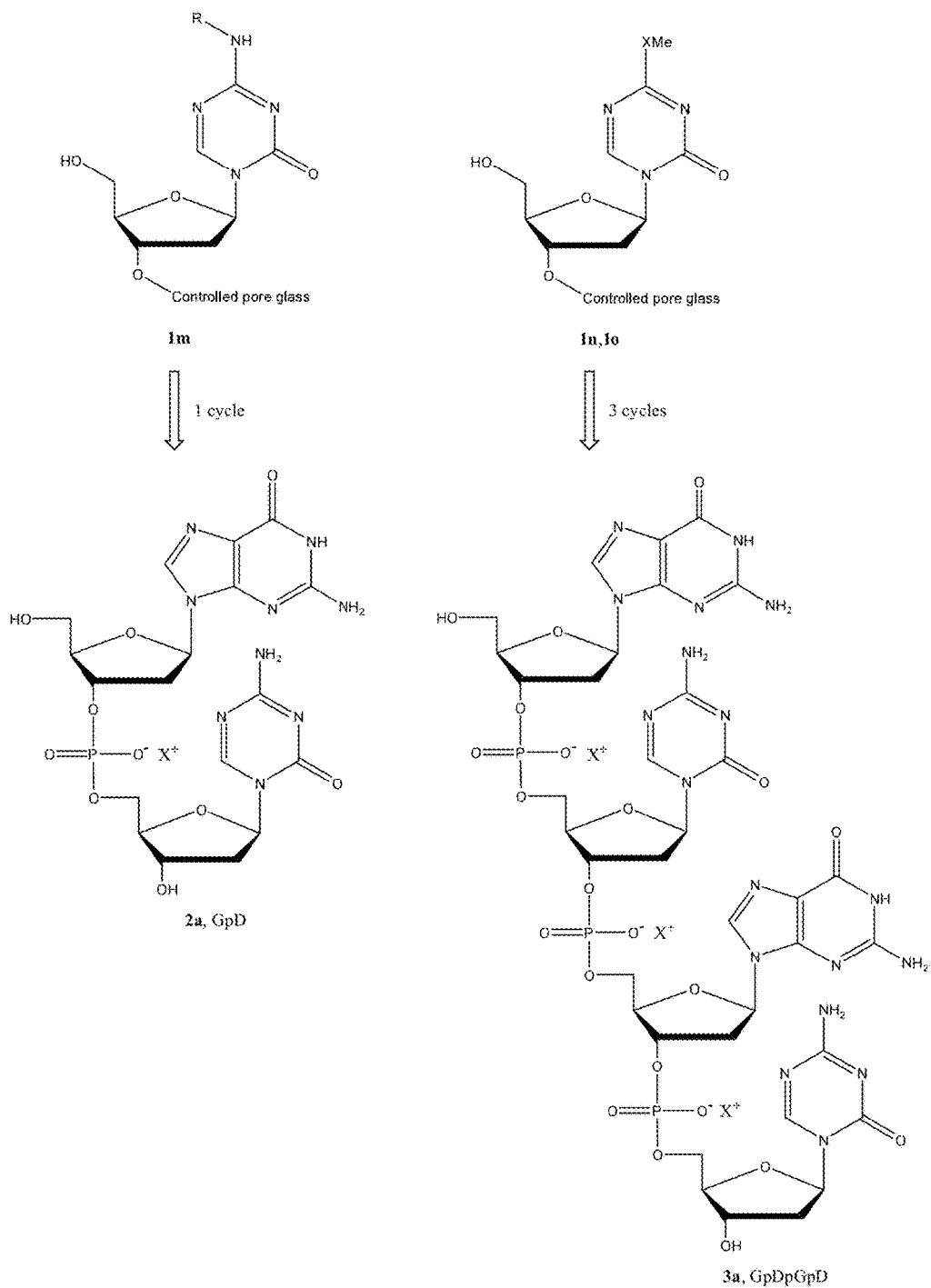
FIG. 6A shows synthesis schemes of GpD dinucleotides and tetranucleotides, where X⁺ is a counter ion.
Figure 7:
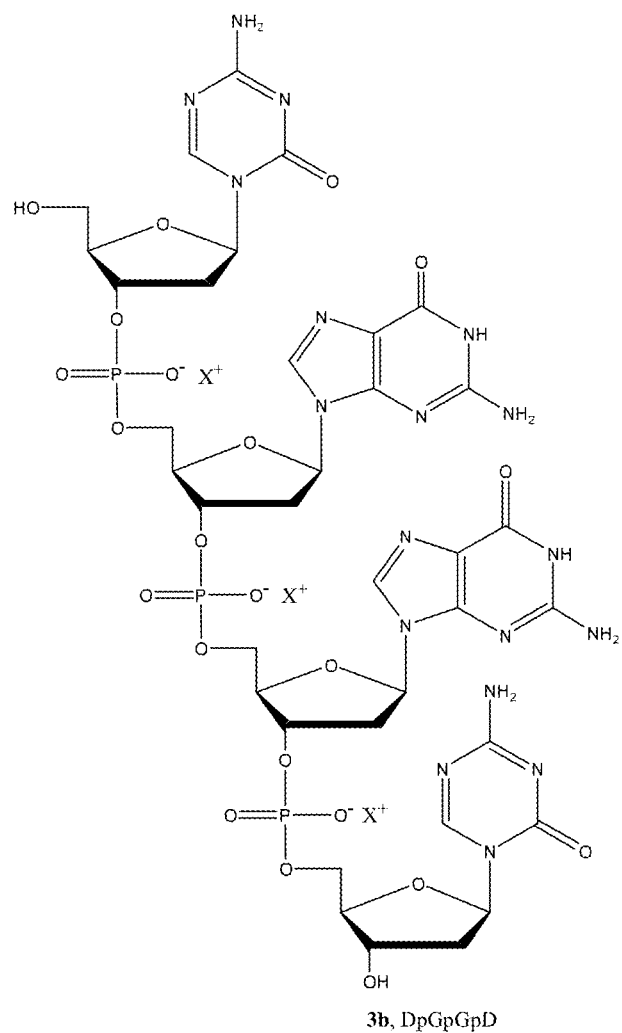
FIG. 7 depicts DpGpGpD tetranucleotide.

The DpG and GpD dinucleotides and tetranucleotides can be synthesized by standard procedures (FIG. 5) with slight modification for increased coupling times (>2 minutes). Beaucage and Caruthers (1981) Tet. Lett. 22: 1859-1862; McBride and Caruthers (1983) Tet. Lett. 24: 245-248. Synthesis of GpD dinucleotide 2a and DpGpGpD tetranucleotide 3a can be initiated with the coupling of 1m, 1n or 1o with similarly based protected 5'-O-DMTr 2'-deoxyguanosine-3'-O-cyanoethyl-N,N-diisopropylphosphoramidite and 5'-O-DMTr 2'-deoxy-5-aza-cytidine-3'-O-cyanoethyl-N,N-diisopropylphosphoramidites (1d, 1e or 1f), as shown in FIG. 6A. Subsequent release from the solid support (such as controlled pore glass, CPG) and removal of carbamate protective groups with bases such as DBU/pyridine (or acetonitrile), and methanolic ammonia for removal of the 4-O-methoxy and 4-O-methylthio protective groups, yield the desired oligonucleotides with the last DMTr group on or off. DpGpGpD (3b) can be similarly obtained (FIG. 7).

Figure 6B:
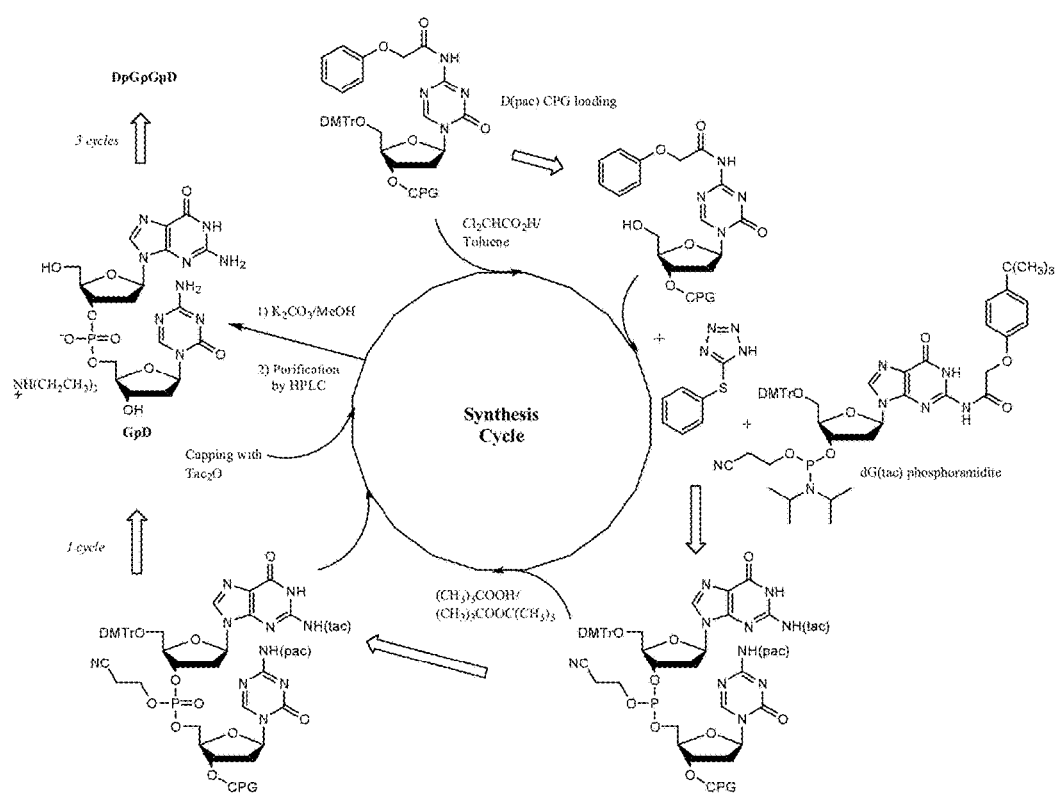
FIG. 6B depicts a model synthesis cycle of GpD dinucleotide (2a) and DpGpGpD tetranucleotide (3b).
Figure 30:
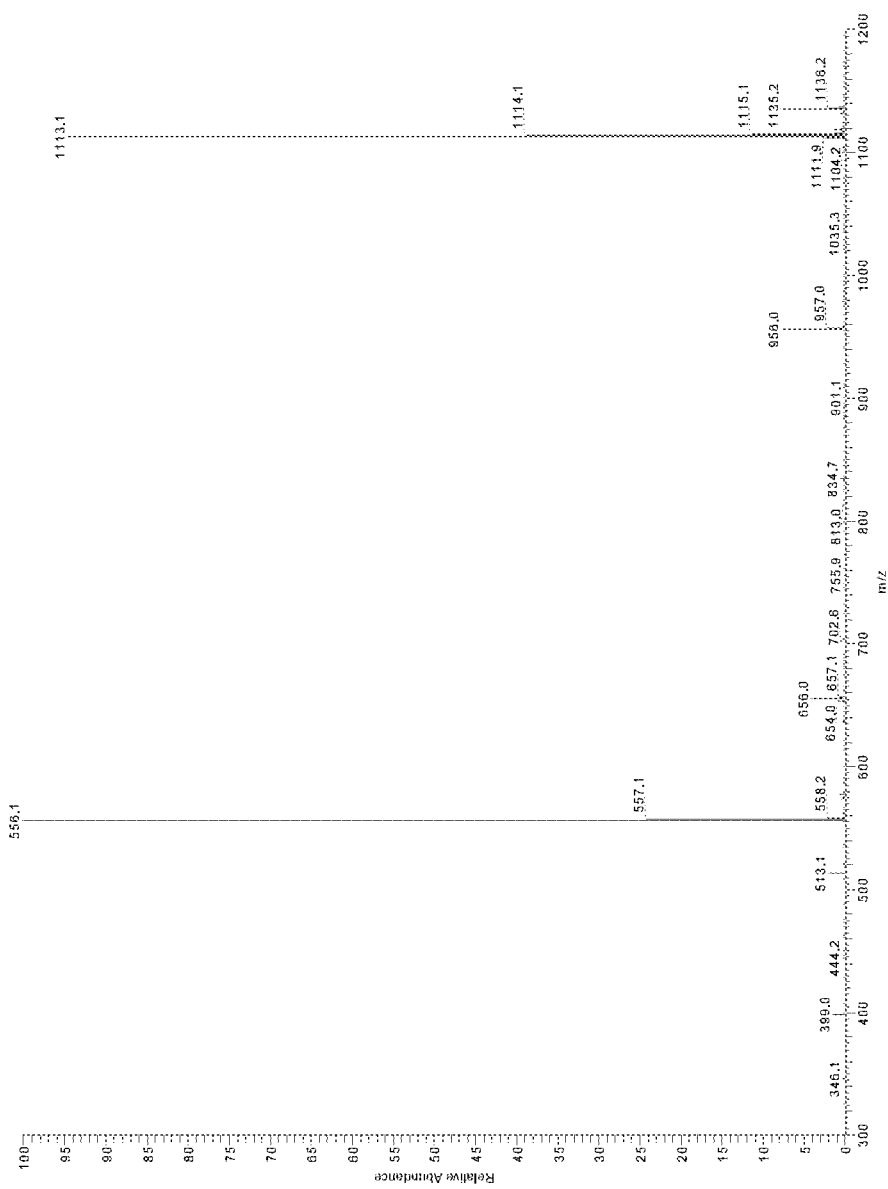
FIG. 30 is a mass spectrum of GpD (2a) triethylammonium salt.

For example (FIGS. 6A and 6B), an Amersham ÄKTA Oligopilot 10 system is loaded with a protected decitabine-linked CPG solid support 1m (where $R_1$=phenoxyacetyl), which is coupled with 2-2.5 equivalents of tert-butyl phenoxyacetyl 2'-deoxyguanosine phosphoramidite in presence of 60% of 0.3 M benzylthiotetrazole activator (in acetonitrile) for 2.5 minutes. The CPG solid support containing protected GpD dinucleotide is treated with 20 mL of 50 mM $K_2CO_3$ in methanol for 1 hour and 20 minutes. The coupled product is oxidized with 2 M tert-butylhydroperoxide in dry acetonitrile (prepared by dissolving tert-butylhydroperoxide in 80% tert-butylperoxide) for 5 minutes. The dimethoxy trityl protective group is removed with 3% dichloroacetic acid in toluene. The CPG solid support is washed with dry methanol; the filtrate is neutralized by addition of 2 mL of 1 M acetic acid in methanol. The solution is concentrated by rotary evaporation; the residue is taken up in 200 mM triethylammonium acetate (pH 6.9), washed with acetonitrile (500 μL of 50% aqueous acetonitrile), and filtered through a syringe filter. The GpD dinucleotide is subsequently purified by the ÄKTA Explorer 100 HPLC with a Gemini C18 preparative column (Phenomenex), 250×21.2 mm, 10 μm with guard column (Phenomenex), 50×21.2 mm, 10 μm, with 50 mM triethylammonium acetate (pH 7) in MilliQ water (Mobile Phase A) and 80% acetonitrile in MilliQ water (Mobile Phase B), with 2% to 20/25% Mobile Phase B in column volumes. The ESI-MS (−ve) of GpD dinucleotide 2a, where $X^+$=triethylammonium (calculated exact mass for the neutral compound $C_{18}H_{24}N_9O_{10}P$ is 557.14), exhibited m/z 556.1 [M-H]$^-$ and 1113.1 for [2M-H]$^-$ (see mass spectrum in FIG. 30).

Figure 32:
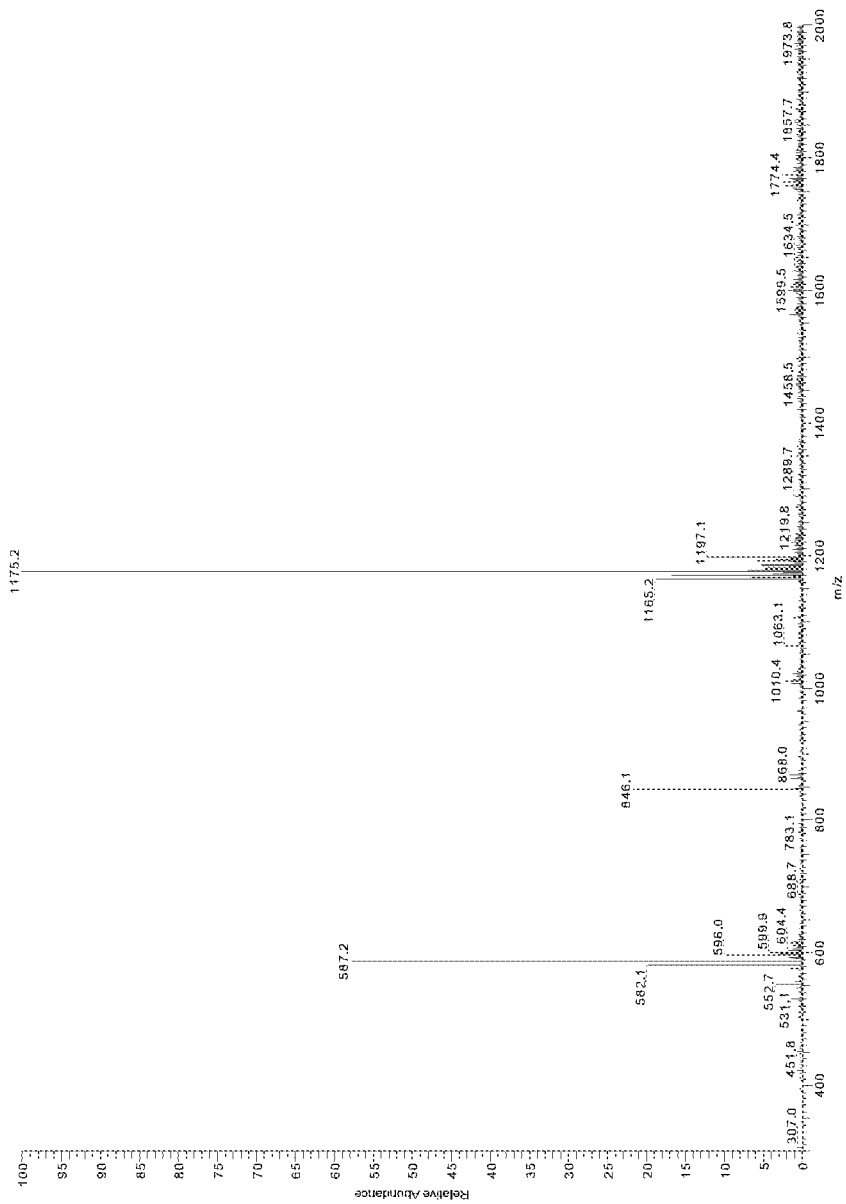
FIG. 32 is a mass spectrum of DpGpGpD (3b) triethylammonium salt.

When the cycle is repeated three times with 2-2.5 equivalents of tert-butyl phenoxyacetyl 2'-deoxyguanosine or phenoxyacetyl 5-aza-2'-deoxycytidine phosphoramidite in presence of 60% of 0.3 M benzylthiotetrazole activator (in acetonitrile) for 2.5 minutes and 10 minutes, respectively, (FIGS. 6b and 7), the DpGpGpD tetranucleotide 3b is obtained, where $X^+$=triethylammonium (calculated exact mass for the neutral compound $C_{36}H_{47}N_{18}O_{22}P_3$ is 1176.23), exhibited m/z 587.2 for [M-2H]$^{2-}$ and 1175.2 [M-H]$^-$ (FIG. 32).

Figure 8:
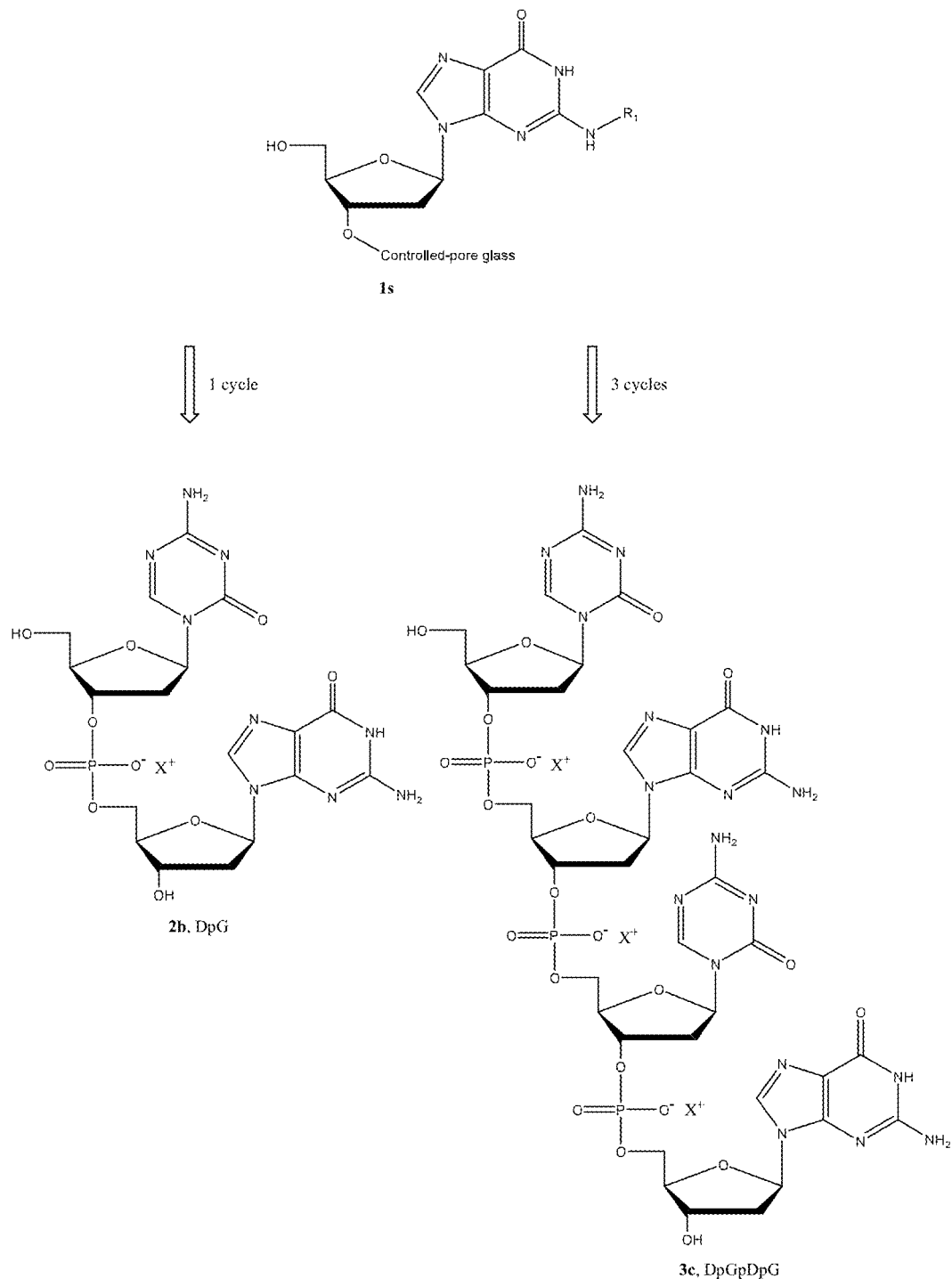
FIG. 8 shows synthesis schemes of GpD dinucleotides and tetranucleotides.
Figure 9:
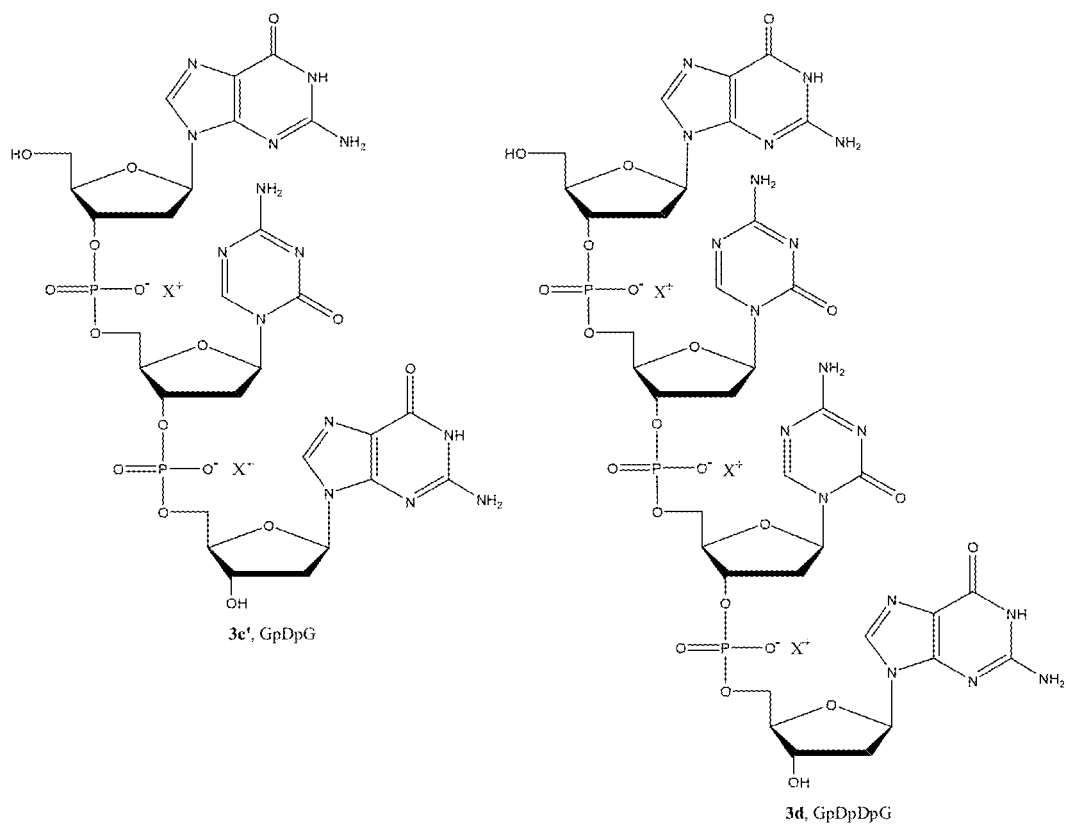
FIG. 9 depicts GpDpG trinucleotide and GpDpDpG tetranucleotide.

In addition, DpG dinucleotide 2b and GpDpGpD 3c can be synthesized by coupling is (where $R_1$=carbamate protective group) with phosphoramidite building blocks 1d, 1e or 1f (FIG. 8). GpDpDpG and GpDpG (3c') can likewise be obtained (FIG. 9).

Figure 31:
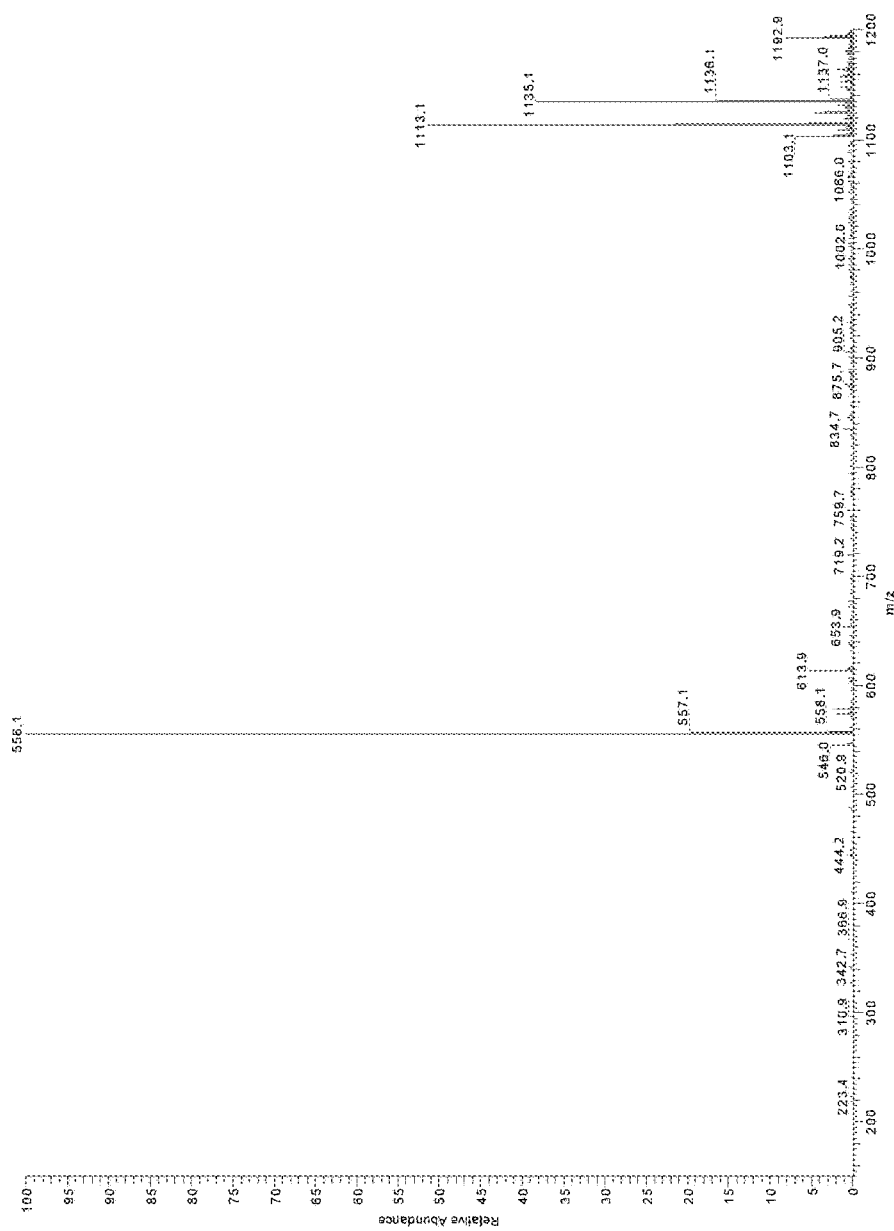
FIG. 31 is a mass spectrum of DpG (2b) triethylammonium salt.
Figure 36:
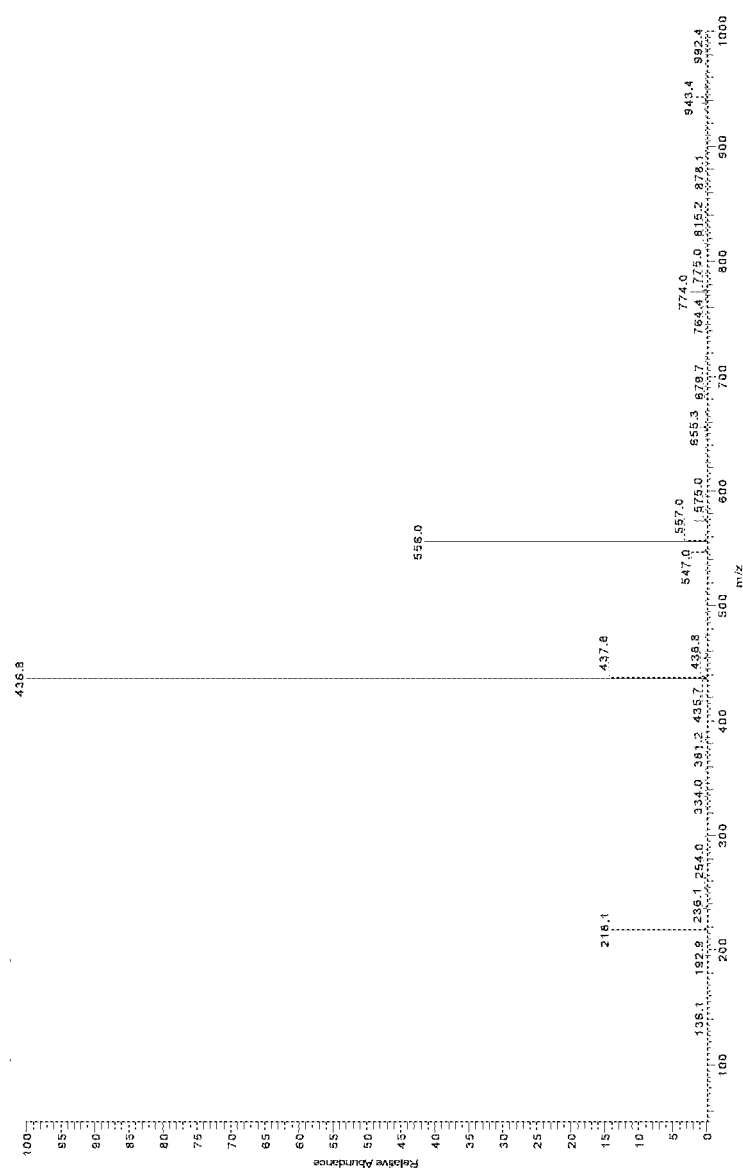
FIG. 36 is a mass spectrum of DpG (2b) sodium salt.
Figure 38:
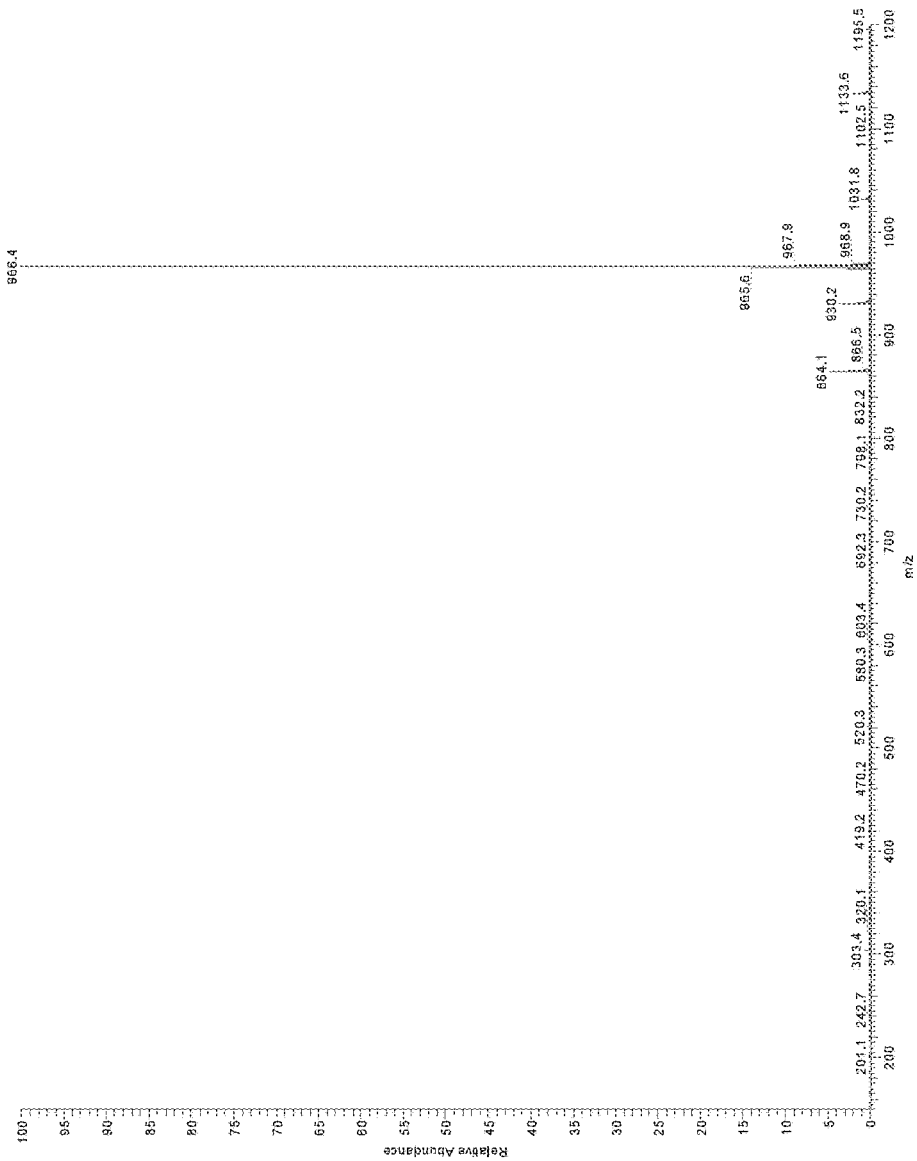
FIG. 38 is a mass spectrum of decitabine phosphooramidite building block (1d; $R_1$=phenoxyacetyl).

For example, when a protected 2'-deoxyguanosine-linked CPG solid support is (where $R_1$=tert-butyl phenoxyacetyl), which is coupled with 2-2.5 equivalents of phenoxyacetyl decitabine phosphoramidite (FIG. 2A, 1d, where $R_1$=phenoxyacetyl; see mass spectrum in FIG. 38) in the presence of 60% of 0.3 M benzylthiotetrazole activator (in acetonitrile) for 10 minutes. The CPG solid support containing protected DpG dinucleotide is treated with 20 mL of 50 mM $K_2CO_3$ in methanol for 1 hour and 20 minutes. The coupled product is oxidized, protective group removed, washed, filtered, and purified as described for GpD dinucleotide. The ESI-MS (−ve) of DpG dinucleotide 2b, where $X^+$=triethylammonium (calculated exact mass for the neutral compound $C_{18}H_{24}N_9O_{10}P$ is 557.14), exhibited m/z 556.1 [M-H]$^-$ and 1113.1 for [2M-H]$^-$ (see mass spectrum in FIG. 31). The DpG dinucleotide 2b, where $X^+$=sodium, is obtained by re-dissolving the triethylammonium salt in 4 ml water, 0.2 ml 2M $NaClO_4$ solution. When 36 mL acetone is added, the dinucleotide precipitates. The solution is kept at −20° C. for several hours and centrifugated at 4000 rpm for 20 minutes. The supernatant is discarded and the solid is washed with 30 mL acetone followed by an additional centrifugation at 4000 rpm for 20 minutes. The precipitate is dissolved in water and freeze dried, which exhibited m/z 556.0 [M-H]$^-$ (see mass spectrum in FIG. 36).

Figure 33:
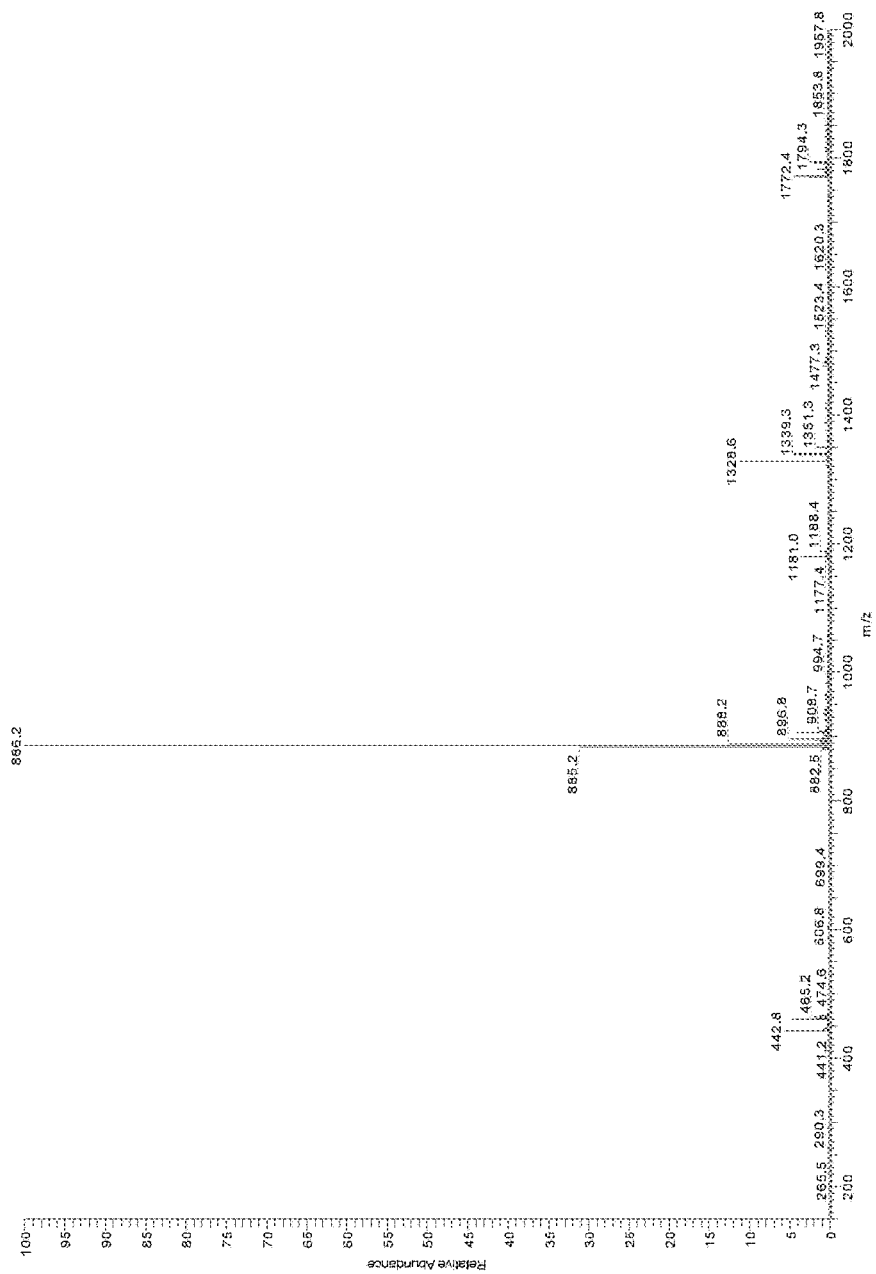
FIG. 33 is a mass spectrum of GpDpG (3c') triethylammonium salt.

When the cycle is repeated twice with 2-2.5 equivalents of tert-butyl phenoxyacetyl 2'-deoxyguanosine or phenoxyacetyl 5-aza-2'-deoxycytidine phosphoramidite in presence of 60% of 0.3 M benzylthiotetrazole activator (in acetonitrile) for 2.5 minutes and 10 minutes, respectively, the GpDpG trinucleotide 3c' is obtained, where $X^+$=triethylammonium (calculated exact mass for the neutral compound $C_{28}H_{36}N_{14}O_{16}P_2$ is 886.2), which exhibited m/z 885.16 [M-H]$^-$ (see mass spectrum FIG. 33).

Figure 34:
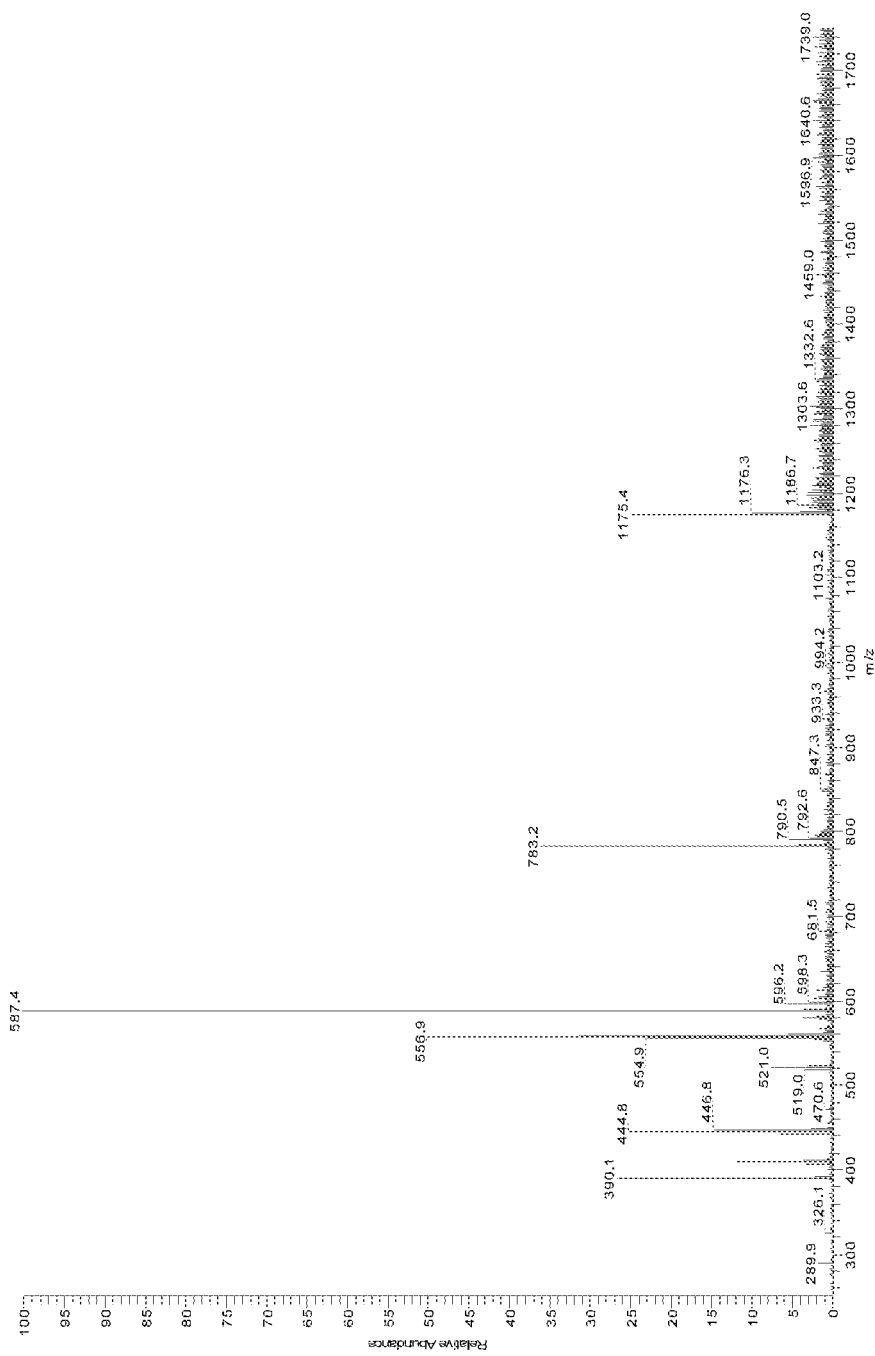
FIG. 34 is a mass spectrum of DpGpDpG (3c) triethylammonium salt.

When cycle is repeated three times, the DpGpDpG tetranucleotide 3c is obtained, where $X^+$=triethylammonium (calculated exact mass for the neutral compound $C_{36}H_{47}N_{18}O_{22}P_3$ is 1176.23), which exhibited m/z 587.4 for [M-2H]$^{2-}$ and 1175.4 [M-H]$^-$ (see mass spectrum in FIG. 34).

Figure 13:
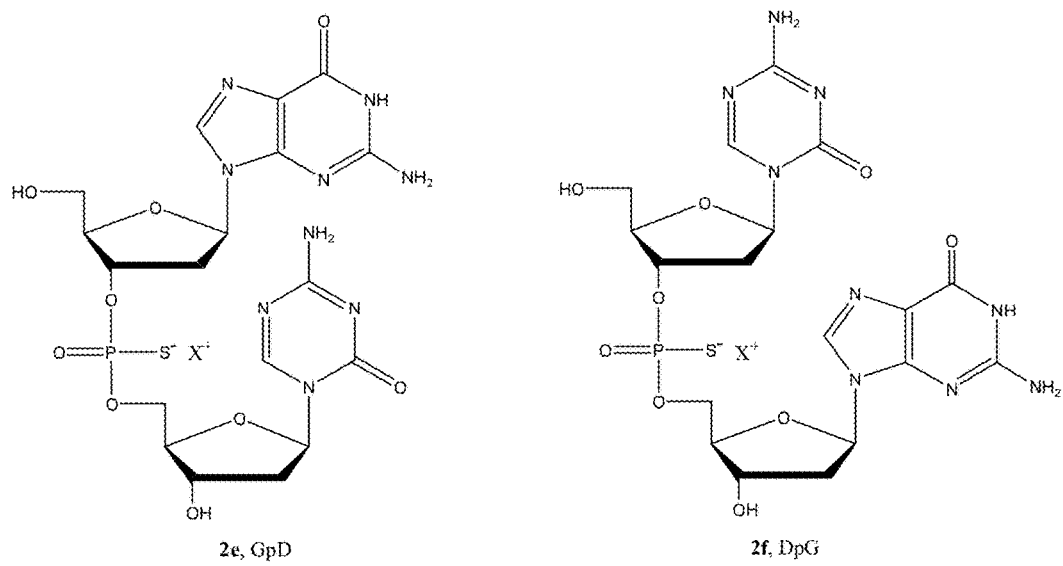
FIG. 13 depicts GpD and DpG dinucleotides with nuclease resistant phosphothioate linkage.
Figure 35:
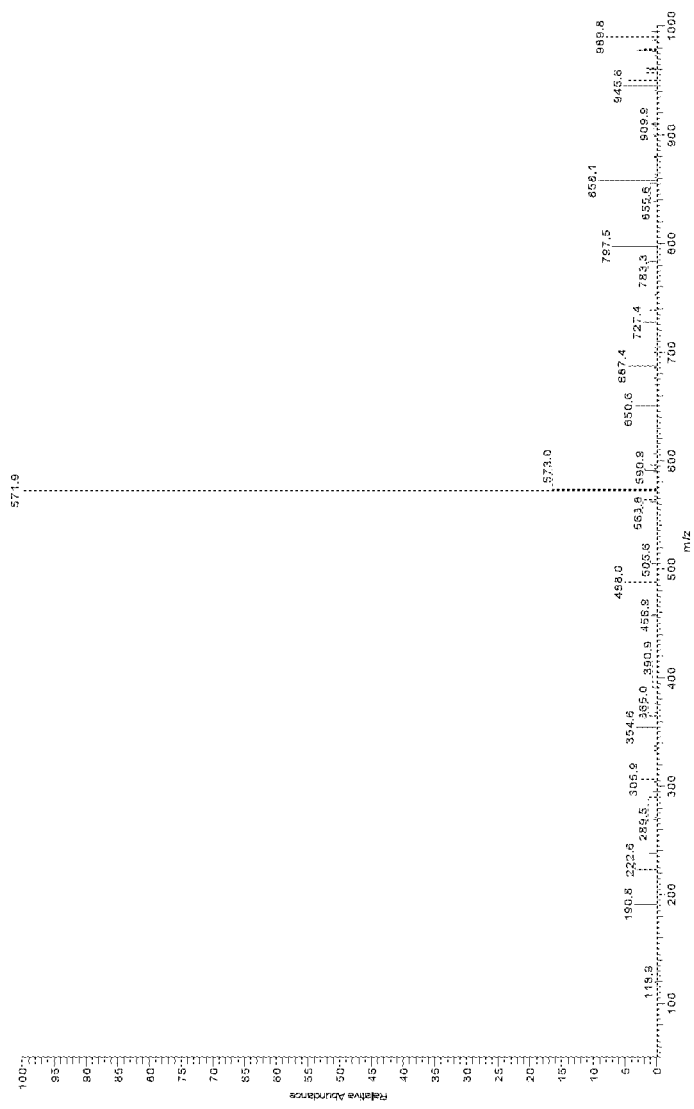
FIG. 35 is a mass spectrum of phosphorothioate linked DpG (20 triethylammonium salt.

When the phosphite triester, newly formed during the coupling step, is converted to the corresponding phosphorothioate triester with 5% phenylacetyl disulfide (PADS) in dichloroethane/sym collidine 4/1 (v/v), 4.3 mL solution (3.6 column volumes), flow rate 50 cm/h (contact time 3 column volumes), the phosphorothioate derivative of 2b can be obtained. The sulfurization is completed within 3 minutes, at which time excess reagent is removed from the reaction vessel by washing with acetonitrile. Subsequent deprotection and purification, as described for 2a, gives phosphorothioate DpG (Sp & Rp, FIG. 13, 2e), where X$^+$=triethylammonium (calculated exact mass for the neutral compound $C_{18}H_{24}N_9O_9P5$ is 573.12), which exhibited m/z 571.9 for [M-H]$^-$ (see mass spectrum in FIG. 35).

Figure 37:
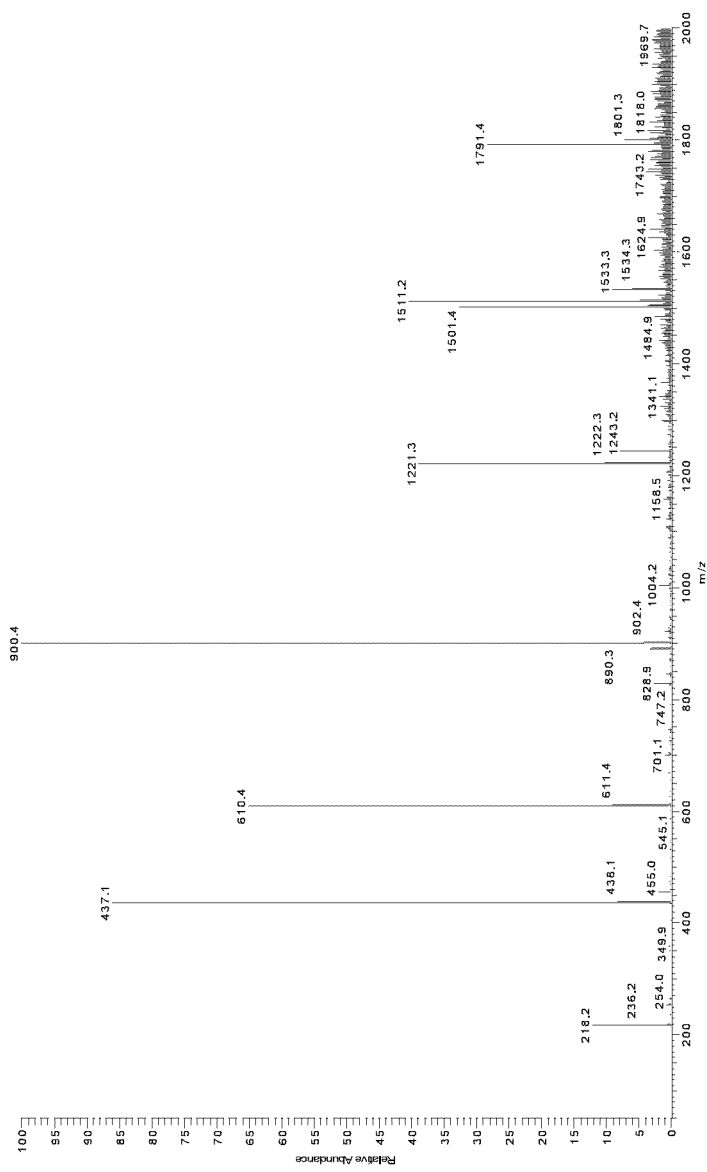
FIG. 37 is a mass spectrum of HIEG-DpG (2d) triethylammonium salt.

When cycle is repeated once with DMT hexaethyleneglycol phosphoramidite (60% activator, 7 min coupling time), followed by standard oxidation and purification as described for 2a, the HEG-DpG dinucleotide 2d is obtained (FIG. 12), where X$^+$=triethylammonium and Cap=hexaethyleneglycol phosphate (calculated exact mass for the neutral compound $C_{30}H_{49}N_9O_{19}P_2$ is 901.71), which exhibited m/z 900.4 [M-H]$^-$ (see mass spectrum in FIG. 37).

3. Inhibition of DNA Methylation by DpG and GpD Di-, Tri- and Tetranucleotides

Figure 25:
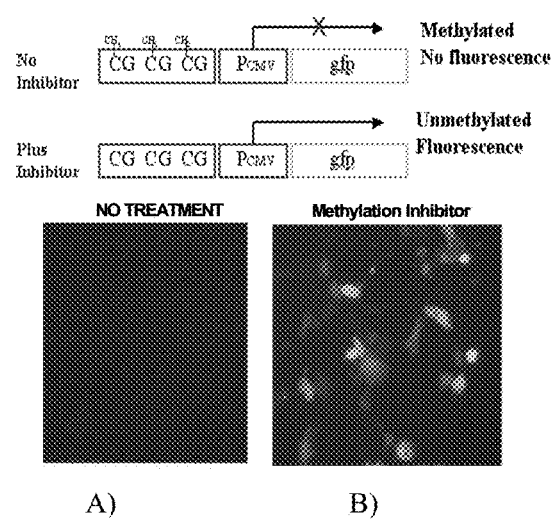
FIG. 25 schematically illustrates a cell-based GFP assay for DNA methylation Panel a) shows control cells; and panel b) cells treated with oligonucleotides of the present invention and expressing GFP.

The demethylating activity of DpG and GpD di-, tri-, and tetranucleotides were tested in a cell-based GFP (green fluorescent protein) assay. This assay, which is schematically illustrated in FIG. 25, has a GFP gene regulated by the CMV promoter and is sensitive to the methylation of CpG sites within the promoter. A decrease in methylation resulting from exposure to a methylation inhibitor leads to GFP expression and is readily scored. Specifically, the CMV-EE210 cell line containing the epigenetically silenced GFP transgene was used to assay for reactivation of GFP expression by flow cytometry. CMV-EE210 was made by transfecting NIH 3T3 cells with the pTR-UF/UF1/UF2 plasmid (Zolotuhin et al., 1996), which is comprised of pBS(+) (Stratagene, Inc.) containing a cytomegalovirus (CMV) promoter driving a humanized GFP gene adapted for expression in mammalian cells. After transfection, high-level GFP expressing cells were initially selected by FACS analysis and sorting using a MoFlo cytometer (Cytomation, Inc.). Decitabine, potent inhibitor of mammalian DNMT1, was used as a positive control. To screen for reactivation of CMV-EE210, decitabine (at 1 µM) or a test compound (at a concentration of 30-50 µM) was added to complete medium (phenol red free DMEM (Gibco, Life Technologies) supplemented with 10% fetal bovine serum (Hyclone)). Cells were then seeded to 30% confluence (~5000 cell/well) in 96 well plate containing the test compounds and grown for three days in at 37° C. in 5% $CO_2$. The plates were examined under a fluorescent microscope using a 450-490 excitation filter (13 filter cube, Leica, Deerfield Ill.). Wells were scored g1 positive if (10%) of viable cells express GFP, g2 positive if 30% of viable cells express GFP and g3 if >75% of the viable cells express GFP. GFP 50 is the concentration of an inhibitor that (like an $IC_{50}$) is the dose at which the GFP expression level goes from g3 to g1/2. Table 1 lists the results of the test for decitabine, DpG, GpD, GpDpG, DpGpGpD and DpGpDpG as DNA methylation inhibitors. As shown in Table 1, all of the 5 oligonucleotide analogues tested were able to inhibit DNA methylation effectively at low concentrations, resulting in reactivation of the transcription of the GFP gene.

TABLE 1

Preliminary screening of demethylating activity

| Compound | GFP Expression Level | IC 50 (nM) |
| --- | --- | --- |
| Decitabine | g3 | 500 |
| DpG | g3 | 400 |
| GpD | g3 | 700 |
| GpDpG | g3 | 1800 |
| DpGpGpD | g3 | 1100 |
| DpGpDpG | g3 | 1400 |

4. Synthesis of DpG and GpD Dinucleotides and Tetranucleotides in Solution

Figure 10:
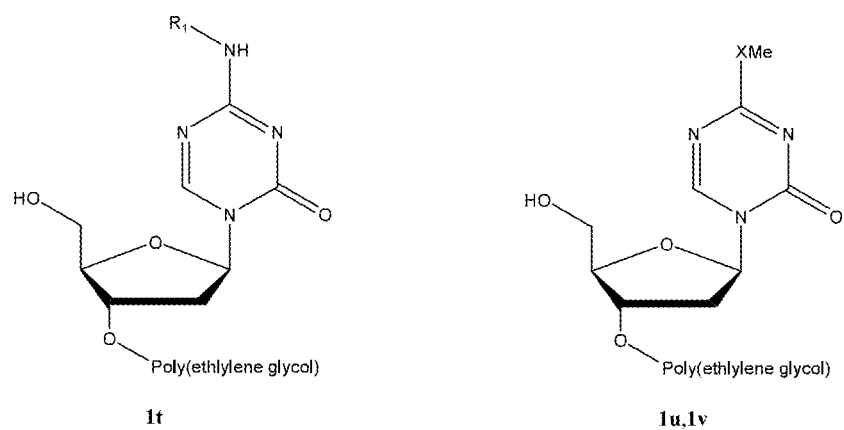
FIG. 10 depicts protected decitabine 3'-linked onto poly (ethylene glycol).

For the synthesis of these oligonucleotides in large scale, the use of soluble polymeric supports is desirable. Bayer and Mutter, (1972) Nature 237: 512-513; Bonora (1995) Appl. Biochem. Biotechnol. 54: 3-17. The polymer support poly (ethylene glycol) or PEG allows synthetic process to be carried out in a homogeneous phase and assures an easy intermediate purification step through simple precipitation-and-filtration procedures. Harris Poly(ethylene glycol) Chemistry. Biotechnical and Biomedical Applications, J. M. Harris (Ed.), Plenum Press, New York (USA), 1992, pp. 1-14 [book citation]. For example, 3'-linked derivatives such as 1t, 1u, or 1v (FIG. 10) can be easily adapted to the standard phosphoramidite-based chemistry employed in the preceding solid-phase procedures to give the DpG and GpD di- and tetranucleotides 2a, 2b, 3a, 3b. 3e, 3d.

Alternatively, the novel DpG dinucleotide 2a can be prepared in solution by coupling derivatives 1p, 1q, or 1r with similarly based protected 5'-O-DMTr 2'-deoxyguanosine-3'-O-cyanoethyl-N,N-diisopropylphosphoramidite and GpD from the coupling of similarly 3'-protected 2'-deoxyguanosine with 5'-O-DMTr 2'-deoxy-5-aza-cytidine-3'-O-cyanoethyl-N,N-diisopropylphosphoramidites (1d, 1e or 1f) in acetonitrile and/or dichloromethane, followed by oxidation with iodine/water, deprotection of the base protective groups, and removal of the DMTr group (as in the standard cycle for oligonucleotide synthesis).

Figure 11:
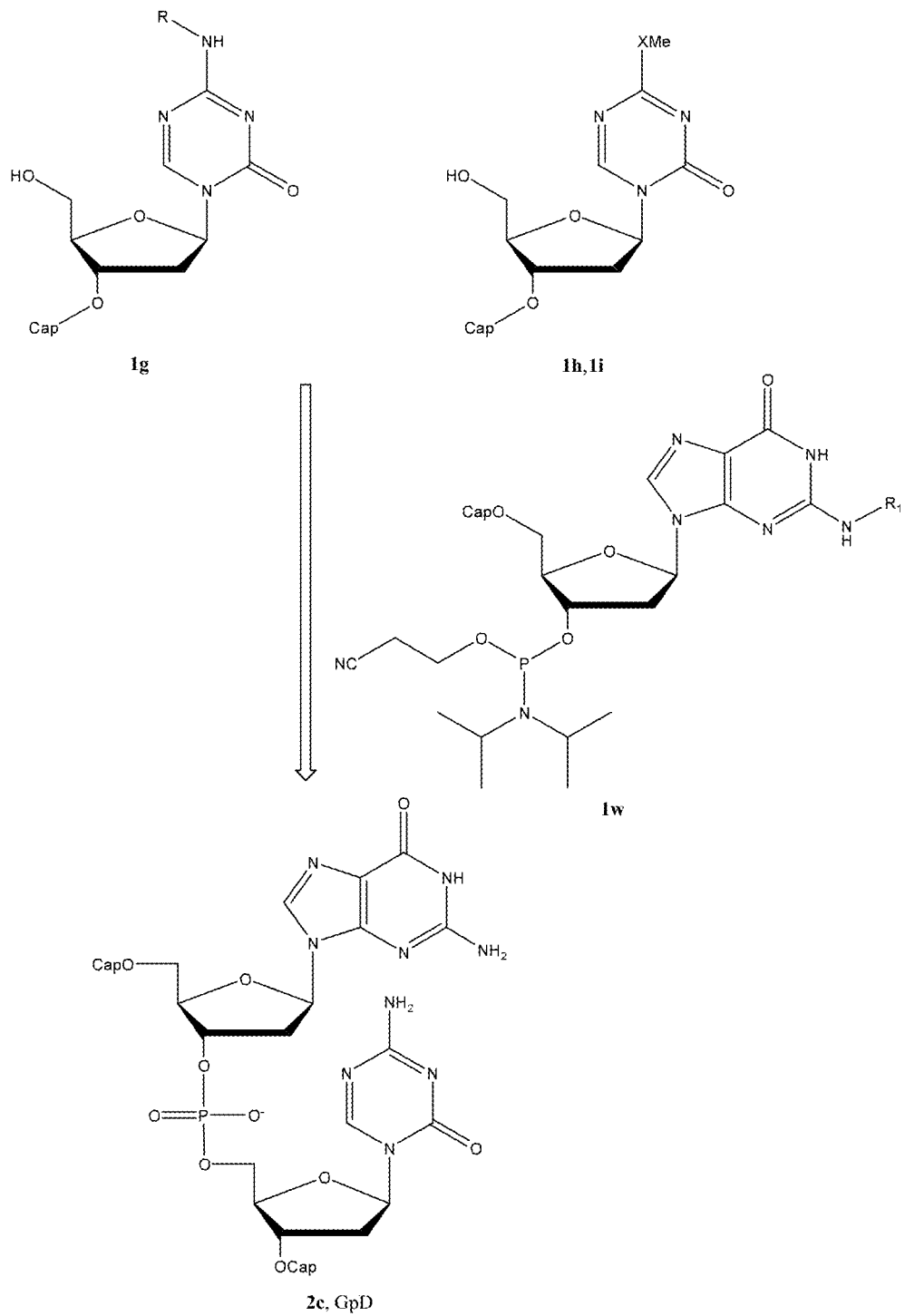
FIG. 11 shows synthesis schemes of 3'- and 5'-O-capped GpD dinucleotide.
Figure 12:
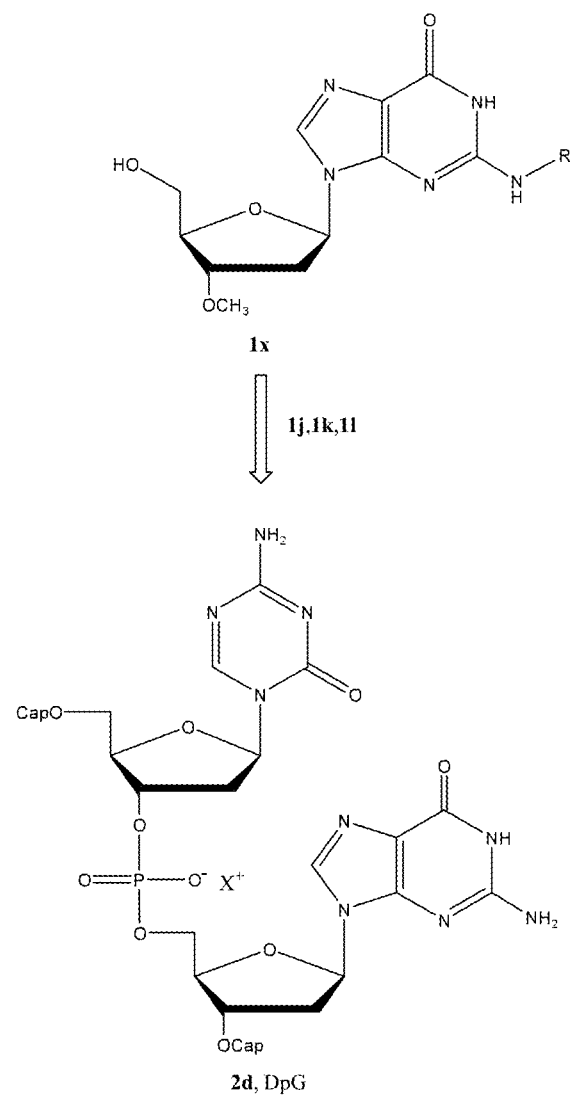
FIG. 12 shows synthesis schemes of 3'- and 5'-O-capped DpG dinucleotide.

In addition, the novel DpG (2c) dinucleotide with the terminal 3'-OH and 5'-OH capped with methyl group can be prepared by coupling 3'-O-methyl derivative 1g, 1h or 1i with a 5'-O-methyl derivative of 2'-deoxyguanosine-3'-O-cyanoethyl-N,N-diisopropylphosphoramidite 1w (FIG. 11), followed by oxidation with iodine/water, deprotection of the base protective groups, and removal of the DMTr group (as in the standard cycle for oligonucleotide synthesis). Dinucleotide GpD (2d) can likewise be prepared by coupling 3'-O-methyl 2'-deoxyguanosine derivative 1x with 5'-O-methyl derivative of 2'-5-azacytidine-3'-O-cyanoethyl-N,N-diisopropylphosphoramidite 1j, 1k or 1l (FIG. 12).

Figure 14:
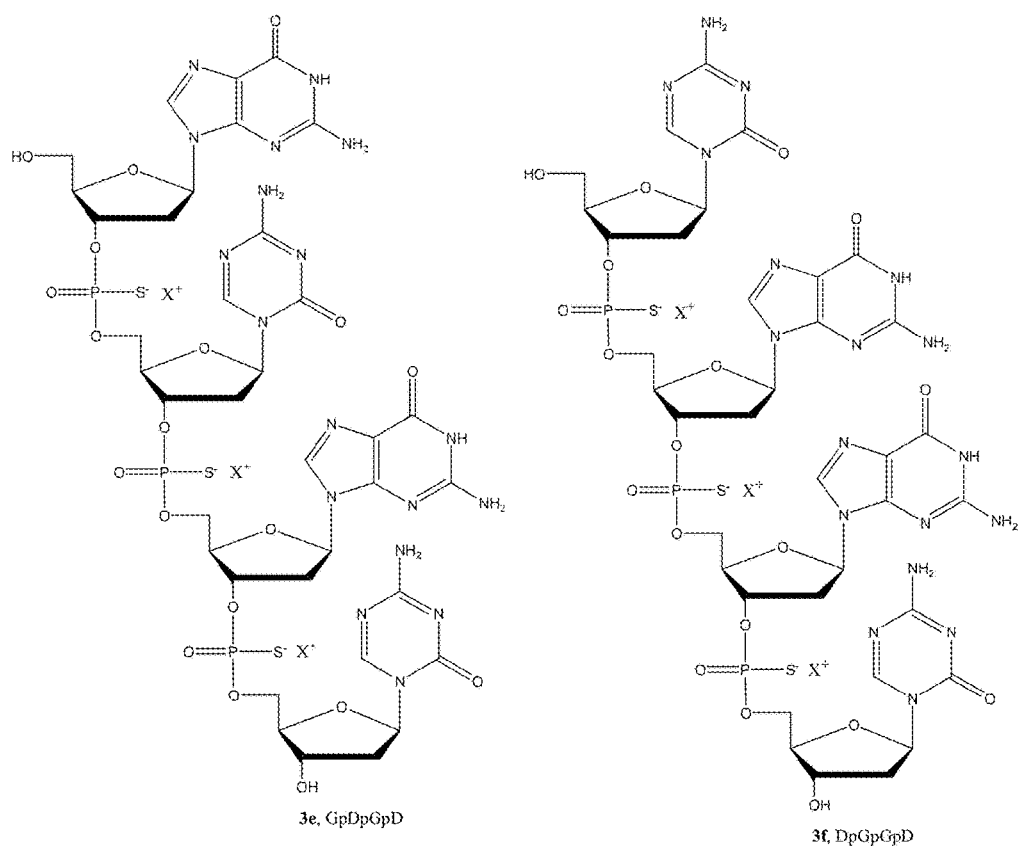
FIG. 14 depicts GpDpGpD and DpGpGpD tetranucleotides with nuclease resistant phosphothioate linkage.
Figure 15:
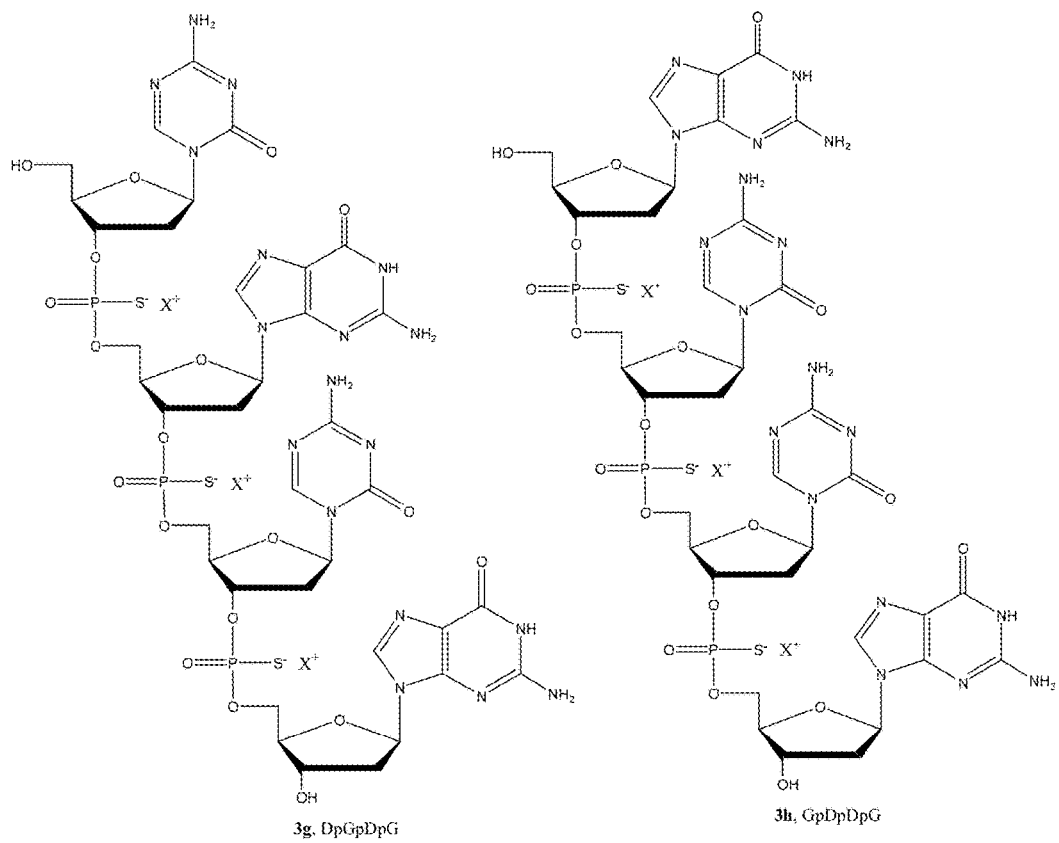
FIG. 15 depicts DpGpDpG and GpDpGpD tetranucleotides with nuclease resistant phosphothioate linkage.
Figure 16:
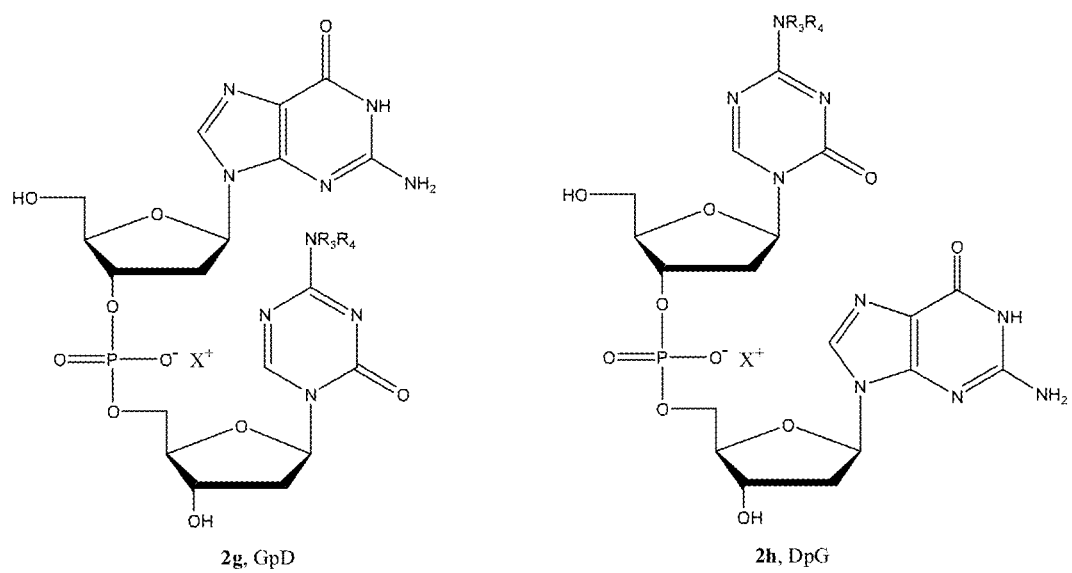
FIG. 16 depicts GpD and DpG dinucleotides with cytidine deaminase resistant 4-amino groups.
Figure 17:
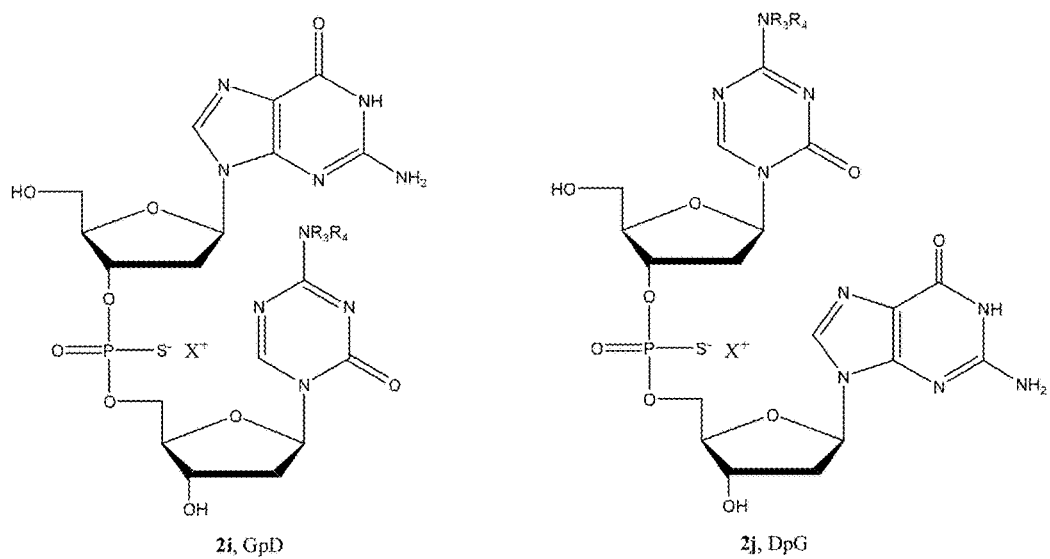
FIG. 17 depicts GpD and DpG dinucleotides with cytidine deaminase resistant 4-amino groups and nuclease resistant phosphothioate linkage
Figure 18:
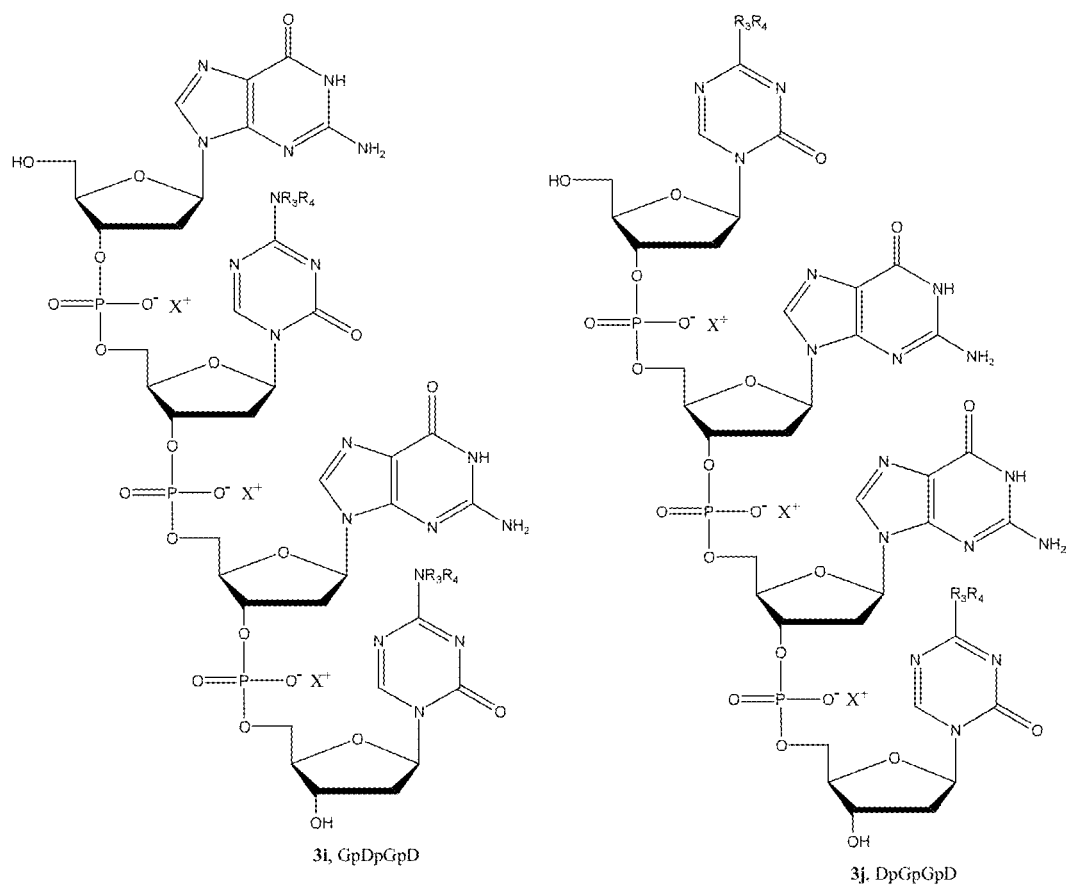
FIG. 18 depicts GpDpGpD and DpGpGpD tetranucleotides with cytidine deaminase resistant 4-amino groups.
Figure 19:
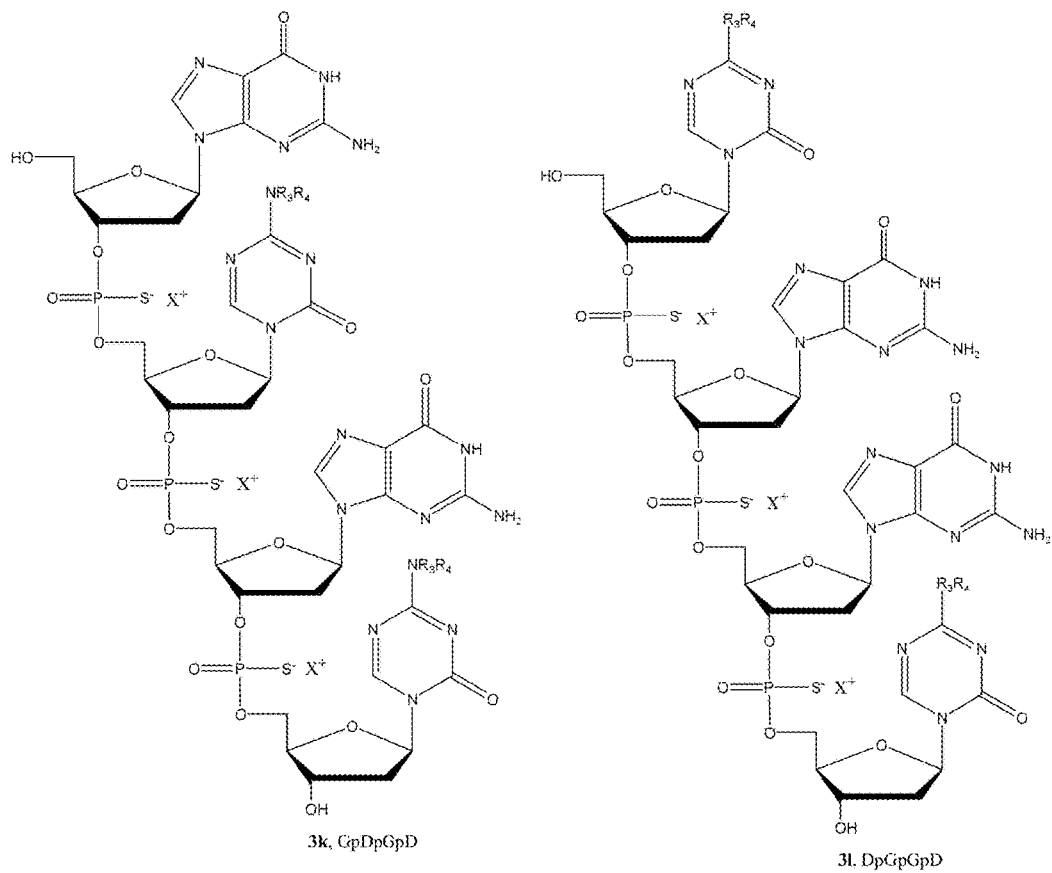
FIG. 19 depicts GpDpGpD and DpGpGpD tetranucleotides with cytidine deaminase resistant 4-amino groups and nuclease resistant phosphothioate linkage.
Figure 20:
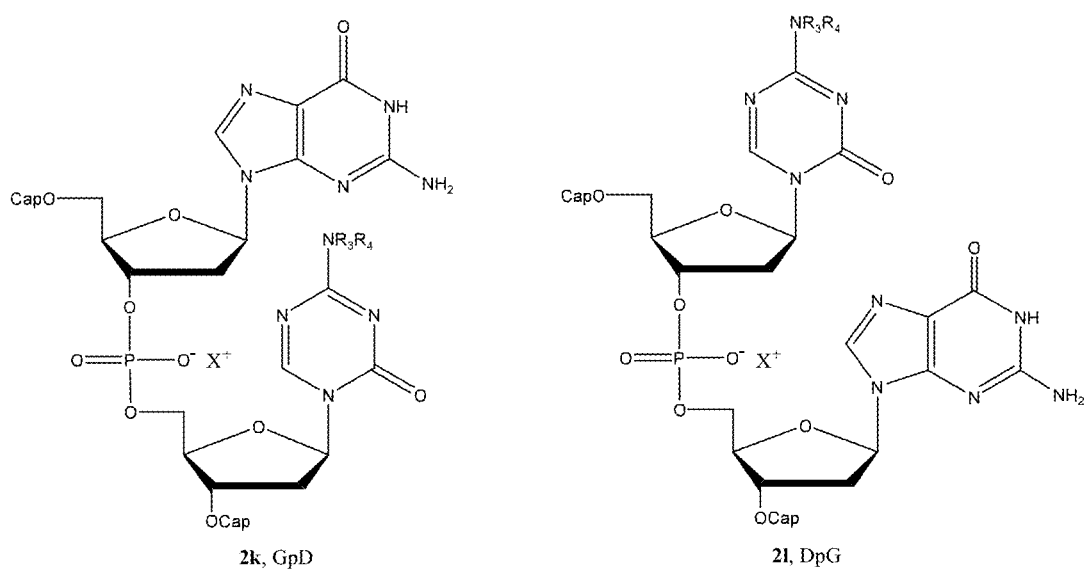
FIG. 20 depicts Cap-O-GpD-O-Cap and Cap-O-DpG-O-Cap dinucleotides with cytidine deaminase resistant 4-amino groups.
Figure 21:
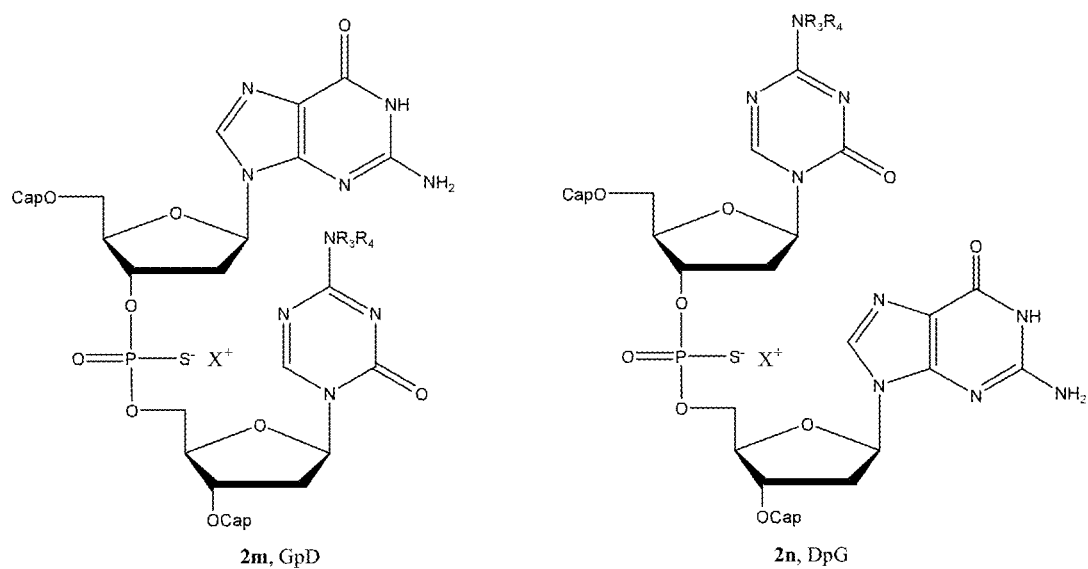
FIG. 21 depicts Cap-O-GpD-O-Cap and Cap-O-DpG-O-Cap dinucleotides with cytidine deaminase resistant 4-amino groups and nuclease resistant phosphothioate linkage.
Figure 22:
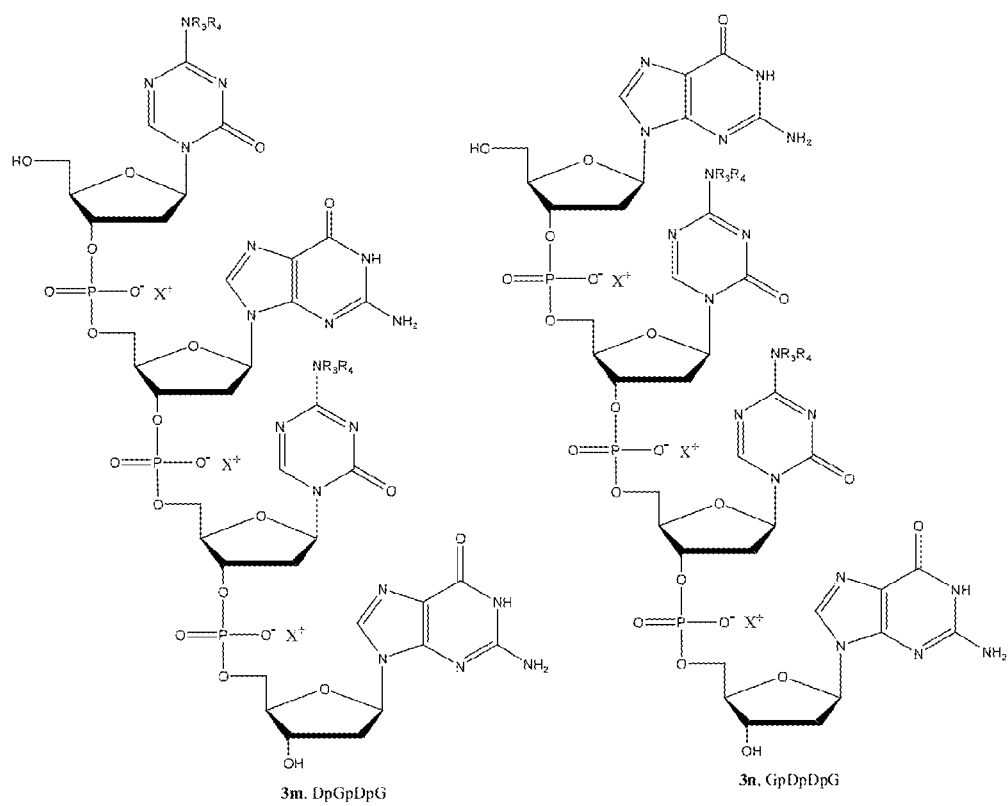
FIG. 22 depicts DpGpDpG and GpDpGpD tetranucleotides with cytidine deaminase resistant 4-amino groups.
Figure 23:
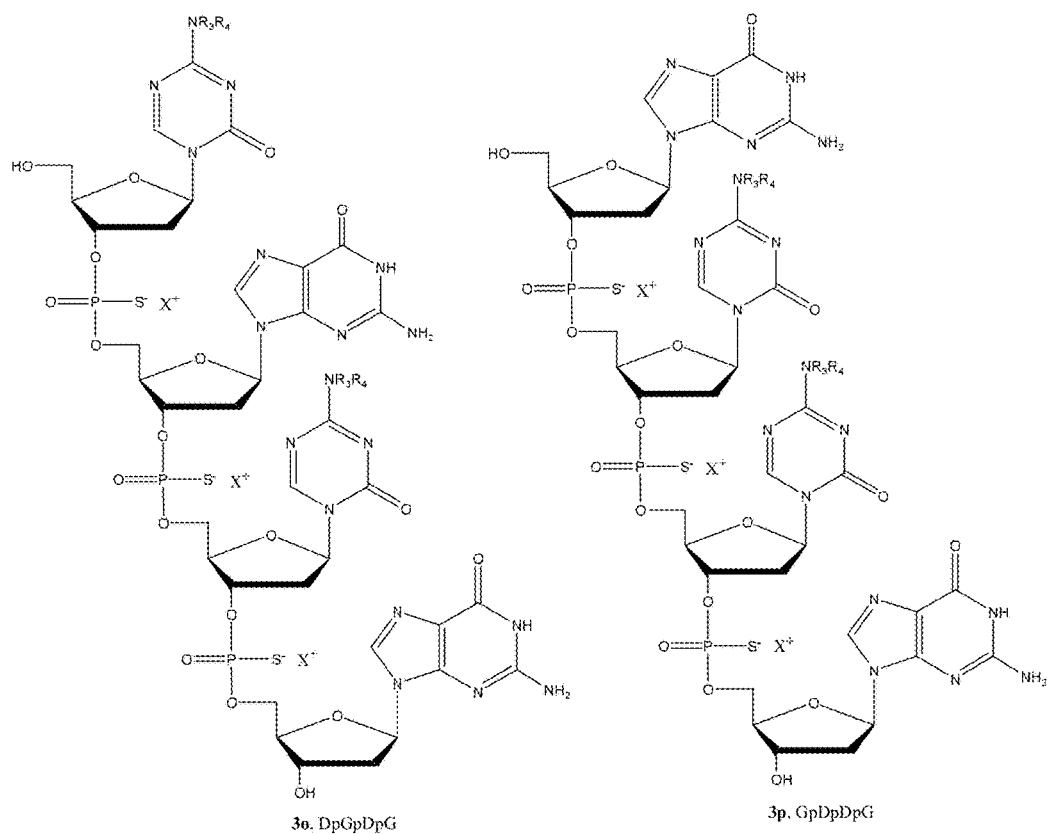
FIG. 23 depicts DpGpDpG and GpDpGpD tetranucleotides with cytidine deaminase resistant 4-amino groups and nuclease resistant phosphothioate linkage

5. Synthesis of DpG and GpD Oligonucleotides Resistant to Cytidine Deaminases and Nucleases In general, oligonucleotides in biological fluids are subject to nuclease degradation. Stein and Cheng (1993) Science 261: 1004-1012; Cohen (1994) Adv. Pharmacol. 25: 319-339. To increase stability and resistance to nuclease degradation phosphothioate dinucleotide and tetranucleotide derivatives such as 2e, 2f, 3e, 3f, 3g, and 3h (FIGS. 13, 14 and 15) are also made, where the internucleotide non-bridging oxygen is replaced with sulfur. Standard phosphoramidite protocols are used, except for the substitution of bis(O,O-diisopropoxy phosphinothioyl) disulfide (S-tetra) for iodine during the oxidation step. Zon and Stec (1991) In Eckstein, F. (ed.), 'Phosphorothioate Analogues' in Oligonucleotides and Their Analogs: A Practical Approach. IRL Press, pp. 87-108; Zon, G. (1990) In Hancock, W. S. (ed.), High Performance Liquid Chromatography in Biotechnology. Wiley, New York, Ch. 14, pp. 310-397 [book citations]; Stec, Uznanski, Wilk, Hirschbein, Fearon, and Bergot (1993) Tet. Lett. 34: 5317-5320; Iyer, Phillips, Egan, Regan, and Beaucage (1990) J. Org. Chem. 55: 4693-4699.

Another potential hindrance to the application of these oligonucleotides as pharmaceuticals is the ubiquitous presence of cytidine deaminase (CDA) since deamination of decitabine results in total loss of activity. Momparler, Cote and Eliopoulos (1997) Leukemia 11 (Supp1.1): 1-6; Chabot, Bouchard and Momparler (1983) Biochem. Pharmacol. 32: 1327-1328; Laliberte, Marquez and Momparler (1992) Cancer Chemother. Pharmacol. 30: 7-11. To address this problem, the oligonucleotides containing decitabine derivatives with the 4-$NH_2$ is replaced by 4-$NR_3R_4$ (where $R_3$ and $R_4$ can be alkyl, alkyl amine, and alkyl alcohol) are also prepared to give derivatives such as 2g, 2h, 2i, 2j, 2k, 2l, 2m, 2n, 3i, 3j, 3k, 3, 3m, 3n, 3o, and 3p (FIGS. 16, 17, 18, 19, 20 and 21). Standard phosphoramidite protocols are used, except for the substitution of alkyl amines, alkyl diamines, and hydroxyl amines for ammonia in methanol during the removal of 4-methoxy and 4-methylthio. Since secondary and tertiary amines, diamines, and hydroxyl amines make worse leaving groups than ammonia, these derivatives are more difficult to deaminate.

6. Synthesis of DpG and GpD-Rich Oligonucleotides Based on the CpG Islands of the Promoter Regions of Cancer Related Genes Such as P15 (CDKN2B), BRCA1, and P16 (CDKN2A)

Oligonucleotide analogues rich in DpG and GpD islets that range in length from 5 to 100 bases can be prepared, where D can be decitabine or decitabine analogues. Unlike the above described DpG and GpD dinucleotides and tetranucleotides, these relatively longer DpG and GpD-rich oligonucleotide analogues not only function restrictively within the CpG islands of the promoter regions but specific to a segment within the promoter region sequence for cancer related genes such as P15 (CDKN2B), P16 (CDKN2A) and BRAC1. For examples, 8-mer, 10-mer, and 12-mer DpG and GpD-rich oligonucleotide analogues (FIG. 26) based on the P15, P16, and BRCA1 promoter region sequences (FIGS. 27, 28 and 29, respectively) can be prepared by using phosphoramidite building block 1d, 1e or 1f in a standard solid phase oligonucleotide synthesis. More examples of oligonucleotides that can be modified to incorporate 5-aza-cytosine therein are listed in FIGS. 27, 28 and 29. These oligonucleotide analogues can function like primers and get incorporated into replicating DNA only at that specific segment of the promoter region sequence of P15, P16 or BRAC1, thus effectively and selectively inhibiting methylation of the promoter region.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of treating a condition, the method comprising administering to a subject in need thereof a therapeutically-effective amount of a dinucleotide analogue, or a pharmaceutically-acceptable salt thereof, wherein the dinucleotide analogue, or the pharmaceutically-acceptable salt thereof, is of the formula: 5'-DpG-3' or 5'-GpD-3', wherein D is decitabine; p is a phospholinker; and G is deoxyguanosine, wherein the number of phosphorus atoms in the phospholinker is one, wherein the linker is not a phosphorothioate linker.

2. The method of claim 1, wherein the dinucleotide analogue is the pharmaceutically-acceptable salt, wherein the pharmaceutically-acceptable salt is a sodium salt.

3. The method of claim 1, wherein the dinucleotide analogue or the pharmaceutically-acceptable salt thereof is formulated for oral administration.

4. The method of claim 1, wherein the dinucleotide analogue or the pharmaceutically-acceptable salt thereof is formulated for subcutaneous administration.

5. The method of claim 1, wherein the dinucleotide analogue or the pharmaceutically-acceptable salt thereof is formulated for intravenous administration.

6. The method of claim 1, wherein the dinucleotide analogue or the pharmaceutically-acceptable salt thereof binds to a DNA methyltransferase.

7. The method of claim 1, wherein the dinucleotide analogue or the pharmaceutically-acceptable salt thereof inhibits DNA methylation.

8. The method of claim 7, wherein the inhibition of DNA methylation increases expression of a gene.

9. The method of claim 1, wherein the dinucleotide analogue or the pharmaceutically-acceptable salt thereof binds to a promoter region of a gene.

10. The method of claim 9, wherein the gene is a tumor suppressor gene.

11. The method of claim 1, wherein the condition is a hematological condition.

12. The method of claim 11, wherein the hematological condition is acute myeloid leukemia.

13. The method of claim 11, wherein the hematological condition is acute promyelocytic leukemia.

14. The method of claim 11, wherein the hematological condition is chronic myelogenous leukemia.

15. The method of claim 1, wherein the condition is cancer.

16. The method of claim 1, wherein the subject is human.

17. A method of treating a condition, the method comprising administering to a subject in need thereof a therapeutically-effective amount of a dinucleotide analogue, or a pharmaceutically-acceptable salt thereof, wherein the dinucleotide analogue, or the pharmaceutically-acceptable salt thereof, is of the formula: 5'-DpG-3' or 5'-GpD-3', wherein D is decitabine; p is a phospholinker; and G is deoxyguanosine, wherein the number of phosphorus atoms in the dinucleotide analogue is one.

18. The method of claim 17, wherein the dinucleotide analogue is the pharmaceutically-acceptable salt, wherein the pharmaceutically-acceptable salt is a sodium salt.

19. The method of claim 17, wherein the dinucleotide analogue or the pharmaceutically-acceptable salt thereof is formulated for oral administration.

20. The method of claim 17, wherein the dinucleotide analogue or the pharmaceutically-acceptable salt thereof is formulated for subcutaneous administration.

21. The method of claim 17, wherein the dinucleotide analogue or the pharmaceutically-acceptable salt thereof is formulated for intravenous administration.

22. The method of claim 17, wherein the dinucleotide analogue or the pharmaceutically-acceptable salt thereof binds to a DNA methyltransferase.

23. The method of claim 17, wherein the dinucleotide analogue or the pharmaceutically-acceptable salt thereof inhibits DNA methylation.

24. The method of claim 23, wherein the inhibition of DNA methylation increases expression of a gene.

25. The method of claim 17, wherein the dinucleotide analogue or the pharmaceutically-acceptable salt thereof binds to a promoter region of a gene.

26. The method of claim 25, wherein the gene is a tumor suppressor gene.

27. The method of claim 17, wherein the condition is a hematological condition.

28. The method of claim 27, wherein the hematological condition is acute myeloid leukemia.

29. The method of claim 27, wherein the hematological condition is acute promyelocytic leukemia.

30. The method of claim 27, wherein the hematological condition is chronic myelogenous leukemia.

31. The method of claim 17, wherein the condition is cancer.

32. The method of claim 17, wherein the subject is human.

33. A method of treating a hematological condition, the method comprising administering to a subject in need thereof a therapeutically-effective amount of a dinucleotide analogue, or a pharmaceutically-acceptable salt thereof, wherein the dinucleotide analogue, or the pharmaceutically-acceptable salt thereof, is of the formula: 5'-DpG-3' or 5'-GpD-3', wherein D is decitabine, p is a phospholinker, and G is deoxyguanosine, wherein the number of phosphorus atoms in the phospholinker is one.

34. The method of claim 33, wherein the dinucleotide analogue is the pharmaceutically-acceptable salt, wherein the pharmaceutically-acceptable salt is a sodium salt.

35. The method of claim 33, wherein the dinucleotide analogue or the pharmaceutically-acceptable salt thereof is formulated for oral administration.

36. The method of claim 33, wherein the dinucleotide analogue or the pharmaceutically-acceptable salt thereof is formulated for subcutaneous administration.

37. The method of claim 33, wherein the dinucleotide analogue or the pharmaceutically-acceptable salt thereof is formulated for intravenous administration.

38. The method of claim 33, wherein the dinucleotide analogue or the pharmaceutically-acceptable salt thereof binds to a DNA methyltransferase.

39. The method of claim 33, wherein the dinucleotide analogue or the pharmaceutically-acceptable salt thereof inhibits DNA methylation.

40. The method of claim 39, wherein the inhibition of DNA methylation increases expression of a gene.

41. The method of claim 33, wherein the dinucleotide analogue or the pharmaceutically-acceptable salt thereof binds to a promoter region of a gene.

42. The method of claim 41, wherein the gene is a tumor suppressor gene.

43. The method of claim 33, wherein the hematological condition is acute myeloid leukemia.

44. The method of claim 33, wherein the hematological condition is acute promyelocytic leukemia.

45. The method of claim 33, wherein the hematological condition is chronic myelogenous leukemia.

46. The method of claim 33, wherein the subject is human.

* * * * *

SEQUENCE LISTING

```
<160> NUMBER OF SEQ ID NOS: 33

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-aza-cytosine
<220> FEATURE:
<221> NAME/KEY: modified_base
<222> LOCATION: (5)..(5)
<223> OTHER INFORMATION: 5-aza-cytosine

<400> SEQUENCE: 1 ttcgcgaa                                                                   8

<210> SEQ ID NO 2
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 5-aza-cytosine

<400> SEQUENCE: 2
``` tgcctcgt                                                                  8

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 5-aza-cytosine
<220> FEATURE:
<221> NAME/KEY: modified_base
<222> LOCATION: (9)..(9)
<223> OTHER INFORMATION: 5-aza-cytosine

<400> SEQUENCE: 3
aggcacagca                                                                10

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: 5-aza-cytosine
<220> FEATURE:
<221> NAME/KEY: modified_base
<222> LOCATION: (7)..(7)
<223> OTHER INFORMATION: 5-aza-cytosine

<400> SEQUENCE: 4 gtgcagca                                                                  8

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-aza-cytosine
<220> FEATURE:
<221> NAME/KEY: modified_base
<222> LOCATION: (7)..(7)
<223> OTHER INFORMATION: 5-aza-cytosine
<220> FEATURE:
<221> NAME/KEY: modified_base
<222> LOCATION: (10)..(10)
<223> OTHER INFORMATION: 5-aza-cytosine

<400> SEQUENCE: 5
aacgggcggc gg                                                             12

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (3)..(3)
<223> OTHER INFORMATION: 5-aza-cytosine
<220> FEATURE:
<221> NAME/KEY: modified_base
<222> LOCATION: (6)..(6)
<223> OTHER INFORMATION: 5-aza-cytosine
<220> FEATURE:
<221> NAME/KEY: modified_base
<222> LOCATION: (8)..(8)
<223> OTHER INFORMATION: 5-aza-cytosine

<400> SEQUENCE: 6
cacggcgcgg                                                             10

<210> SEQ ID NO 7
<211> LENGTH: 2144
<212> TYPE: DNA
<213> ORGANISM: Homo sapiens

<400> SEQUENCE: 7 ttttttcattc agtcaacttg cttcgcgaag ctcacacatc tgcctcgtgc aagattctca      60
gtcattttac ttagtcattg gttctttccc tatcaccatt ctttatgtcc ccctcaaaga     120
aaaacattat cttccatttc cttatcaact ccaaacagct ttcatttttc tgacatattt     180
actacctaag aaaatggctc aagaattggg tagactatct tgtcctaact tttctgataa     240
gtttcagaga aactcaaagg tcaaaacaag agcataagag taaaggtaga gaaattaaga     300
aactgaagac taggaaatgg gggttgggat gggaagaaa aagaaattgt tataatgcta     360
cccggttccc ttccctgtcc aggtggattt cagctctgtt gaggctctgt cagtagatat     420
tcagccctaa ccagcacttc catggtggtg gcacttccac tgccctttaa aagaaagagc     480
tttttttaat tctacaggga tttggggat gaggagtcag agctaaggta tcctaaaaaa     540
aacatgtgaa gactctcatt ttgcaataca caagcaattg ccctcctgtt aagactttgt     600
cttcctcagc actccgaacc aaatgattc tgtaaacaaa aattgttcac ttttaggaga     660
ggtccactta tgcagttcct caccaaagtt tttaggcaac aaatccataa cttgcggttc     720
tcttcctatc caatgtagca tccgctgaaa tgttttaaat attttaagta ataaatgttg     780
attcaaactc acctaggaag attaggaagg ggaaaaaaag cacttggcat ttaaatcttc     840
agaagagaat ttaatgacag gttcagcctg tttaatgaca agcccagcac cacacccctc     900
tcttatgatg tttcattatt actgcataaa tttcctttat tactcatgat aaataaaaat     960
aagatacctg acaaagtggg tttaaatagg taagagtgca aacaaagatt tactgtacaa    1020
atatgatgaa actgggatct cagattctta agtataatt tttttttgtct tatgtgtgcc    1080 aggttgccac tctcaatctc gaactagttt ttttctcttt taagggttgt atccataatg    1140
caaaaatgga aagaattaaa aagcacacgc aaaaacatgat tctcgggatt tttctctatt    1200
tttatggttg actaattcaa acagaaagac acatccaaga gaaaattgct aagtttgata    1260
caagttatga aacttgtgaa gcccaagtac tgcctgggga tgaatttaac ttgtatgaca    1320
ggtgcagagc tgtcgctttc agacatctta agaaagacgg agttattttg aatgactttc    1380
tctcggtcac aagggagcca ccaacgtctc cacagtgaaa ccaactggct ggctgaagga    1440
acagaaatcc tctgctccgc ctactgggga ttaggagctg agggcagtgg tgaacattcc    1500
caaaatatta gccttggctt tactggacat ccagcgagca gtgcagccag cattcctggc    1560
ggctccctgg cccagtctct ggcgcatgcg tcctagcatc tttgggcagg cttccccgcc    1620
ctcgtgacgc gtcggcccgg gcctggcctc ccggcgatca cagcggacag ggggcggagc    1680
```

```
ctaaggggt gggagacgc cggccccttg gcccagctga aaacggaatt ctttgccggc    1740
tggctcccca ctctgccaga gcgaggcggg gcagtgagga ctccgcgacg cgtccgcacc    1800
ctgcggccag agcggctttg agctcggctg cgtccgcgct aggcgctttt tcccagaagc    1860
aatccaggcg cgcccgctgg ttcttgagcg ccaggaaaag cccggagcta acgaccggcc    1920
gctcggccac tgcacggggc cccaagccgc agaaggacga cgggagggta atgaagctga    1980
gcccaggtct cctaggaagg agagagtgcg ccggagcagc gtgggaaaga agggaagagt    2040
gtcgttaagt ttacggccaa cggtggatta tccgggccgc tgcgcgtctg ggggctgcgg    2100
aatgcgcgag gagaacaagg gcatgcccag tgggggcggc agcg                    2144
```

<210> SEQ ID NO 8
<211> LENGTH: 8
<212> TYPE: DNA
<213> ORGANISM: Homo sapiens

<400> SEQUENCE: 8 ttcgcgaa                                                            8

<210> SEQ ID NO 9
<211> LENGTH: 8
<212> TYPE: DNA
<213> ORGANISM: Homo sapiens

<400> SEQUENCE: 9 tgcctcgt                                                            8

<210> SEQ ID NO 10
<211> LENGTH: 8
<212> TYPE: DNA
<213> ORGANISM: Homo sapiens

<400> SEQUENCE: 10 tgccggct                                                            8

<210> SEQ ID NO 11
<211> LENGTH: 8
<212> TYPE: DNA
<213> ORGANISM: Homo sapiens

<400> SEQUENCE: 11 cggcccgg                                                            8

<210> SEQ ID NO 12
<211> LENGTH: 8
<212> TYPE: DNA
<213> ORGANISM: Homo sapiens

<400> SEQUENCE: 12 gctcggct                                                            8

<210> SEQ ID NO 13
<211> LENGTH: 987
<212> TYPE: DNA
<213> ORGANISM: Homo sapiens

<400> SEQUENCE: 13

```
cggagagggg gagaacagac aacgggcggc ggggagcagc atggagccgg cggcggggag    60
cagcatggag ccttcggctg actgctggca cacggccgcg gcccgggtc gggtagagga    120 ggtgcgggcg ctgctggagg cgggggcgct gcccaacgca ccgaatagtt acggtcggag    180
```

```
gccgatccag gtcatgatga tgggcagcgc ccgagtggcg gagctgctgc tgctccacgg    240
cgcggagccc aactgcgccg accccgccac tctcacccga cccgtgcacg acgctgcccg    300
ggagggcttc ctggacacgc tggtggtgct gcaccgggcc ggggcgcggc tggacgtgcg    360
cgatgcctgg ggccgtctgc ccgtggacct ggctgaggag ctgggccatc gcgatgtcgc    420
acggtacctg cgcgcggctg cggggggcac cagaggcagt aaccatgccc gcatagatgc    480
cgcggaaggt ccctcagaca tccccgattg aaagaaccag agaggctctg agaaacctcg    540
ggaaacttag atcatcagtc accgaaggtc ctacagggcc acaactgccc ccgccacaac    600
ccaccccgct ttcgtagttt tcatttagaa aatagagctt ttaaaaatgt cctgcctttt    660
aacgtagata taagccttcc cccactaccg taaatgtcca tttatatcat ttttatata    720 ttcttataaa aatgtaaaaa agaaaaacac cgcttctgcc ttttcactgt gttggagttt    780
tctggagtga gcactcacgc cctaagcgca cattcatgtg ggcatttctt gcgagcctcg    840
cagcctccgg aagctgtcga cttcatgaca agcattttgt gaactaggga agctcagggg    900
ggttactggc ttctcttgag tcacactgct agcaaatggc agaaccaaag ctcaaataaa    960
aataaaataa ttttcattca ttcactc                                        987
```

<210> SEQ ID NO 14
<211> LENGTH: 12
<212> TYPE: DNA
<213> ORGANISM: Homo sapiens

<400> SEQUENCE: 14

```
aacgggcggc gg                                                         12
```

<210> SEQ ID NO 15
<211> LENGTH: 10
<212> TYPE: DNA
<213> ORGANISM: Homo sapiens

<400> SEQUENCE: 15

```
cacggcgcgg                                                            10
```

<210> SEQ ID NO 16
<211> LENGTH: 8
<212> TYPE: DNA
<213> ORGANISM: Homo sapiens

<400> SEQUENCE: 16

```
cgggcggc                                                               8
```

<210> SEQ ID NO 17
<211> LENGTH: 8
<212> TYPE: DNA
<213> ORGANISM: Homo sapiens

<400> SEQUENCE: 17

```
agcagcat                                                               8
```

<210> SEQ ID NO 18
<211> LENGTH: 8
<212> TYPE: DNA
<213> ORGANISM: Homo sapiens

<400> SEQUENCE: 18

```
gcgccgac                                                               8
```

```
<210> SEQ ID NO 19
<211> LENGTH: 649
<212> TYPE: DNA
<213> ORGANISM: Homo sapiens

<400> SEQUENCE: 19
ccacctaatt gtactgaatt gcaaattgat agttgttcta gcagtgaaga gataaagaaa       60
aaaaagtaca accaaatgcc agtcaggcac agcagaaacc tacaactcat ggaaggtaaa      120
gaacctgcaa ctggagccaa gaagagtaac aagccaaatg aacagacaag taaaagacat      180
gacagcgata ctttcccaga gctgaagtta acaaatgcac ctggttcttt tactaagtgt      240
tcaaatacca gtgaacttaa agaatttgtc aatcctagcc ttccaagaga agaaaaagaa      300
gagaaactag aaacagttag tgtctaataa tgctgaagac cccaaagatc tcatgttaag      360
tggagaaagg ttttgcaaa ctgaaagatc tgtagagagt agcagtattt cattggtacc       420
tggtactgat tatggcactc aggaaagtat ctcgttactg gaagttagca ctctagggaa      480
ggcaaaaaca gaaccaaata aatgtgtgag tcagtgtgca gcatttgaaa accccaaggg      540
actaattcat ggttgttcca agataatag aaatgacaca gaaggcttta agtatccatt       600
gggacatgaa gttaaccaca gtcgggaaac aagcatagaa atggaagaa                  649

<210> SEQ ID NO 20
<211> LENGTH: 10
<212> TYPE: DNA
<213> ORGANISM: Homo sapiens

<400> SEQUENCE: 20
aggcacagca                                                              10

<210> SEQ ID NO 21
<211> LENGTH: 8
<212> TYPE: DNA
<213> ORGANISM: Homo sapiens

<400> SEQUENCE: 21 gtgcagca                                                                 8

<210> SEQ ID NO 22
<211> LENGTH: 8
<212> TYPE: DNA
<213> ORGANISM: Homo sapiens

<400> SEQUENCE: 22 cagcgata                                                                 8

<210> SEQ ID NO 23
<211> LENGTH: 8
<212> TYPE: DNA
<213> ORGANISM: Homo sapiens

<400> SEQUENCE: 23 tagcagtg                                                                 8

<210> SEQ ID NO 24
<211> LENGTH: 8
<212> TYPE: DNA
<213> ORGANISM: Homo sapiens

<400> SEQUENCE: 24 aggcttta                                                                 8
```

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ctggatcctt gccccgcccc ttgaattccc                                   30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gggaattcaa atgacgtcaa aaggatccag                                   30

<210> SEQ ID NO 27
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctacccacc ctggatcctt gccccgcccc ttgaattccc aaccctccac             50

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atccttgccc cgccccttga at                                           22

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttgccccgcc cctt                                                    14

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: 5-aza-cytosine

```
<400> SEQUENCE: 30
ctggatcctt gccccgcccc ttgaattccc                                              30

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: 5-aza-cytosine
<220> FEATURE:
<221> NAME/KEY: modified_base
<222> LOCATION: (11)..(11)
<223> OTHER INFORMATION: 5-aza-cytosine
<220> FEATURE:
<221> NAME/KEY: modified_base
<222> LOCATION: (21)..(21)
<223> OTHER INFORMATION: cytosine or 5-methyl-2'-deoxycytidine

<400> SEQUENCE: 31
ctgaacggat cgtttcgatc cgttcag                                                 27

<210> SEQ ID NO 32
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 5-aza-cytosine
<220> FEATURE:
<221> NAME/KEY: modified_base
<222> LOCATION: (5)..(5)
<223> OTHER INFORMATION: 5-aza-cytosine

<400> SEQUENCE: 32 ttcgcgaa                                                                       8

<210> SEQ ID NO 33
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 ttcgcgaa                                                                       8
```